(12) United States Patent
Monahan et al.

(10) Patent No.: US 7,361,511 B2
(45) Date of Patent: Apr. 22, 2008

(54) COMPOSITIONS, KITS, AND METHODS FOR IDENTIFICATION, ASSESSMENT, PREVENTION, AND THERAPY OF CERVICAL CANCER

(75) Inventors: John E. Monahan, Walpole, MA (US); Xumei Zhao, Wayland, MA (US); Yan Chen, Cambridge, MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 359 days.

(21) Appl. No.: 10/645,756

(22) Filed: Aug. 20, 2003

(65) Prior Publication Data
US 2005/0037010 A1 Feb. 17, 2005

Related U.S. Application Data

(60) Provisional application No. 60/404,770, filed on Aug. 20, 2002.

(51) Int. Cl.
*G01N 33/50* (2006.01)
(52) U.S. Cl. .............. 436/64; 435/6; 435/7.23; 530/350; 530/387.7; 536/23.1; 536/23.5; 536/24.3
(58) Field of Classification Search .............. 435/7.23, 435/7.1, 6, 91.2; 530/350, 387.7; 536/23.5, 536/23.1, 24.3; 436/64, 501
See application file for complete search history.

(56) References Cited

U.S. PATENT DOCUMENTS

| | | | |
|---|---|---|---|
| 2002/0009724 A1* | 1/2002 | Schlegel et al. | 435/6 |
| 2003/0087270 A1* | 5/2003 | Schlegel et al. | 435/6 |
| 2003/0138792 A1* | 7/2003 | Schlegel et al. | 435/6 |

FOREIGN PATENT DOCUMENTS

| | | | |
|---|---|---|---|
| WO | WO 02/101075 | * | 12/2002 |
| WO | WO 2004/018999 A2 | | 3/2004 |
| WO | WO 2004/018999 A3 | | 3/2004 |

OTHER PUBLICATIONS

Chen et al. (Cancer Res. Apr. 15, 2003; 63: 1927-1935).*
Cheng et al. (Int. J. Cancer. 2002; 98: 419-426).*

* cited by examiner

*Primary Examiner*—Stephen L. Rawlings
(74) *Attorney, Agent, or Firm*—Lahive & Cockfield, LLP; Maria Laccotripe Zacharakis; Giulio A. DeConti, Jr., Esq.

(57) ABSTRACT

The invention relates to nucleic acid molecules and proteins associated with cervical cancer including pre-malignant conditions such as dysplasia. Compositions, kits, and methods for detecting, characterizing, preventing, and treating human cervical cancers are also provided.

22 Claims, 2 Drawing Sheets

MCM 6

Claudin 1

SEQUENCE LISTING

<160> NUMBER OF SEQ ID NOS: 44

<210> SEQ ID NO 1
<211> LENGTH: 2848
<212> TYPE: DNA
<213> ORGANISM: Homo sapiens

<400> SEQUENCE: 1

```
actttccctt tcgaattcct cggtatatct tggggactgg aggacctgtc tggttattat      60
acagacgcat aactggaggt gggatccaca cagctcagaa cagctggatc ttgctcagtc     120
tctgccaggg gaagattcct tggaggaggc cctgcagcga catggaggga gctgctttgc     180
tgagagtctc tgtcctctgc atctggatga gtgcactttt ccttggtgtg ggagtgaggg     240
cagaggaagc tggagcgagg gtgcaacaaa acgttccaag tgggacagat actggagatc     300
ctcaaagtaa gccctcggt gactgggctg ctggcaccat ggacccagag agcagtatct     360
ttattgagga tgccattaag tatttcaagg aaaaagtgag cacacagaat ctgctactcc     420
```

```
tgctgactga taatgaggcc tggaacggat tcgtggctgc tgctgaactg cccaggaatg    480
aggcagatga gctccgtaaa gctctggaca accttgcaag acaaatgatc atgaaagaca    540
aaaactggca cgataaaggc cagcagtaca gaaactggtt tctgaaagag tttcctcggt    600
tgaaaagtaa gcttgaggat aacataagaa ggctccgtgc ccttgcagat ggggttcaga    660
aggtccacaa aggcaccacc atcgccaatg tggtgtctgg ctctctcagc atttcctctg    720
gcatcctgac cctcgtcggc atgggtctgg cacccttcac agagggaggc agccttgtac    780
tcttggaacc tgggatggag ttgggaatca cagcagcttt gaccgggatt accagcagta    840
ccatagacta cggaaagaag tggtggacac aagcccaagc ccacgacctg gtcatcaaaa    900
gccttgacaa attgaaggag gtgaaggagt ttttgggtga aacatatcc aactttcttt    960 ccttagctgg caatacttac caactcacac gaggcattgg aaggacatc cgtgccctca   1020 gacgagccag agccaatctt cagtcagtac cgcatgcctc agcctcacgc ccccgggtca   1080
ctgagccaat ctcagctgaa agcggtgaac aggtggagag agttaatgaa cccagcatcc   1140
tggaaatgag cagaggagtc aagctcacgg atgtggcccc tgtaagcttc tttcttgtgc   1200
tggatgtagt ctacctcgtg tacgaatcaa agcacttaca tgagggggca aagtcagaga   1260
cagctgagga gctgaagaag gtggctcagg agctggagga gaagctaaac attctcaaca   1320
ataattataa gattctgcag gcggaccaag aactgtgacc acagggcagg gcagccacca   1380
ggagagatat gcctggcagg ggccaggaca aaatgcaaac ttttttttttt ttctgagaca   1440 gagtcttgct ctgtcgccaa gttggagtgc aatggtgcga tctcagctca ctgcaagctc   1500
tgcctcccgt gttcaagcga ttctcctgcc ttggcctccc aagtagctgg gactacaggc   1560
gcctaccacc atgcccagct aattttgta ttttttaatag atgggggtt tcaccatgtt   1620 ggccaggatg gtctcgatct cctgacctct tgatctgccc accttggcct cccaaagtgc   1680
tgggattaca ggcgtgagcc atcgcttttg acccaaatgc aaacatttta ttaggggggat   1740 aaagagggtg aggtaaagtt tatggaactg agtgttaggg actttggcat ttccatagct   1800
gagcacagca ggggagggt taatgcagat ggcagtgcag caaggagaag gcaggaacat   1860
tggagcctgc aataagggaa aaatgggaac tggagagtgt ggggaatggg aagaagcagt   1920
ttactttaga ctaaagaata tattgggggg ccgggtgtag tggctcatgc ctgtaatccg   1980
agcactttgg gaggccaagg cgggcggatc acgaggtcag gagatcaaga ccatcctggc   2040
taacacagtg aaacccccgtc tctactaaaa atacaaaaaa ttagccgggc atggtggcgg   2100
gcgcctgtag ttccagctaa ctgggcggct gaggcaggag aatggcgtga acctgggagg   2160
tggagcttgc agtgagccga gatatcgcca ctgcactcca gcctgggtga cagagcgaga   2220
ctccatctca aaaaaaaaaa aaaaaagaat atattgacgg aagaatagag aggaggcttg   2280
aaggaaccag caatgagaag gccaggaaaa gaaagagctg aaaatggaga aagcccaaga   2340
gttagaacag ttggatacag gagaagaaac agcggctcca ctacagaccc agccccaggt   2400
tcaatgtcct ccgaagaatg aagtctttcc ctggtgatgg tccctgcccc tgtctttcca   2460
gcatccactc tcccttgtcc tcctgggggc atatctcagt caggcagcgg cttcctgatg   2520
atggtcgttg gggtggttgt catgtgatgg gtccctcca ggttactaaa gggtgcatgt   2580
cccctgcttg aacactgaag ggcaggtggt gggccatggc catggtcccc agctgaggag   2640
caggtgtccc tgagaaccca aacttcccag agagtatgtg agaaccaacc aatgaaaaca   2700
gtcccatcgc tcttacccgg taagtaaaca gtcagaaaat tagcatgaaa gcagtttagc   2760
```

-continued

```
attgggagga agctcagatc tctagagctg tcttgtcgcc gcccaggatt gacctgtgtg    2820
taagtcccaa taaactcacc tactcatc                                       2848

<210> SEQ ID NO 2
<211> LENGTH: 398
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Glu | Gly | Ala | Ala | Leu | Leu | Arg | Val | Ser | Val | Leu | Cys | Ile | Trp | Met |
| 1 | | | | 5 | | | | | 10 | | | | | 15 | |
| Ser | Ala | Leu | Phe | Leu | Gly | Val | Gly | Val | Arg | Ala | Glu | Glu | Ala | Gly | Ala |
| | | | 20 | | | | | 25 | | | | | 30 | | |
| Arg | Val | Gln | Gln | Asn | Val | Pro | Ser | Gly | Thr | Asp | Thr | Gly | Asp | Pro | Gln |
| | | 35 | | | | | 40 | | | | | 45 | | | |
| Ser | Lys | Pro | Leu | Gly | Asp | Trp | Ala | Ala | Gly | Thr | Met | Asp | Pro | Glu | Ser |
| | 50 | | | | | 55 | | | | | 60 | | | | |
| Ser | Ile | Phe | Ile | Glu | Asp | Ala | Ile | Lys | Tyr | Phe | Lys | Glu | Lys | Val | Ser |
| 65 | | | | | 70 | | | | | 75 | | | | | 80 |
| Thr | Gln | Asn | Leu | Leu | Leu | Leu | Thr | Asp | Asn | Glu | Ala | Trp | Asn | Gly | |
| | | | | 85 | | | | | 90 | | | | | 95 | |
| Phe | Val | Ala | Ala | Ala | Glu | Leu | Pro | Arg | Asn | Glu | Ala | Asp | Glu | Leu | Arg |
| | | | | 100 | | | | | 105 | | | | | 110 | |
| Lys | Ala | Leu | Asp | Asn | Leu | Ala | Arg | Gln | Met | Ile | Met | Lys | Asp | Lys | Asn |
| | | | 115 | | | | | 120 | | | | | 125 | | |
| Trp | His | Asp | Lys | Gly | Gln | Gln | Tyr | Arg | Asn | Trp | Phe | Leu | Lys | Glu | Phe |
| | 130 | | | | | 135 | | | | | 140 | | | | |
| Pro | Arg | Leu | Lys | Ser | Lys | Leu | Glu | Asp | Asn | Ile | Arg | Arg | Leu | Arg | Ala |
| 145 | | | | | 150 | | | | | 155 | | | | | 160 |
| Leu | Ala | Asp | Gly | Val | Gln | Lys | Val | His | Lys | Gly | Thr | Thr | Ile | Ala | Asn |
| | | | | 165 | | | | | 170 | | | | | 175 | |
| Val | Val | Ser | Gly | Ser | Leu | Ser | Ile | Ser | Ser | Gly | Ile | Leu | Thr | Leu | Val |
| | | | 180 | | | | | 185 | | | | | 190 | | |
| Gly | Met | Gly | Leu | Ala | Pro | Phe | Thr | Glu | Gly | Gly | Ser | Leu | Val | Leu | Leu |
| | | 195 | | | | | 200 | | | | | 205 | | | |
| Glu | Pro | Gly | Met | Glu | Leu | Gly | Ile | Thr | Ala | Ala | Leu | Thr | Gly | Ile | Thr |
| | 210 | | | | | 215 | | | | | 220 | | | | |
| Ser | Ser | Thr | Ile | Asp | Tyr | Gly | Lys | Lys | Trp | Trp | Thr | Gln | Ala | Gln | Ala |
| 225 | | | | | 230 | | | | | 235 | | | | | 240 |
| His | Asp | Leu | Val | Ile | Lys | Ser | Leu | Asp | Lys | Leu | Lys | Glu | Val | Lys | Glu |
| | | | | 245 | | | | | 250 | | | | | 255 | |
| Phe | Leu | Gly | Glu | Asn | Ile | Ser | Asn | Phe | Leu | Ser | Leu | Ala | Gly | Asn | Thr |
| | | | 260 | | | | | 265 | | | | | 270 | | |
| Tyr | Gln | Leu | Thr | Arg | Gly | Ile | Gly | Lys | Asp | Ile | Arg | Ala | Leu | Arg | Arg |
| | | 275 | | | | | 280 | | | | | 285 | | | |
| Ala | Arg | Ala | Asn | Leu | Gln | Ser | Val | Pro | His | Ala | Ser | Ala | Ser | Arg | Pro |
| | 290 | | | | | 295 | | | | | 300 | | | | |
| Arg | Val | Thr | Glu | Pro | Ile | Ser | Ala | Glu | Ser | Gly | Glu | Gln | Val | Glu | Arg |
| 305 | | | | | 310 | | | | | 315 | | | | | 320 |
| Val | Asn | Glu | Pro | Ser | Ile | Leu | Glu | Met | Ser | Arg | Gly | Val | Lys | Leu | Thr |
| | | | | 325 | | | | | 330 | | | | | 335 | |
| Asp | Val | Ala | Pro | Val | Ser | Phe | Phe | Leu | Val | Leu | Asp | Val | Val | Tyr | Leu |
| | | | 340 | | | | | 345 | | | | | 350 | | |
| Val | Tyr | Glu | Ser | Lys | His | Leu | His | Glu | Gly | Ala | Lys | Ser | Glu | Thr | Ala |

```
                355                 360                 365
Glu Glu Leu Lys Lys Val Ala Gln Glu Leu Glu Lys Leu Asn Ile
    370                 375                 380

Leu Asn Asn Asn Tyr Lys Ile Leu Gln Ala Asp Gln Glu Leu
385                 390                 395

<210> SEQ ID NO 3
<211> LENGTH: 2545
<212> TYPE: DNA
<213> ORGANISM: Homo sapiens

<400> SEQUENCE: 3
gtgctgggga gcagcgtgtt tactgtgctt ggtcatgagc tgctgggaag ttgtgacttt      60
cactttccct ttcgaattcc agggtatatc tgggaggccg gaggacgtgt ctggttatta     120
cacagatgca cagctggacg tgggatccac acagctcaga acagttggat cttgctcagt     180
ctctgtcaga ggaagatccc ttggacaaga ggaccctgcc ttggtgtgag agtgagggaa     240
gaggaagctg gaacgagggt taaggaaaac cttccagtct ggacagtgac tggagagctc     300
caaggaaagc ccctcggtaa cccagccgct ggcaccatga cccagagag cagtatcttt     360 attgaggatt accttaagta tttccaggac caagtgagca gagagaatct gctacaactg     420
ctgactgatg atgaagcctg aatggattc gtggctgctg ctgaactgcc cagggatgag     480
gcagatgagc tccgtaaagc tctgaacaag cttgcaagtc acatggtcat gaaggacaaa     540
aaccgccacg ataaagacca gcagcacagg cagtggtttt tgaaagagtt tcctcggttg     600
aaaagggagc ttgaggatca cataaggaag ctccgtgccc ttgcagagga ggttgagcag     660
gtccacagag gcaccaccat tgccaatgtg tgtccaact ctgttggcac tacctctggc     720
atcctgaccc tcctcggcct gggtctggca cccttcacag aaggaatcag ttttgtgctc     780
ttggacactg gcatgggtct gggagcagca gctgctgtgg ctgggattac ctgcagtgtg     840
gtagaactag taaacaaatt gcgggcacga gcccaagccc gcaacttgga ccaaagcggc     900
accaatgtag caaggtgat gaaggagttt gtgggtggga acacacccaa tgttcttacc     960
ttagttgaca attggtacca agtcacacaa gggattggga ggaacatccg tgccatcaga    1020
cgagccagag ccaaccctca gttaggagcg tatgccccac ccccgcatat cattgggcga    1080
atctcagctg aaggcggtga acaggttgag agggttgttg aaggcccgc ccaggcaatg    1140 agcagaggaa ccatgatcgt gggtgcagcc actggaggca tcttgcttct gctggatgtg    1200
gtcagccttg catatgagtc aaagcacttg cttgaggggg caaagtcaga gtcagctgag    1260
gagctgaaga gcgggctca ggagctggag gggaagctca actttctcac caagatccat    1320
gagatgctgc agccaggcca agaccaatga ccccagagca gtgcagccac cagggcagaa    1380
atgccgggca caggccagga caaaatgcag acttttttt tttttttttt tttttttga    1440 gatggagtct cgctctatcg cccaggatgg agtgcagtgg ctcaatctcg ctcactgca    1500 aactccgcct cccgggttca caccattctc cggcctcagt ctcccgagta gctgggacta    1560
caggcacctg ccaccacgcc cggctaattt ttttgtattt tcactggaga cggggtttca    1620
ctgtgttagc cacgatggtc tccatctcct gacctcgtga tctgcccacc tcggcctccc    1680
aaagtgctgg gattacaggc gtgagccacc gcgcctggcc aaaatgcaga cattttatta    1740
gggggataag gagggcaagg taaagcttat ggaactgagt gttagtgact ttggcatttg    1800
tgtagctgag cacagcaagg gaggggttaa tgcagatggc aagtgcacca aggagaaggc    1860
aggaacactg gagcctgcaa taagggagga gagaggactg gagagtgtgg ggaatgggaa    1920
```

```
gaagtagttt actttggact aaagaatata ttgggcgaag aatagagggg gagcttgcag    1980
gaaccagcaa tgagaaggcc aggaaaagaa agagctgaaa atggagaaaa ccagagttag    2040
aactgttgga tacaggagaa gaaacagcag ctccactacc gaccccccccc caggtttgat   2100 gtccttccaa gaataaagtc tttccctggt gatggtctct cgctctgtct ttccagcatc    2160
cactctccct tgtccttctg ggggtgtatc acagtcagcc agtggcttct tcatgatggt    2220
ggttggggtg gttgtcatgt gacgggtccc ctccaggtta ctaaagggtg catgtcccct    2280
gcttgaaccc tgagaggcag gtggtaggcc atggccacaa tccccagctg aggagcaggt    2340
gtccctgaga acccaaactt cccagagagt atctgagaac caaccaatga aacagtccc    2400 atcgctctta gccggtaagt aaacagtcag aagattagca tgaaagcagt ttagcattgg    2460
gaggaagcac agatctctag agctgtcctg tcgctgccca ggattgacct gtgtgtaagt    2520
cccaataaac tcacctactc accaa                                          2545
```

<210> SEQ ID NO 4
<211> LENGTH: 337
<212> TYPE: PRT
<213> ORGANISM: Homo sapiens

<400> SEQUENCE: 4

```
Met Asn Pro Glu Ser Ser Ile Phe Ile Glu Asp Tyr Leu Lys Tyr Phe
 1               5                  10                  15

Gln Asp Gln Val Ser Arg Glu Asn Leu Leu Gln Leu Leu Thr Asp Asp
             20                  25                  30

Glu Ala Trp Asn Gly Phe Val Ala Ala Ala Glu Leu Pro Arg Asp Glu
         35                  40                  45

Ala Asp Glu Leu Arg Lys Ala Leu Asn Lys Leu Ala Ser His Met Val
     50                  55                  60

Met Lys Asp Lys Asn Arg His Asp Lys Asp Gln Gln His Arg Gln Trp
 65                  70                  75                  80

Phe Leu Lys Glu Phe Pro Arg Leu Lys Arg Glu Leu Glu Asp His Ile
                 85                  90                  95

Arg Lys Leu Arg Ala Leu Ala Glu Glu Val Glu Gln Val His Arg Gly
            100                 105                 110

Thr Thr Ile Ala Asn Val Val Ser Asn Ser Val Gly Thr Thr Ser Gly
        115                 120                 125

Ile Leu Thr Leu Leu Gly Leu Gly Leu Ala Pro Phe Thr Glu Gly Ile
    130                 135                 140

Ser Phe Val Leu Leu Asp Thr Gly Met Gly Leu Gly Ala Ala Ala Ala
145                 150                 155                 160

Val Ala Gly Ile Thr Cys Ser Val Val Glu Leu Val Asn Lys Leu Arg
                165                 170                 175

Ala Arg Ala Gln Ala Arg Asn Leu Asp Gln Ser Gly Thr Asn Val Ala
            180                 185                 190

Lys Val Met Lys Glu Phe Val Gly Gly Asn Thr Pro Asn Val Leu Thr
        195                 200                 205

Leu Val Asp Asn Trp Tyr Gln Val Thr Gln Gly Ile Gly Arg Asn Ile
    210                 215                 220

Arg Ala Ile Arg Arg Ala Arg Ala Asn Pro Gln Leu Gly Ala Tyr Ala
225                 230                 235                 240

Pro Pro Pro His Ile Ile Gly Arg Ile Ser Ala Glu Gly Gly Glu Gln
                245                 250                 255
```

-continued

```
Val Glu Arg Val Val Glu Gly Pro Ala Gln Ala Met Ser Arg Gly Thr
            260                 265                 270
Met Ile Val Gly Ala Ala Thr Gly Gly Ile Leu Leu Leu Leu Asp Val
        275                 280                 285
Val Ser Leu Ala Tyr Glu Ser Lys His Leu Leu Glu Gly Ala Lys Ser
    290                 295                 300
Glu Ser Ala Glu Glu Leu Lys Lys Arg Ala Gln Glu Leu Glu Gly Lys
305                 310                 315                 320
Leu Asn Phe Leu Thr Lys Ile His Glu Met Leu Gln Pro Gly Gln Asp
                325                 330                 335
Gln

<210> SEQ ID NO 5
<211> LENGTH: 2100
<212> TYPE: DNA
<213> ORGANISM: Homo sapiens

<400> SEQUENCE: 5
agacgccccg aggtcggagt gaagcgccgg gaccgagccc cgtctcccag ggagtccggg      60
gcgcacggca ccgaggagag cgcgggagcc aacctgggcg catcatgcgc agggcccggg     120
acgctgggcc ggtctacacc gccgcctggg tcacgtggcc cggacgggcc ggcggctgcc     180
ccggccgggg ggcgggggtc gcgccggggt tgcgctggac gacggagagc ggcgggcccg     240
cagcggcctg gagcctccca acccgcgccg cgctggccct cgagcgtagg agccgccccc     300
tgcccccccg cgccggcccc cgcgccgccg ccccgccccc tatatagcgc gccccagcag     360
ggcccgcgcc aggccgccag cctcggagtg ggcgcgggac agtgcgcggc gccccgcagc     420
caggcccccg cccccgccgc atccacctcc tccgccgcct cgacccaac gggcgccccc      480 cgccgcggca gctgccgccg ggccccgcg ccaccatga agaaggaggt gtgctccgtg        540
gccttcctca aggccgtgtt cgcagagttc ttggccaccc tcatcttcgt cttctttggc     600
ctgggctcgg ccctcaagtg gccgtcggcg ctgcctacca tcctgcagat cgcgctggcg     660
tttggcctgg ccataggcac gctggcccag gccctgggac ccgtgagcgg cggccacatc     720
aaccccgcca tcaccctggc cctcttggtg ggcaaccaga tctcgctgct ccgggctttc     780
ttctacgtgg cggcccagct ggtgggcgcc attgccgggg ctggcatcct ctacggtgtg     840
gcaccgctca atgcccgggg caatctggcc gtcaacgcgc tcaacaacaa cacaacgcag     900
ggccaggcca tggtggtgga gctgattctg accttccagc tggcactctg catcttcgcc     960
tccactgact cccgccgcac cagccctgtg ggctccccag ccctgtccat ggcctgtctg    1020
gtcaccctgg ccaccttgt cggaatctac ttcactggct gctccatgaa cccagcccgc    1080
tcttttggcc ctgcggtggt catgaatcgg ttcagccccg ctcactgggt tttctgggta    1140
gggcccatcg tggggcggt cctggctgcc atcctttact ctacctgct cttccccaac      1200 tccctgagcc tgagtgagcg tgtggccatc atcaaaggca cgtatgagcc tgacgaggac    1260
tgggaggagc agcgggaaga gcggaagaag accatggagc tgaccacccg ctgaccagtg    1320
tcaggcaggg gccagccct cagcccctga gccaaggggg aaaagaagaa aaagtaccta     1380
acacaagctt ccttttttgca caaccggtcc tcttggctga ggaggaggag ctggtcaccc    1440
tggctgcaca gttagagagg ggagaaggaa cccatgatgg gactcctggg gtaggggcca    1500
ggggctgggg tctgctgggg acaggtctct ctgggacaga cctcagagat tgtgaatgca    1560
gtgccaagct cacaggctgc aagggccagg ccagaaaagg gtgggcctgc agcctgcacc    1620
```

```
cccccaccttc cccaaccctt cctcaagagc tgaagggatc ccagcccta ggtgggcaga    1680 ggcagaccct ccccagagct ccttaggaag aagacagact ggttcattga atgccgcctt    1740
atttatttct ggtgaggatg catgcgtggg gctgctggtg tttagagtgg gggctaccca    1800
ataaatcact gatactcaaa acaccagcag accctcccca gagctcctta ggaagaagac    1860
agactggttc attgaatgcc gccttattta tttctggtga ggatgcatgc gtggggctgc    1920
tggtgtttag agtgggggct acccaataaa tcactgatac tcacattccg cctctgtctc    1980
tcctcagagt gccttgagac actctggccc attgcctctc ctctttgtca tcccacatcc    2040
tccaccacga tctccacagg gtaccagggg accccaggac aagtgctctg tgggaagaaa    2100
```

<210> SEQ ID NO 6
<211> LENGTH: 265
<212> TYPE: PRT
<213> ORGANISM: Homo sapiens

<400> SEQUENCE: 6

```
Met Lys Lys Glu Val Cys Ser Val Ala Phe Leu Lys Ala Val Phe Ala
 1               5                  10                  15

Glu Phe Leu Ala Thr Leu Ile Phe Val Phe Phe Gly Leu Gly Ser Ala
            20                  25                  30

Leu Lys Trp Pro Ser Ala Leu Pro Thr Ile Leu Gln Ile Ala Leu Ala
        35                  40                  45

Phe Gly Leu Ala Ile Gly Thr Leu Ala Gln Ala Leu Gly Pro Val Ser
    50                  55                  60

Gly Gly His Ile Asn Pro Ala Ile Thr Leu Ala Leu Leu Val Gly Asn
65                  70                  75                  80

Gln Ile Ser Leu Leu Arg Ala Phe Phe Tyr Val Ala Ala Gln Leu Val
                85                  90                  95

Gly Ala Ile Ala Gly Ala Gly Ile Leu Tyr Gly Val Ala Pro Leu Asn
           100                 105                 110

Ala Arg Gly Asn Leu Ala Val Asn Ala Leu Asn Asn Asn Thr Thr Gln
       115                 120                 125

Gly Gln Ala Met Val Val Glu Leu Ile Leu Thr Phe Gln Leu Ala Leu
   130                 135                 140

Cys Ile Phe Ala Ser Thr Asp Ser Arg Arg Thr Ser Pro Val Gly Ser
145                 150                 155                 160

Pro Ala Leu Ser Ile Gly Leu Ser Val Thr Leu Gly His Leu Val Gly
               165                 170                 175

Ile Tyr Phe Thr Gly Cys Ser Met Asn Pro Ala Arg Ser Phe Gly Pro
           180                 185                 190

Ala Val Val Met Asn Arg Phe Ser Pro Ala His Trp Val Phe Trp Val
       195                 200                 205

Gly Pro Ile Val Gly Ala Val Leu Ala Ala Ile Leu Tyr Phe Tyr Leu
   210                 215                 220

Leu Phe Pro Asn Ser Leu Ser Leu Ser Glu Arg Val Ala Ile Ile Lys
225                 230                 235                 240

Gly Thr Tyr Glu Pro Asp Glu Asp Trp Glu Glu Gln Arg Glu Glu Arg
               245                 250                 255

Lys Lys Thr Met Glu Leu Thr Thr Arg
           260                 265
```

<210> SEQ ID NO 7
<211> LENGTH: 1935
<212> TYPE: DNA

<213> ORGANISM: Homo sapiens

<400> SEQUENCE: 7

| | | | | | |
|---|---|---|---|---|---|
| agacgccccg | aggtcggagt | gaagcgccgg | gaccgagccc | cgtctcccag | ggagtccggg | 60 |
| gcgcacggca | ccgaggagag | cgcgggagcc | aacctgggcg | catcatgcgc | agggcccggg | 120 |
| acgctgggcc | ggtctacacc | gccgcctggg | tcacgtggcc | cggacgggcc | ggcggctgcc | 180 |
| ccggccgggg | ggcgggggtc | gcgccggggt | tgcgctggac | gacggagagc | ggcgggcccg | 240 |
| cagcggcctg | gagcctccca | acccgcgccg | cgctggccct | cgagcgtagg | agccgccccc | 300 |
| tgccccccg | cgccggcccc | gcgccggcc | gcccgcccc | tatatagcgc | gccccagcag | 360 |
| ggcccgcgcc | aggccgccag | cctcggagtg | ggcgcgggac | agtgcgcggc | gccccgcagc | 420 |
| caggcccccg | ccccgccgc | atccacctcc | tccgccgcct | cgacccaac | gggcgccccc | 480 |
| cgccgcggca | gctgccgccg | ggccccgcg | gccaccatga | agaaggaggt | gtgctccgtg | 540 |
| gccttcctca | aggccgtgtt | cgcagagttc | ttggccaccc | tcatcttcgt | cttctttggc | 600 |
| ctgggctcgg | ccctcaagtg | gccgtcggcg | ctgcctacca | tcctgcagat | cgcgctggcg | 660 |
| tttggcctgg | ccataggcac | gctggcccag | gccctgggac | ccgtgagcgg | cggccacatc | 720 |
| aaccccgcca | tcaccctggc | cctcttggtg | ggcaaccaga | tctcgctgct | ccgggctttc | 780 |
| ttctacgtgg | cggcccagct | ggtgggcgcc | attgccgggg | ctggcatcct | ctacggtgtg | 840 |
| gcaccgctca | atgcccgggg | caatctggcc | gtcaacgcga | tctacttcac | tggctgctcc | 900 |
| atgaacccag | cccgctcttt | tggccctgcg | gtggtcatga | atcggttcag | ccccgctcac | 960 |
| tgggttttct | gggtagggcc | catcgtgggg | gcggtcctgg | ctgccatcct | ttacttctac | 1020 |
| ctgctcttcc | ccaactccct | gagcctgagt | gagcgtgtgg | ccatcatcaa | aggcacgtat | 1080 |
| gagcctgacg | aggactggga | ggagcagcgg | gaagagcgga | agaagaccat | ggagctgacc | 1140 |
| acccgctgac | cagtgtcagg | cagggccag | cccctcagcc | cctgagccaa | ggggaaaag | 1200 |
| aagaaaaagt | acctaacaca | agcttccttt | ttgcacaacc | ggtcctcttg | gctgaggagg | 1260 |
| aggagctggt | caccctggct | gcacagttag | agagggaga | aggaacccat | gatgggactc | 1320 |
| ctggggtagg | ggccaggggc | tggggtctgc | tggggacagg | tctctctggg | acagacctca | 1380 |
| gagattgtga | atgcagtgcc | aagctcacag | gctgcaaggg | ccaggccaga | aaagggtggg | 1440 |
| cctgcagcct | gcacccccca | ccttccccaa | cccttcctca | agagctgaag | ggatcccagc | 1500 |
| ccctaggtgg | gcagaggcag | accctcccca | gagctcctta | ggaagaagac | agactggttc | 1560 |
| attgaatgcc | gccttattta | tttctggtga | ggatgcatgc | gtggggctgc | tggtgtttag | 1620 |
| agtgggggct | acccaataaa | tcactgatac | tcaaaacacc | agcagaccct | cccagagct | 1680 |
| ccttaggaag | aagacagact | ggttcattga | atgccgcctt | atttatttct | ggtgaggatg | 1740 |
| catgcgtggg | gctgctggtg | tttagagtgg | gggctaccca | ataaatcact | gatactcaca | 1800 |
| ttccgcctct | gtctctcctc | agagtgcctt | gagacactct | ggcccattgc | ctctcctctt | 1860 |
| tgtcatccca | catcctccac | cacgatctcc | acagggtacc | aggggacccc | aggacaagtg | 1920 |
| ctctgtggga | agaaa | | | | | 1935 |

<210> SEQ ID NO 8
<211> LENGTH: 210
<212> TYPE: PRT
<213> ORGANISM: Homo sapiens

<400> SEQUENCE: 8

Met Lys Lys Glu Val Cys Ser Val Ala Phe Leu Lys Ala Val Phe Ala

```
                1               5                    10                   15
          Glu Phe Leu Ala Thr Leu Ile Phe Val Phe Phe Gly Leu Gly Ser Ala
                         20                  25                  30
          Leu Lys Trp Pro Ser Ala Leu Pro Thr Ile Leu Gln Ile Ala Leu Ala
                         35                  40                  45
          Phe Gly Leu Ala Ile Gly Thr Leu Ala Gln Ala Leu Gly Pro Val Ser
                         50                  55                  60
          Gly Gly His Ile Asn Pro Ala Ile Thr Leu Ala Leu Val Gly Asn
           65                  70                  75                  80
          Gln Ile Ser Leu Leu Arg Ala Phe Phe Tyr Val Ala Ala Gln Leu Val
                         85                  90                  95
          Gly Ala Ile Ala Gly Ala Gly Ile Leu Tyr Gly Val Ala Pro Leu Asn
                        100                 105                 110
          Ala Arg Gly Asn Leu Ala Val Asn Ala Ile Tyr Phe Thr Gly Cys Ser
                        115                 120                 125
          Met Asn Pro Ala Arg Ser Phe Gly Pro Ala Val Val Met Asn Arg Phe
                        130                 135                 140
          Ser Pro Ala His Trp Val Phe Trp Val Gly Pro Ile Val Gly Ala Val
          145                 150                 155                 160
          Leu Ala Ala Ile Leu Tyr Phe Tyr Leu Leu Phe Pro Asn Ser Leu Ser
                        165                 170                 175
          Leu Ser Glu Arg Val Ala Ile Ile Lys Gly Thr Tyr Glu Pro Asp Glu
                        180                 185                 190
          Asp Trp Glu Glu Gln Arg Glu Glu Arg Lys Lys Thr Met Glu Leu Thr
                        195                 200                 205
          Thr Arg
              210

<210> SEQ ID NO 9
<211> LENGTH: 2180
<212> TYPE: DNA
<213> ORGANISM: Homo sapiens

<400> SEQUENCE: 9
agacgccccg aggtcggagt gaagcgccgg gaccgagccc cgtctcccag ggagtccggg      60
gcgcacggca ccgaggagag cgcgggagcc aacctgggcg catcatgcgc agggcccggg     120
acgctgggcc ggtctacacc gccgcctggg tcacgtggcc cggacgggcc ggcggctgcc     180
ccggccgggg ggcgggggtc gcgccggggt gcgctggaca cggagagc ggcgggcccg       240
cagcggcctg gagcctccca acccgcgccg cgctggccct cgagcgtagg agccgccccc     300
tgccccccg cgcggccccc gcgccccgcc gcccgccccc tatatagcgc gcccccagcag     360
ggcccgcgcc aggccgccag cctcggagtg ggcgcgggac agtgcgcggc gccccgcagc     420
caggccccg ccccgccgc atccacctcc tccgccgcct cgacccaac gggcgccccc        480
cgccgcggca gctgccgccg ggccccgcg gccaccatga agaaggaggt gtgctccgtg       540
gccttcctca aggccgtgtt cgcagagttc ttggccaccc tcatcttcgt cttctttggc     600
ctgggctcgg ccctcaagtg gccgtcggcg ctgcctacca tcctgcagat cgcgctggcg     660
tttggcctgg ccataggcac gctggcccag gccctgggac ccgtgagcgg cggccacatc     720
aaccccgcca tcaccctggc cctcttggtg ggcaaccaga tctcgctgct ccgggctttc     780
ttctacgtgg cggcccagct ggtgggcgc attgccgggg ctggcatcct ctacggtgtg     840
gcaccgctca atgcccgggg caatctggcc gtcaacgcgc tcaacaacaa cacaacgcag     900
```

```
ggccaggcca tggtggtgga gctgattctg accttccagc tggcactctg catcttcgcc      960
tccactgact cccgccgcac cagccctgtg ggctccccag ccctgtccat tggcctgtct     1020
gtcaccctgg ccaccttgt cggaatctac ttcactggct gctccatgaa cccagcccgc     1080
tcttttggcc ctgcggtggt catgaatcgg ttcagccccg ctcactgggg tctgcttcta     1140
tccctgcgtg aggggacac gcgctctgtt catccgtctc tctgaggacc cacgtgtccc     1200
ctctgaaggt tttctgggta gggcccatcg tgggggcggt cctggctgcc atcctttact     1260
tctacctgct cttccccaac tccctgagcc tgagtgagcg tgtggccatc atcaaaggca     1320
cgtatgagcc tgacgaggac tgggaggagc agcgggaaga gcggaagaag accatggagc     1380
tgaccacccg ctgaccagtg tcaggcaggg ccagcccct cagcccctga gccaaggggg     1440
aaaagaagaa aaagtaccta acacaagctt ccttttttgca caaccggtcc tcttggctga     1500
ggaggaggag ctggtcaccc tggctgcaca gttagagagg ggagaaggaa cccatgatgg     1560
gactcctggg gtaggggcca ggggctgggg tctgctgggg acaggtctct ctgggacaga     1620
cctcagagat tgtgaatgca gtgccaagct cacaggctgc aagggccagg ccagaaaagg     1680
gtgggcctgc agcctgcacc ccccaccttc cccaacccttt cctcaagagc tgaagggatc     1740
ccagccccta ggtgggcaga ggcagaccct ccccagagct ccttaggaag aagacagact     1800
ggttcattga atgccgcctt atttatttct ggtgaggatg catgcgtggg gctgctggtg     1860
tttagagtgg gggctaccca ataaatcact gatactcaaa acaccagcag accctcccca     1920
gagctcctta ggaagaagac agactggttc attgaatgcc gccttattta tttctggtga     1980
ggatgcatgc gtggggctgc tggtgtttag agtggggct acccaataaa tcactgatac     2040
tcacattccg cctctgtctc tcctcagagt gccttgagac actctggccc attgcctctc     2100
ctctttgtca tcccacatcc tccaccacga tctccacagg gtaccagggg accccaggac     2160
aagtgctctg tgggaagaaa                                                2180
```

<210> SEQ ID NO 10
<211> LENGTH: 222
<212> TYPE: PRT
<213> ORGANISM: Homo sapiens

<400> SEQUENCE: 10

```
Met Lys Lys Glu Val Cys Ser Val Ala Phe Leu Lys Ala Val Phe Ala
 1               5                  10                  15

Glu Phe Leu Ala Thr Leu Ile Phe Val Phe Gly Leu Gly Ser Ala
            20                  25                  30

Leu Lys Trp Pro Ser Ala Leu Pro Thr Ile Leu Gln Ile Ala Leu Ala
        35                  40                  45

Phe Gly Leu Ala Ile Gly Thr Leu Ala Gln Ala Leu Gly Pro Val Ser
    50                  55                  60

Gly Gly His Ile Asn Pro Ala Ile Thr Leu Ala Leu Leu Val Gly Asn
65                  70                  75                  80

Gln Ile Ser Leu Leu Arg Ala Phe Phe Tyr Val Ala Ala Gln Leu Val
                85                  90                  95

Gly Ala Ile Ala Gly Ala Gly Ile Leu Tyr Gly Val Ala Pro Leu Asn
            100                 105                 110

Ala Arg Gly Asn Leu Ala Val Asn Ala Leu Asn Asn Asn Thr Thr Gln
        115                 120                 125

Gly Gln Ala Met Val Val Glu Leu Ile Leu Thr Phe Gln Leu Ala Leu
    130                 135                 140
```

```
Cys Ile Phe Ala Ser Thr Asp Ser Arg Arg Thr Ser Pro Val Gly Ser
145                 150                 155                 160

Pro Ala Leu Ser Ile Gly Leu Ser Val Thr Leu Gly His Leu Val Gly
            165                 170                 175

Ile Tyr Phe Thr Gly Cys Ser Met Asn Pro Ala Arg Ser Phe Gly Pro
        180                 185                 190

Ala Val Val Met Asn Arg Phe Ser Pro Ala His Trp Gly Leu Leu Leu
    195                 200                 205

Ser Leu Arg Gly Gly Asp Thr Arg Ser Val His Pro Ser Leu
    210                 215                 220
```

<210> SEQ ID NO 11
<211> LENGTH: 1051
<212> TYPE: DNA
<213> ORGANISM: Homo sapiens

<400> SEQUENCE: 11

```
cctaactcca ggccagactc cttagcaccc tcccctaact ccaggccaga ctcctttcag      60
ctaaaggggt ggaattcatg gcatctactt cgtatgacta ttgcagagtg cccatggaag    120
acggggataa gcgctgtaag cttctgctgg ggataggaat tctggtgctc ctgatcatcg    180
tgattctggg ggtgcccttg attatcttca ccatcaaggc caacagcgag gcctgccggg    240
acggccttcg ggcagtgatg gagtgtcgca atgtcaccca tctcctgcaa caagagctga    300
ccgaggccca aagggctttc aggatgtgg aggcccaggc cgccacctgc aaccacactg    360
tgatggccct aatggcttcc ctggatgcag agaaggccca aggacaaaag aaagtggagg    420
agcttgaggg agagatcact acattaaacc ataagcttca ggacgcgtct gcagaggtgg    480
agcgactgag aagagaaaac caggtcttaa gcgtgagaat cgcggacaag aagtactacc    540
ccagctccca ggactccagc tccgctgcgg cgccccagct gctgattgtg ctgctgggcc    600
tcagcgctct gctgcagtga gatcccagga agctggcaca tcttggaagg tccgtcctgc    660
tcggcttttc gcttgaacat tcccttgatc tcatcagttc tgagcgggtc atgggcaac    720
acggttagcg gggagagcac ggggtagccg agaagggcc tctggagcag gtctggaggg    780
gccatggggc agtcctgggt gtggggacac agtcgggttg acccagggct gtctccctcc    840
agagcctccc tccggacaat gagtcccccc tcttgtctcc caccctgaga ttgggcatgg    900
ggtgcggtgt gggggcatg tgctgcctgt tgttatgggt ttttttgcg gggggggttg    960
cttttttctg gggctcttga gctccaaaaa ataaacactt cctttgaggg agagcaaaaa   1020
aaaaaaaaaa aaaaaaaaa aaaaaaaaaa a                                    1051
```

<210> SEQ ID NO 12
<211> LENGTH: 180
<212> TYPE: PRT
<213> ORGANISM: Homo sapiens

<400> SEQUENCE: 12

```
Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
    50                  55                  60
```

| | | | | | | | | | | | | | | |
|---|---|---|---|---|---|---|---|---|---|---|---|---|---|---|
|Asn|Val|Thr|His|Leu|Leu|Gln|Gln|Glu|Leu|Thr|Glu|Ala|Lys|Gly|
|65| | | |70| | | |75| | | |80| | |

Phe Gln Asp Val Glu Ala Gln Ala Ala Thr Cys Asn His Thr Val Met
               85               90               95

Ala Leu Met Ala Ser Leu Asp Ala Glu Lys Ala Gln Gly Gln Lys Lys
           100              105             110

Val Glu Glu Leu Glu Gly Glu Ile Thr Thr Leu Asn His Lys Leu Gln
       115              120             125

Asp Ala Ser Ala Glu Val Glu Arg Leu Arg Arg Glu Asn Gln Val Leu
       130              135             140

Ser Val Arg Ile Ala Asp Lys Lys Tyr Tyr Pro Ser Ser Gln Asp Ser
145             150             155             160

Ser Ser Ala Ala Ala Pro Gln Leu Leu Ile Val Leu Leu Gly Leu Ser
       165              170             175

Ala Leu Leu Gln
       180

<210> SEQ ID NO 13
<211> LENGTH: 3445
<212> TYPE: DNA
<213> ORGANISM: Homo sapiens

<400> SEQUENCE: 13

```
gagcaaccgc agcttctagt atccagactc cagcgccgcc ccgggcgcgg accccaaccc      60
cgacccagag cttctccagc ggcggcgcag cgagcagggc tccccgcctt aacttcctcc     120
gcggggccca gccaccttcg ggagtccggg ttgcccacct gcaaactctc cgccttctgc     180
acctgccacc cctgagccag cgcggcgcc cgagcgagtc atggccaacg cggggctgca     240
gctgttgggc ttcattctcg ccttcctggg atggatcggc gccatcgtca gcactgccct     300
gccccagtgg aggatttact cctatgccgg cgacaacatc gtgaccgccc aggccatgta     360
cgagggggctg tggatgtcct gcgtgtcgca gagcaccggg cagatccagt gcaaagtctt     420
tgactccttg ctgaatctga gcagcacatt gcaagcaacc cgtgccttga tggtggttgg     480
catcctcctg ggagtgatag caatctttgt ggccaccgtt ggcatgaagt gtatgaagtg     540
cttggaagac gatgaggtgc agaagatgag gatggctgtc attggggggtg cgatatttct     600
tcttgcaggt ctggctattt tagttgccac agcatggtat ggcaatagaa tcgttcaaga     660
attctatgac cctatgaccc cagtcaatgc caggtacgaa tttggtcagg ctctcttcac     720
tggctgggct gctgcttctc tctgccttct gggaggtgcc ctactttgct gttcctgtcc     780
ccgaaaaaca acctcttacc caacaccaag gccctatcca aaacctgcac cttccagcgg     840
gaaagactac gtgtgacaca gaggcaaaag gagaaaatca tgttgaaaca aaccgaaaat     900
ggacattgag atactatcat taacattagg accttagaat tttgggtatt gtaatctgaa     960
gtatggtatt acaaaacaaa caaacaaaca aaaaacccat gtgttaaaat actcagtgct    1020
aaacatggct taatcttatt ttatcttctt tcctcaatat aggagggaag attttttccat    1080
ttgtattact gcttcccatt gagtaatcat actcaattgg gggaaggggt gctccttaaa    1140
tatatataga tatgtatata tacatgtttt tctattaaaa atagacagta aaatactatt    1200
ctcattatgt tgatactagc atacttaaaa tatctctaaa ataggtaaat gtatttaatt    1260
ccatattgat gaagatgttt attggtatat tttcttttc gtctatatat acatatgtaa    1320
cagtcaaata tcatttactc ttcttcatta gctttgggtg cctttgccac aagacctagc    1380
ctaatttacc aaggatgaat tctttcaatt cttcatgcgt gccctttca tatacttatt    1440
```

```
ttatttttta ccataatctt atagcacttg catcgttatt aagcccttat ttgttttgtg    1500
tttcattggt ctctatctcc tgaatctaac acatttcata gcctacattt tagtttctaa    1560
agccaagaag aatttattac aaatcagaac tttggaggca atctttctg catgaccaaa     1620 gtgataaatt cctgttgacc ttcccacaca atccctgtac tctgacccat agcactcttg    1680
tttgctttga aaatatttgt ccaattgagt agctgcatgc tgttccccca ggtgttgtaa    1740
cacaacttta ttgattgaat ttttaagcta cttattcata gttttatatc ccctaaact     1800 accttttgt tccccattcc ttaattgtat tgttttccca agtgtaatta tcatgcgttt    1860
tatatcttcc taataaggtg tggtctgttt gtctgaacaa agtgctagac tttctggagt    1920
gataatctgg tgacaaatat tctctctgta gctgtaagca agtcacttaa tctttctacc    1980
tcttttttct atctgccaaa ttgagataat gatacttaac cagttagaag aggtagtgtg    2040
aatattaatt agtttatatt actctcattc tttgaacatg aactatgcct atgtagtgtc    2100
tttatttgct cagctggctg agacactgaa gaagtcactg aacaaaacct acacacgtac    2160
cttcatgtga ttcactgcct tcctctctct accagtctat ttccactgaa caaaacctac    2220
acacatacct tcatgtggtt cagtgccttc ctctctctac cagtctattt ccactgaaca    2280
aaacctacgc atacccttc atgtggctca gtgccttcct ctctctacca gtctattcc     2340 attctttcag ctgtgtctga catgtttgtg ctctgttcca ttttaacaac tgctcttact    2400
tttccagtct gtacagaatg ctatttcact tgagcaagat gatgtaatgg aaagggtgtt    2460
ggcattggtg tctggagacc tggatttgag tcttggtgct atcaatcacc gtctgtgttt    2520
gagcaaggca tttggctgct gtaagcttat tgcttcatct gtaagcggtg gtttgtaatt    2580
cctgatcttc ccacctcaca gtgatgttgt ggggatccag tgagatagaa tacatgtaag    2640
tgtggttttg taatttaaaa agtgctatac taagggaaag aattgaggaa ttaactgcat    2700
acgttttggt gttgcttttc aaatgtttga aaacaaaaaa aatgttaaga aatgggtttc    2760
ttgccttaac cagtctctca agtgatgaga cagtgaagta aaattgagtg cactaaacaa    2820
ataagattct gaggaagtct tatcttctgc agtgagtatg gcccgatgct ttctgtggct    2880
aaacagatgt aatgggaaga aataaaagcc tacgtgttgg taaatccaac agcaagggag    2940
atttttgaat cataataact cataaggtgc tatctgttca gtgatgccct cagagctctt    3000
gctgttagct ggcagctgac gctgctagga tagttagttt ggaaatggta cttcataata    3060
aactacacaa ggaaagtcag ccactgtgtc ttatgaggaa ttggacctaa taaatttag     3120 tgtgccttcc aaacctgaga atatatgctt ttggaagtta aaatttaaat ggcttttgcc    3180
acatacatag atcttcatga tgtgtgagtg taattccatg tggatatcag ttaccaaaca    3240
ttacaaaaaa attttatggc ccaaaatgac caacgaaatt gttacaatag aatttatcca    3300
attttgatct ttttatattc ttctaccaca cctggaaaca gaccaataga cattttgggg    3360
ttttataata ggaatttgta taaagcatta ctcttttca ataaattgtt ttttaattta    3420 aaaaaggaa aaaaaaaaa aaaaa                                            3445
```

<210> SEQ ID NO 14
<211> LENGTH: 211
<212> TYPE: PRT
<213> ORGANISM: Homo sapiens

<400> SEQUENCE: 14

Met Ala Asn Ala Gly Leu Gln Leu Leu Gly Phe Ile Leu Ala Phe Leu
1               5                   10                  15

```
Gly Trp Ile Gly Ala Ile Val Ser Thr Ala Leu Pro Gln Trp Arg Ile
         20                  25                  30
Tyr Ser Tyr Ala Gly Asp Asn Ile Val Thr Ala Gln Ala Met Tyr Glu
         35                  40                  45
Gly Leu Trp Met Ser Cys Val Ser Gln Ser Thr Gly Gln Ile Gln Cys
         50                  55                  60
Lys Val Phe Asp Ser Leu Leu Asn Leu Ser Ser Thr Leu Gln Ala Thr
65                   70                  75                  80
Arg Ala Leu Met Val Val Gly Ile Leu Leu Gly Val Ile Ala Ile Phe
                 85                  90                  95
Val Ala Thr Val Gly Met Lys Cys Met Lys Cys Leu Glu Asp Asp Glu
                100                 105                 110
Val Gln Lys Met Arg Met Ala Val Ile Gly Gly Ala Ile Phe Leu Leu
                115                 120                 125
Ala Gly Leu Ala Ile Leu Val Ala Thr Ala Trp Tyr Gly Asn Arg Ile
        130                 135                 140
Val Gln Glu Phe Tyr Asp Pro Met Thr Pro Val Asn Ala Arg Tyr Glu
145                 150                 155                 160
Phe Gly Gln Ala Leu Phe Thr Gly Trp Ala Ala Ala Ser Leu Cys Leu
                165                 170                 175
Leu Gly Gly Ala Leu Leu Cys Cys Ser Cys Pro Arg Lys Thr Thr Ser
                180                 185                 190
Tyr Pro Thr Pro Arg Pro Tyr Pro Lys Pro Ala Pro Ser Ser Gly Lys
        195                 200                 205
Asp Tyr Val
        210

<210> SEQ ID NO 15
<211> LENGTH: 1850
<212> TYPE: DNA
<213> ORGANISM: Homo sapiens

<400> SEQUENCE: 15
cgcgctcgca gctcgcaggc gccgcgtagc cgtcgccacc gccgccagcc cgtgcgccct      60
cggcgcgtac ccgccgcgct cccatccccg ccgccggcca ggggcgcgct cggccgcccc     120
ggacagtgtc ccgctgcggc tccgcggcga tggccaccaa gatcgacaaa gaggcttgcc     180
gggcggcgta caacctggtg cgcgacgacg gctcggccgt catctgggtg acttttaaat     240
atgacggctc caccatcgtc cccggcgagc agggagcgga gtaccagcac ttcatccagc     300
agtgcacaga tgacgtccgg ttgtttgcct tcgtgcgctt caccaccggg gatgccatga     360
gcaagaggtc caagtttgcc ctcatcacgt ggatcggtga aacgtcagc gggctgcagc      420 gcgccaaaac cgggacggac aagaccctgg tgaaggaggt cgtacagaat ttcgctaagg     480
agtttgtgat cagtgatcgg aaggagctgg aggaagattt catcaagagc gagctgaaga     540 aggcggggggg agccaattac gacgcccaga cggagtaacc ccagccccg ccacaccacc     600 ccttgccaaa gtcatctgcc tgctccccgg gggagaggac cgccggcctc agctactagc     660
ccaccagccc accagggaga aagaagcca tgagaggcag cgcccgccac cctgtgtcca     720 cagccccccac cttccgcctt cccttagaac cctgccgtgt cctatctcat gacgctcatg     780
gaacctcttt ctttgatctt ctttttcttt tctcccccctc ttttttgttc taaagaaaag     840
tcattttgat gcaaggtcct gcctgccatc agatccgagg tgcctcctgc agtgaccct      900 tttcctggca tttctcttcc acgcgacgag gtctgcctag tgagatctgc atgacctcac     960
```

-continued

```
gttgctttcc agagcccggg cctatttgc catctcagtt ttcctggacc ctgcttcctg      1020
tgtaccactg aggggcagct gggccaggag ctgtgcccgg tgcctgcagc cttcataagc      1080
acacacgtcc attccctact aaggcccaga cctcctggta tctgcccggg gctccctcat      1140
cccacctcca tccggagttg cctaagatgc atgtccagca taggcaggat tgctcggtgg      1200
tgagaaggtt aggtccggct cagactgaat aagaagagat aaaatttgcc ttaaaactta      1260
cctggcagtg gctttgctgc acggtctgaa accacctgtt cccaccctct tgaccgaaat      1320
ttccttgtga cacagagaag ggcaaaggtc tgagcccaga gttgacggag ggagtatttc      1380
agggttcact tcaggggctc ccaaagcgac aagatcgtta gggagagagg cccagggtgg      1440
ggactgggaa tttaaggaga gctgggaacg gatcccttag gttcaggaag cttctgtgta      1500
agctgcgagg atggcttggg ccgaagggtt gctctgcccg ccgcgctagc tgtgagctga      1560
gcaaagccct gggctcacag caccccaaaa gcctgtggct tcagtcctgc gtctgcacca      1620
cacattcaaa aggatcgttt tgttttgttt ttaaagaaag gtgagattgg cttggttctt      1680
catgagcaca tttgatatag ctcttttct gttttccttt gctcatttcg tttgggaa         1740 gaaatctgta ctgtattggg attgtaaaga acatctctgc actcagacag tttacagaaa      1800
taaatgtttt ttttgttttt cagaaaaaaa aaaaaaaaaa aaaaaaaaaa                 1850
```

```
<210> SEQ ID NO 16
<211> LENGTH: 142
<212> TYPE: PRT
<213> ORGANISM: Homo sapiens

<400> SEQUENCE: 16

Met Ala Thr Lys Ile Asp Lys Glu Ala Cys Arg Ala Ala Tyr Asn Leu
1               5                   10                  15

Val Arg Asp Asp Gly Ser Ala Val Ile Trp Val Thr Phe Lys Tyr Asp
            20                  25                  30

Gly Ser Thr Ile Val Pro Gly Glu Gln Gly Ala Glu Tyr Gln His Phe
        35                  40                  45

Ile Gln Gln Cys Thr Asp Val Arg Leu Phe Ala Phe Val Arg Phe
    50                  55                  60

Thr Thr Gly Asp Ala Met Ser Lys Arg Ser Lys Phe Ala Leu Ile Thr
65                  70                  75                  80

Trp Ile Gly Glu Asn Val Ser Gly Leu Gln Arg Ala Lys Thr Gly Thr
                85                  90                  95

Asp Lys Thr Leu Val Lys Glu Val Val Gln Asn Phe Ala Lys Glu Phe
            100                 105                 110

Val Ile Ser Asp Arg Lys Glu Leu Glu Glu Asp Phe Ile Lys Ser Glu
        115                 120                 125

Leu Lys Lys Ala Gly Gly Ala Asn Tyr Asp Ala Gln Thr Glu
    130                 135                 140
```

```
<210> SEQ ID NO 17
<211> LENGTH: 662
<212> TYPE: DNA
<213> ORGANISM: Homo sapiens

<400> SEQUENCE: 17
acacatccaa gcttaagacg gtgaggtcag cttcacattc tcaggaactc tccttctttg      60
ggtctagctg aagttgagga tctcttactc tctaagccac ggaattaacc cgagcaggca     120
tggaggcctc tgctctcacc tcatcagcag tgaccagtgt ggccaaagtg gtcagggtgg     180
```

```
cctctggctc tgccgtagtt ttgcccctgg ccaggattgc tacagttgtg attggaggag    240
ttgtggccat ggcggctgtg cccatggtgc tcagtgccat gggcttcact gcggcgggaa    300
tcgcctcgtc ctccatagca gccaagatga tgtccgcggc ggccattgcc aatgggggtg    360
gagttgcctc gggcagcctt gtgggtactc tgcagtcact gggagcaact ggactctccg    420
gattgaccaa gttcatcctg gctccattg gtctgccat tgcggctgtc attgcgaggt      480
tctactagct ccctgcccct cgccctgcag agaagagaac catgccaggg agaaggcac     540 ccagccatcc tgacccagcg aggagccaac tatcccaaat atacctgggt gaaatatacc    600
aaattctgca tctccagagg aaaataagaa ataaagatga attgttgcaa ctcttaaaaa    660
aa                                                                   662
```

```
<210> SEQ ID NO 18
<211> LENGTH: 122
<212> TYPE: PRT
<213> ORGANISM: Homo sapiens

<400> SEQUENCE: 18

Met Glu Ala Ser Ala Leu Thr Ser Ser Ala Val Thr Ser Val Ala Lys
 1               5                  10                  15

Val Val Arg Val Ala Ser Gly Ser Ala Val Val Leu Pro Leu Ala Arg
             20                  25                  30

Ile Ala Thr Val Val Ile Gly Gly Val Val Ala Met Ala Ala Val Pro
         35                  40                  45

Met Val Leu Ser Ala Met Gly Phe Thr Ala Ala Gly Ile Ala Ser Ser
     50                  55                  60

Ser Ile Ala Ala Lys Met Met Ser Ala Ala Ile Ala Asn Gly Gly
 65                  70                  75                  80

Gly Val Ala Ser Gly Ser Leu Val Gly Thr Leu Gln Ser Leu Gly Ala
             85                  90                  95

Thr Gly Leu Ser Gly Leu Thr Lys Phe Ile Leu Gly Ser Ile Gly Ser
            100                 105                 110

Ala Ile Ala Ala Val Ile Ala Arg Phe Tyr
            115                 120
```

```
<210> SEQ ID NO 19
<211> LENGTH: 653
<212> TYPE: DNA
<213> ORGANISM: Homo sapiens

<400> SEQUENCE: 19
acacatccaa gcttaagacg gtgaggtcag cttcacattc tcaggaactc tccttctttg    60
ggtctagctg aagttgagga tctcttactc tctaagccac ggaattaacc cgagcaggca    120
tggaggcctc tgctctcacc tcatcagcag tgaccagtgt ggccaaagtg gtcagggtgg    180
cctctggctc tgccgtagtt ttgcccctgg ccaggattgc tacagttgtg attggaggag    240
ttgtggctgt gccatggtg ctcagtgcca tgggcttcac tgcggcggga atcgcctcgt     300
cctccatagc agccaagatg atgtccgcgg cggccattgc caatgggggt ggagttgcct    360
cgggcagcct tgtggctact ctgcagtcac tgggagcaac tggactctcc ggattgacca    420
agttcatcct gggctccatt gggtctgcca ttgcggctgt cattgcgagg ttctactagc    480
tccctgcccc tcgccctgca gagaagagaa ccatgccagg ggagaaggca cccagccatc    540
ctgacccagc gaggagccaa ctatcccaaa tatacctggg tgaaatatac caaattctgc    600
```

-continued atctccagag gaaaataaga aataaagatg aattgttgca actcttaaaa aaa         653

<210> SEQ ID NO 20
<211> LENGTH: 119
<212> TYPE: PRT
<213> ORGANISM: Homo sapiens

<400> SEQUENCE: 20

Met Glu Ala Ser Ala Leu Thr Ser Ser Ala Val Thr Ser Val Ala Lys
 1               5                  10                  15

Val Val Arg Val Ala Ser Gly Ser Ala Val Val Leu Pro Leu Ala Arg
            20                  25                  30

Ile Ala Thr Val Val Ile Gly Gly Val Val Ala Val Pro Met Val Leu
        35                  40                  45

Ser Ala Met Gly Phe Thr Ala Ala Gly Ile Ala Ser Ser Ile Ala
    50                  55                  60

Ala Lys Met Met Ser Ala Ala Ala Ile Ala Asn Gly Gly Val Ala
65                  70                  75                  80

Ser Gly Ser Leu Val Ala Thr Leu Gln Ser Leu Gly Ala Thr Gly Leu
                85                  90                  95

Ser Gly Leu Thr Lys Phe Ile Leu Gly Ser Ile Gly Ser Ala Ile Ala
            100                 105                 110

Ala Val Ile Ala Arg Phe Tyr
        115

<210> SEQ ID NO 21
<211> LENGTH: 4755
<212> TYPE: DNA
<213> ORGANISM: Homo sapiens

<400> SEQUENCE: 21
gccgggggac ccctccctcc tgtcctcctt gcggtcgacc ggtgcgcttg ccagatccgc         60
cgcgaagccg ggatcgaagg cgacagcgcg gccaaggggg cgcggccggg acaagctggg        120
ggccggttgc ccggggcagg gacggcggcg acccggccgc tggggaggca ggaagataga        180
cccacggatc ttaggaaggg atccgagagc gcagccgcgc gccccgcgcc ccacgcctga        240
tgctctgtgc gctcgccttg atggtggcgg ccggcggctg cgtcgtctcc gccttcaacc        300
tggatacccg attcctggta gtgaaggagg ccgggaaccc gggcagcctc ttcggctact        360
cggtcgccct ccatcggcag acagagcggc agcagcgcta cctgctcctg gctggtgccc        420
cccgggagct cgctgtgccc gatggctaca ccaaccggac tggtgctgtg tacctgtgcc        480
cactcactgc ccacaaggat gactgtgagc ggatgaacat cacagtgaaa aatgaccctg        540
gccatcacat tattgaggac atgtggcttg gagtgactgt ggccagccag ggccctgcag        600
gcagagttct ggtctgtgcc caccgctaca cccaggtgct gtggtcaggg tcagaagacc        660
agcggcgcat ggtgggcaag tgctacgtgc gaggcaatga cctagagctg gactccagtg        720
atgactggca gacctaccac aacgagatgt gcaatagcaa cacagactac ctggagacgg        780
gcatgtgcca gctgggcacc agcggtggct tcacccagaa cactgtgtac ttcggcgccc        840
ccggtgccta caactggaaa ggaaacagct acatgattca gcgcaaggag tgggacttat        900
ctgagtatag ttacaaggac ccagaggacc aaggaaacct ctatattggg tacacgatgc        960
aggtaggcag cttcatcctg cacccaaaaa acatcaccat tgtgacaggt gccccacggc       1020
accgacatat gggcgcggtg ttcttgctga gccaggaggc aggcggagac ctgcggagga       1080
ggcaggtgct ggagggctcg caggtgggcg cctatttttgg cagcgccatt gccctggcag       1140

```
acctgaacaa tgatgggtgg caggacctcc tggtgggcgc ccctactac ttcgagagga    1200 aagaggaagt aggggggtgcc atctatgtct tcatgaacca ggcgggaacc tccttccctg    1260
ctcacccctc actccttctt catggcccca gtggctctgc ctttggttta tctgtggcca    1320
gcattggtga catcaaccag gatggatttc aggatattgc tgtgggagct ccgtttgaag    1380
gcttgggcaa agtgtacatc tatcacagta gctctaaggg gctccttaga cagccccagc    1440
aggtaatcca tggagagaag ctgggactgc ctgggttggc caccttcggc tattccctca    1500
gtgggcagat ggatgtggat gagaacttct acccagacct tctagtggga agcctgtcag    1560
accacattgt gctgctgcgg gcccggcccg tcatcaacat cgtccacaag accttggtgc    1620
ccaggccagc tgtgctggac cctgcacttt gcacggccac ctcttgtgtg caagtggagc    1680
tgtgctttgc ttacaaccag agtgccggga accccaacta caggcgaaac atcaccctgg    1740
cctacactct ggaggctgac agggaccgcc ggccgccccg gctccgcttt gccggcagtg    1800
agtccgctgt cttccacggc ttcttctcca tgcccgagat gcgctgccag aagctggagc    1860
tgctcctgat ggacaacctc cgtgacaaac tccgccccat catcatctcc atgaactact    1920
ctttaccttt gcggatgccc gatcgccccc ggctggggct gcggtccctg gacgcctacc    1980
cgatcctcaa ccaggcacag gctctggaga accacactga ggtccagttc cagaaggagt    2040
gcgggcctga caacaagtgt gagagcaact tgcagatgcg ggcagccttc gtgtcagagc    2100
agcagcagaa gctgagcagg ctccagtaca gcagagacgt ccggaaattg ctcctgagca    2160
tcaacgtgac gaacacccgg acctcggagc gctccgggga ggacgccac gaggcgctgc    2220 tcaccctggt ggtgcctccc gccctgctgc tgtcctcagt gcgcccccc ggggcctgcc    2280 aagctaatga gaccatcttt tgcgagctgg ggaaccccctt caaacggaac cagaggatgg    2340
agctgctcat cgcctttgag gtcatcgggg tgaccctgca cacaagggac cttcaggtgc    2400
agctgcagct ctccacgtcg agtcaccagg acaaacctgtg gcccatgatc ctcactctgc    2460
tggtggacta tacactccag acctcgctta gcatggtaaa tcaccggcta caaagcttct    2520 ttgggggggac agtgatgggt gagtctggca tgaaaactgt ggaggatgta ggaagccccc    2580
tcaagtatga attccaggtg ggcccaatgg gggaggggct ggtgggcctg ggaccctgg    2640 tcctaggtct ggagtggccc tacgaagtca gcaatgcaa gtggctgctg tatcccacgg    2700
agatcaccgt ccatggcaat gggtcctggc cctgccgacc acctggagac cttatcaacc    2760
ctctcaacct cactctttct gaccctgggg acaggccatc atccccacag cgcaggcggc    2820
gacagctgga tccagggga ggccagggcc ccccaccgt cactctggct gctgccaaaa    2880
aagccaagtc tgagactgtg ctgacctgtg ccacagggcg tgcccactgt gtgtggctag    2940
agtgccccat ccctgatgcc cccgttgtca ccaacgtgac tgtgaaggca cgagtgtgga    3000
acagcacctt catcgaggat tacagagact ttgaccgagt ccgggtaaat ggctgggcta    3060
ccctattcct ccgaaccagc atccccacca tcaacatgga gaacaagacc acgtggttct    3120
ctgtggacat tgactcggag ctggtggagg agctgccggc cgaaatcgag ctgtggctgg    3180
tgctggtggc cgtgggtgca gggctgctgc tgctggggct gatcatcctc ctgctgtgga    3240
agtgcggctt cttcaagcga gcccgcactc gcgccctgta tgaagctaag aggcagaagg    3300
cggagatgaa gagccagccg tcagagacag agaggctgac cgacgactac tgaggggggca    3360 gccccccgcc ccggcccac ctggtgtgac ttctttaagc ggaccgcta ttatcagatc    3420 atgcccaagt accacgcagt gcggatccgg gaggaggagc gctacccacc tccagggagc    3480
```

-continued

```
acctgccca ccaagaagca ctgggtgacc agctggcaga ctcgggacca atactactga    3540
cgtcctccct gatcccaccc cctcctcccc cagtgtcccc tttcttccta tttatcataa    3600
gttatgcctc tgacagtcca caggggccac cacctttggc tggtagcagc aggctcaggc    3660
acatacacct cgtcaagagc atgcacatgc tgtctggccc tggggatctt cccacaggag    3720
ggccagcgct gtggacctta caacgccgag tgcactgcat tcctgtgccc tagatgcacg    3780
tggggcccac tgctcgtgga ctgtgctggt gcatcacgga tggtgcatgg gctcgccgtg    3840
tctcagcctc tgccagcgcc aaaacaagcc aaagagcctc ccaccagagc cgggaggaaa    3900
aggcccctgc aatgtggtga cacctccccc tttcacactg gatccatctt gagccacagt    3960
cactggattg actttgctgt caaaactact gacagggagc agcccccggg ccgctggctg    4020
gtgggccccc aatgacaccc atgccagaga ggtggggatc ctgcctaagg ttgtctacgg    4080
gggcacttgg aggacctggc gtgctcagac ccaacagcaa aggaactaga agaaggacc    4140 cagaacggct tgctttcctg catctctgtg aagcctctct ccttggccac agactgaact    4200
cgcagggaat gcagcaggaa ggaacaaaga caggcaaacg caacgtagc ctgggctcac    4260 tgtgctgggg cacggcggga tcctccacag agaggagggg accaattctg gacagacaga    4320
tgttgggagg atacagagga gatgccactt ctcactcacc actaccagcc agcctcagaa    4380
ggccccagag agaccctgca agaccacgga gggagcgaca cttgaatgta gaataggcag    4440
ggggccctgc cccacccat ccagccagac cccacgctga ccatgcgtca ggggcctaga    4500
ggtggagttc ttagctatcc ttggctttca gagccagcct ggctctgccc cctccccat    4560 gggctgtgtc ctaaggccca tttgagaagc tgaggctagt tccagaaaac ctctcctgac    4620
ccctgcctgt tggcaggccc actcccagc cccagcccct tccatggtac tgtagcaggg    4680
gaattccctc cccctccttg tgccttcttt gtatataggc ttctcacggc gaccaataaa    4740
cagctcccag tttgt                                                      4755
```

<210> SEQ ID NO 22
<211> LENGTH: 1037
<212> TYPE: PRT
<213> ORGANISM: Homo sapiens

<400> SEQUENCE: 22

```
Met Leu Cys Ala Leu Ala Leu Met Val Ala Ala Gly Gly Cys Val Val
  1               5                  10                  15

Ser Ala Phe Asn Leu Asp Thr Arg Phe Leu Val Val Lys Glu Ala Gly
             20                  25                  30

Asn Pro Gly Ser Leu Phe Gly Tyr Ser Val Ala Leu His Arg Gln Thr
         35                  40                  45

Glu Arg Gln Gln Arg Tyr Leu Leu Leu Ala Gly Ala Pro Arg Glu Leu
     50                  55                  60

Ala Val Pro Asp Gly Tyr Thr Asn Arg Thr Gly Ala Val Tyr Leu Cys
 65                  70                  75                  80

Pro Leu Thr Ala His Lys Asp Asp Cys Glu Arg Met Asn Ile Thr Val
                 85                  90                  95

Lys Asn Asp Pro Gly His His Ile Ile Glu Asp Met Trp Leu Gly Val
            100                 105                 110

Thr Val Ala Ser Gln Gly Pro Ala Gly Arg Val Leu Val Cys Ala His
        115                 120                 125

Arg Tyr Thr Gln Val Leu Trp Ser Gly Ser Glu Asp Gln Arg Arg Met
    130                 135                 140
```

-continued

```
Val Gly Lys Cys Tyr Val Arg Gly Asn Asp Leu Glu Leu Asp Ser Ser
145                 150                 155                 160

Asp Asp Trp Gln Thr Tyr His Asn Glu Met Cys Asn Ser Asn Thr Asp
                165                 170                 175

Tyr Leu Glu Thr Gly Met Cys Gln Leu Gly Thr Ser Gly Gly Phe Thr
            180                 185                 190

Gln Asn Thr Val Tyr Phe Gly Ala Pro Gly Ala Tyr Asn Trp Lys Gly
        195                 200                 205

Asn Ser Tyr Met Ile Gln Arg Lys Glu Trp Asp Leu Ser Glu Tyr Ser
210                 215                 220

Tyr Lys Asp Pro Glu Asp Gln Gly Asn Leu Tyr Ile Gly Tyr Thr Met
225                 230                 235                 240

Gln Val Gly Ser Phe Ile Leu His Pro Lys Asn Ile Thr Ile Val Thr
                245                 250                 255

Gly Ala Pro Arg His Arg His Met Gly Ala Val Phe Leu Leu Ser Gln
            260                 265                 270

Glu Ala Gly Gly Asp Leu Arg Arg Gln Val Leu Glu Gly Ser Gln
        275                 280                 285

Val Gly Ala Tyr Phe Gly Ser Ala Ile Ala Leu Ala Asp Leu Asn Asn
290                 295                 300

Asp Gly Trp Gln Asp Leu Leu Val Gly Ala Pro Tyr Tyr Phe Glu Arg
305                 310                 315                 320

Lys Glu Glu Val Gly Gly Ala Ile Tyr Val Phe Met Asn Gln Ala Gly
                325                 330                 335

Thr Ser Phe Pro Ala His Pro Ser Leu Leu His Gly Pro Ser Gly
            340                 345                 350

Ser Ala Phe Gly Leu Ser Val Ala Ser Ile Gly Asp Ile Asn Gln Asp
        355                 360                 365

Gly Phe Gln Asp Ile Ala Val Gly Ala Pro Phe Glu Gly Leu Gly Lys
    370                 375                 380

Val Tyr Ile Tyr His Ser Ser Lys Gly Leu Leu Arg Gln Pro Gln
385                 390                 395                 400

Gln Val Ile His Gly Glu Lys Leu Gly Leu Pro Gly Leu Ala Thr Phe
                405                 410                 415

Gly Tyr Ser Leu Ser Gly Gln Met Asp Val Asp Glu Asn Phe Tyr Pro
            420                 425                 430

Asp Leu Leu Val Gly Ser Leu Ser Asp His Ile Val Leu Leu Arg Ala
        435                 440                 445

Arg Pro Val Ile Asn Ile Val His Lys Thr Leu Val Pro Arg Pro Ala
    450                 455                 460

Val Leu Asp Pro Ala Leu Cys Thr Ala Thr Ser Cys Val Gln Val Glu
465                 470                 475                 480

Leu Cys Phe Ala Tyr Asn Gln Ser Ala Gly Asn Pro Asn Tyr Arg Arg
                485                 490                 495

Asn Ile Thr Leu Ala Tyr Thr Leu Glu Ala Asp Arg Asp Arg Arg Pro
            500                 505                 510

Pro Arg Leu Arg Phe Ala Gly Ser Glu Ser Ala Val Phe His Gly Phe
        515                 520                 525

Phe Ser Met Pro Glu Met Arg Cys Gln Lys Leu Glu Leu Leu Leu Met
    530                 535                 540

Asp Asn Leu Arg Asp Lys Leu Arg Pro Ile Ile Ile Ser Met Asn Tyr
545                 550                 555                 560

Ser Leu Pro Leu Arg Met Pro Asp Arg Pro Arg Leu Gly Leu Arg Ser
```

-continued

```
                565                 570                 575
Leu Asp Ala Tyr Pro Ile Leu Asn Gln Ala Gln Ala Leu Glu Asn His
            580                 585                 590

Thr Glu Val Gln Phe Gln Lys Glu Cys Gly Pro Asp Asn Lys Cys Glu
            595                 600                 605

Ser Asn Leu Gln Met Arg Ala Ala Phe Val Ser Glu Gln Gln Gln Lys
            610                 615                 620

Leu Ser Arg Leu Gln Tyr Ser Arg Asp Val Arg Lys Leu Leu Leu Ser
625                 630                 635                 640

Ile Asn Val Thr Asn Thr Arg Thr Ser Glu Arg Ser Gly Glu Asp Ala
                645                 650                 655

His Glu Ala Leu Leu Thr Leu Val Val Pro Ala Leu Leu Leu Ser
            660                 665                 670

Ser Val Arg Pro Pro Gly Ala Cys Gln Ala Asn Glu Thr Ile Phe Cys
            675                 680                 685

Glu Leu Gly Asn Pro Phe Lys Arg Asn Gln Arg Met Glu Leu Leu Ile
            690                 695                 700

Ala Phe Glu Val Ile Gly Val Thr Leu His Thr Arg Asp Leu Gln Val
705                 710                 715                 720

Gln Leu Gln Leu Ser Thr Ser Ser His Gln Asp Asn Leu Trp Pro Met
                725                 730                 735

Ile Leu Thr Leu Leu Val Asp Tyr Thr Leu Gln Thr Ser Leu Ser Met
                740                 745                 750

Val Asn His Arg Leu Gln Ser Phe Phe Gly Thr Val Met Gly Glu
            755                 760                 765

Ser Gly Met Lys Thr Val Glu Asp Val Gly Ser Pro Leu Lys Tyr Glu
            770                 775                 780

Phe Gln Val Gly Pro Met Gly Glu Gly Leu Val Gly Leu Gly Thr Leu
785                 790                 795                 800

Val Leu Gly Leu Glu Trp Pro Tyr Glu Val Ser Asn Gly Lys Trp Leu
                805                 810                 815

Leu Tyr Pro Thr Glu Ile Thr Val His Gly Asn Gly Ser Trp Pro Cys
            820                 825                 830

Arg Pro Pro Gly Asp Leu Ile Asn Pro Leu Asn Leu Thr Leu Ser Asp
            835                 840                 845

Pro Gly Asp Arg Pro Ser Ser Pro Gln Arg Arg Arg Gln Leu Asp
            850                 855                 860

Pro Gly Gly Gly Gln Gly Pro Pro Val Thr Leu Ala Ala Ala Lys
865                 870                 875                 880

Lys Ala Lys Ser Glu Thr Val Leu Thr Cys Ala Thr Gly Arg Ala His
                885                 890                 895

Cys Val Trp Leu Glu Cys Pro Ile Pro Asp Ala Pro Val Val Thr Asn
            900                 905                 910

Val Thr Val Lys Ala Arg Val Trp Asn Ser Thr Phe Ile Glu Asp Tyr
            915                 920                 925

Arg Asp Phe Asp Arg Val Arg Val Asn Gly Trp Ala Thr Leu Phe Leu
            930                 935                 940

Arg Thr Ser Ile Pro Thr Ile Asn Met Glu Asn Lys Thr Thr Trp Phe
945                 950                 955                 960

Ser Val Asp Ile Asp Ser Glu Leu Val Glu Leu Pro Ala Glu Ile
                965                 970                 975

Glu Leu Trp Leu Val Leu Val Ala Val Gly Ala Gly Leu Leu Leu Leu
            980                 985                 990
```

Gly Leu Ile Ile Leu Leu Leu Trp Lys Cys Gly Phe Phe Lys Arg Ala
        995                 1000                1005

Arg Thr Arg Ala Leu Tyr Glu Ala Lys Arg Gln Lys Ala Glu Met Lys
    1010                1015                1020

Ser Gln Pro Ser Glu Thr Glu Arg Leu Thr Asp Asp Tyr
1025                1030                1035

<210> SEQ ID NO 23
<211> LENGTH: 4647
<212> TYPE: DNA
<213> ORGANISM: Homo sapiens

<400> SEQUENCE: 23

| | | | | | |
|---|---|---|---|---|---|
| gtagcctctg | ttttcatttc | agtcttaatg | aaaactttct | aacttatatc | tcaagtttct | 60 |
| tttcaaagca | gtgtaagtag | tatttaaaat | gttatacttc | aagaaagaaa | gactttaacg | 120 |
| atattcagcg | ttggtcttgt | aacgctgaag | gtaattcatt | ttttaatcgg | tctgcacagc | 180 |
| aagaactgaa | acgaatgggg | attgaactgc | tttgcctgtt | ctttctattt | ctaggaagga | 240 |
| atgatcacgt | acaaggtggc | tgtgccctgg | gaggtgcaga | aacctgtgaa | gactgcctgc | 300 |
| ttattggacc | tcagtgtgcc | tggtgtgctc | aggagaattt | tactcatcca | tctggagttg | 360 |
| gcgaaaggtg | tgataccccca | gcaaaccttt | tagctaaagg | atgtcaatta | aacttcatcg | 420 |
| aaaaccctgt | ctcccaagta | gaaatactta | aaaataagcc | tctcagtgta | ggcagacaga | 480 |
| aaaatagttc | tgacattgtt | cagattgcgc | ctcaaagctt | gatccttaag | ttgagaccag | 540 |
| gtggtgcgca | gactctgcag | gtgcatgtcc | gccagactga | ggactacccg | gtggatttgt | 600 |
| attacctcat | ggacctctcc | gcctccatgg | atgacgacct | caacacaata | aaggagctgg | 660 |
| gctcccggct | ttccaaagag | atgtctaaat | taaccagcaa | ctttagactg | ggcttcggat | 720 |
| cttttgtgga | aaaacctgta | tccccttttcg | tgaaaacaac | accagaagaa | attgccaacc | 780 |
| cttgcagtag | tattccatac | ttctgtttac | ctacatttgg | attcaagcac | attttgccat | 840 |
| tgacaaatga | tgctgaaaga | ttcaatgaaa | ttgtgaagaa | tcagaaaatt | tctgctaata | 900 |
| ttgacacacc | cgaaggtgga | tttgatgcaa | ttatgcaagc | tgctgtgtgt | aaggaaaaaa | 960 |
| ttggctggcg | gaatgactcc | ctccacctcc | tggtctttgt | gagtgatgct | gattctcatt | 1020 |
| ttggaatgga | cagcaaacta | gcaggcatcg | tcattcctaa | tgacgggctc | tgtcacttgg | 1080 |
| acagcaagaa | tgaatactcc | atgtcaactg | tcttggaata | tccaacaatt | ggacaactca | 1140 |
| ttgataaact | ggtacaaaac | aacgtgttat | tgatcttcgc | tgtaacccaa | gaacaagttc | 1200 |
| atttatatga | aattacgca | aaacttattc | ctggagctac | agtaggtcta | cttcagaagg | 1260 |
| actccggaaa | cattctccag | ctgatcatct | cagcttatga | agaactgcgg | tctgaggtgg | 1320 |
| aactggaagt | attaggagac | actgaaggac | tcaacttgtc | atttacagcc | atctgtaaca | 1380 |
| acggtacccct | cttccaacac | caaaagaaat | gctctcacat | gaaagtggga | gacacagctt | 1440 |
| ccttcagcgt | gactgtgaat | atcccacact | gcgagagaag | aagcaggcac | attatcataa | 1500 |
| agcctgtggg | gctgggggat | gccctggaat | tacttgtcag | cccagaatgc | aactgcgact | 1560 |
| gtcagaaaga | agtggaagtg | aacagctcca | atgtcaccca | cggaacggc | tctttccagt | 1620 |
| gtgggggtgtg | tgcctgccac | cctggccaca | tggggcctcg | ctgtgagtgt | ggcgaggaca | 1680 |
| tgctgagcac | agattcctgc | aaggaggccc | cagatcatcc | ctcctgcagc | ggaagggtg | 1740 |
| actgctactg | tgggcagtgt | atctgccact | tgtctcccta | tggaaacatt | tatgggcctt | 1800 |
| attgccagtg | tgacaatttc | tcctgcgtga | gacacaaagg | gctgctctgc | ggaggtaacg | 1860 |

```
gcgactgtga ctgtggtgaa tgtgtgtgca ggagcggctg gactggcgag tactgcaact    1920
gcaccaccag cacggactcc tgcgtctctg aagatggagt gctctgcagc gggcgcgggg    1980
actgtgtttg tggcaagtgt gtttgcacaa accctggagc ctcaggacca acctgtgaac    2040
gatgtcctac ctgtggtgac ccctgtaact ctaaacggag ctgcattgag tgccacctgt    2100
cagcagctgg ccaagcccga gaagaatgtg tggacaagtg caaactagct ggtgcgacca    2160
tcagtgaaga agaagatttc tcaaaggatg gttctgtttc ctgctctctg caaggagaaa    2220
atgaatgtct tattacattc ctaataacta cagataatga ggggaaaacc atcattcaca    2280
gcatcaatga aaagattgt ccgaagcctc caaacattcc catgatcatg ttagggtttt     2340
ccctggctat tcttctcatc ggggttgtcc tactgtgcat ctggaagcta ctggtgtcat    2400
ttcatgatcg taaagaagtt gccaaatttg aagcagaacg atcaaaagcc aagtggcaaa    2460
cgggaaccaa tccactctac agaggatcca caagtacttt taaaaatgta acttataaac    2520
acagggaaaa acaaaaggta gacctttcca cagattgcta gaactacttt atgcatgaaa    2580
aaagtctgtt tcactgatat gaaatgttaa tgcactattt aattttttc tctttgttgc     2640 ttcaaaatga ggttggttta agataataat aggacatctg cagataagtc atcctctaca    2700
tgaaggtgac agactgttgg cagtttcaaa ataatcaaga agagaaatat ccttagcaaa    2760
gagatgactt tggggatcat ttgaggaata ctaactctgt tgcattaatg cttcaaaaaa    2820
tcatcaaatg attcatgggg gcctgatttg catttgaaaa atgttgaaa ttagagtctc     2880 atttgtttca ggaatgcagc tacctgagtt ttttgtctcg gcaaagtcac aaagcccata    2940
tactcacatt gtgtgtctat acttgccaat taattctaaa cttgtaggaa atatgccctc    3000
tcttaaagga gaattttttt taaatctctg agaaatgaga ttctgagttt atttcagcta    3060
aaaggttgca attcttctga agatatctca aatataaggt tgaaagttaa gtgttaataa    3120 ttttttgtgaa tttatacaca cctaaacgtt aagtacacaa atatttttatt tgttttacaa  3180 ataaggaata agtaatttat aaattaagaa gttacctata aaaataaaaa gataacaacc    3240
ctatcatata gcttattttt aaattacctg aaaaacgata ttctacactg tttccttttt    3300
gactctgagt tttcaaactg ttacttctcc catatttctc aatccatttc actcagttgc    3360
acagtctttt aaaccctgta attgtcatac caaagtttct ttttaaaaaa aaattacttt    3420
aaatgcttag tttattcaaa gagcgatcca ataatataaa aggaacatgt gttaaacaca    3480
ataaaatttt aaatggctct aaatcaagca catcaagagt atacaagtct taaaggcttt    3540
ttaatacata ctcttttccc atctatgtaa cccaacttgc acatttcagc tgcatgtggt    3600
gaatatgcat catatattta ctttaagagg taagatttta cttgcaaaat acatgtgcaa    3660
attaggatcc atcagttgat ggaagagatg gactctagaa tattatttct tgtggttatt    3720
actcctttac aaagcacttt cgtctcactt gatcctcata aggaaactaa ggctcagaat    3780
gagtagagct gggttcagaa tctagctctt ctaactccaa gccatctcct ctttccactg    3840
caggaaactg cctctttttgt cagtgaaata atagaaagat tgtgttagtt aagtgataac    3900
tgtcatttgt ttgaaaatgt tcgagactga acaaatagca tttaaactgc tggcatatag    3960
atgagatatt gtacttttgt gcaatgttta ttacctttga ttaaattgta atgtgaagct    4020
tttactaggt gaatagttca ttatgtagtg gaggcttcgt ggttgtccat tgaattgtca    4080
cagcaaaatc tataagtttc ttcaattcta caagatagat ccatatacct ttgatcactt    4140
ggagactctt ttttttgctgg tttctagata actcaggtaa atcagacctt tacagagtac    4200
```

```
agggctaggt gaaagaatta ctgaaaaatc accttgaaaa tccgaagggc tgatataccc      4260
tttatgttcc tgactgatgc gcagaacctg ggggaaatct acagcaatat acaggttgca      4320
atgctgataa cacaacagca atcctctcct ctacgtggac ttactgttgt ttttttaatt      4380
attattggaa tgggatttta gaaaatagaa gttacctttg tgtgtgtttt agggaaggta      4440
gagaagaatc tgctctttct ctgaatactg ttttgacccc aggcaggacc ttggaaggc       4500 caaaacatta acagtagtac ttctgttcac tgaagagtta tgttacatga agataaaatg      4560
gttttgtcgt gtttattatt gtattttgtg ttgatataaa taaacatggt aatttaaaca      4620
atgaaaaaaa aaaaaaaaaa aaaaaaa                                          4647
```

<210> SEQ ID NO 24
<211> LENGTH: 788
<212> TYPE: PRT
<213> ORGANISM: Homo sapiens

<400> SEQUENCE: 24

```
Met Gly Ile Glu Leu Leu Cys Leu Phe Phe Leu Phe Leu Gly Arg Asn
 1               5                  10                  15

Asp His Val Gln Gly Gly Cys Ala Leu Gly Gly Ala Glu Thr Cys Glu
            20                  25                  30

Asp Cys Leu Leu Ile Gly Pro Gln Cys Ala Trp Cys Ala Gln Glu Asn
        35                  40                  45

Phe Thr His Pro Ser Gly Val Gly Glu Arg Cys Asp Thr Pro Ala Asn
    50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
    130                 135                 140

Met Asp Asp Leu Asn Thr Ile Lys Glu Leu Gly Ser Arg Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
    210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
            260                 265                 270

Asp Ser His Phe Gly Met Asp Ser Lys Leu Ala Gly Ile Val Ile Pro
        275                 280                 285

Asn Asp Gly Leu Cys His Leu Asp Ser Lys Asn Glu Tyr Ser Met Ser
```

-continued

```
                290                 295                 300
Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
                340                 345                 350

Leu Gln Lys Asp Ser Gly Asn Ile Leu Gln Leu Ile Ile Ser Ala Tyr
                355                 360                 365

Glu Glu Leu Arg Ser Glu Val Glu Leu Glu Val Leu Gly Asp Thr Glu
                370                 375                 380

Gly Leu Asn Leu Ser Phe Thr Ala Ile Cys Asn Asn Gly Thr Leu Phe
385                 390                 395                 400

Gln His Gln Lys Lys Cys Ser His Met Lys Val Gly Asp Thr Ala Ser
                405                 410                 415

Phe Ser Val Thr Val Asn Ile Pro His Cys Glu Arg Arg Ser Arg His
                420                 425                 430

Ile Ile Ile Lys Pro Val Gly Leu Gly Asp Ala Leu Glu Leu Leu Val
                435                 440                 445

Ser Pro Glu Cys Asn Cys Asp Cys Gln Lys Glu Val Glu Val Asn Ser
                450                 455                 460

Ser Lys Cys His His Gly Asn Gly Ser Phe Gln Cys Gly Val Cys Ala
465                 470                 475                 480

Cys His Pro Gly His Met Gly Pro Arg Cys Glu Cys Gly Glu Asp Met
                485                 490                 495

Leu Ser Thr Asp Ser Cys Lys Glu Ala Pro Asp His Pro Ser Cys Ser
                500                 505                 510

Gly Arg Gly Asp Cys Tyr Cys Gly Gln Cys Ile Cys His Leu Ser Pro
                515                 520                 525

Tyr Gly Asn Ile Tyr Gly Pro Tyr Cys Gln Cys Asp Asn Phe Ser Cys
                530                 535                 540

Val Arg His Lys Gly Leu Leu Cys Gly Gly Asn Gly Asp Cys Asp Cys
545                 550                 555                 560

Gly Glu Cys Val Cys Arg Ser Gly Trp Thr Gly Glu Tyr Cys Asn Cys
                565                 570                 575

Thr Thr Ser Thr Asp Ser Cys Val Ser Glu Asp Gly Val Leu Cys Ser
                580                 585                 590

Gly Arg Gly Asp Cys Val Cys Gly Lys Cys Val Cys Thr Asn Pro Gly
                595                 600                 605

Ala Ser Gly Pro Thr Cys Glu Arg Cys Pro Thr Cys Gly Asp Pro Cys
610                 615                 620

Asn Ser Lys Arg Ser Cys Ile Glu Cys His Leu Ser Ala Ala Gly Gln
625                 630                 635                 640

Ala Arg Glu Glu Cys Val Asp Lys Cys Lys Leu Ala Gly Ala Thr Ile
                645                 650                 655

Ser Glu Glu Glu Asp Phe Ser Lys Asp Gly Ser Val Ser Cys Ser Leu
                660                 665                 670

Gln Gly Glu Asn Glu Cys Leu Ile Thr Phe Leu Ile Thr Thr Asp Asn
                675                 680                 685

Glu Gly Lys Thr Ile Ile His Ser Ile Asn Glu Lys Asp Cys Pro Lys
                690                 695                 700

Pro Pro Asn Ile Pro Met Ile Met Leu Gly Val Ser Leu Ala Ile Leu
705                 710                 715                 720
```

```
Leu Ile Gly Val Val Leu Leu Cys Ile Trp Lys Leu Val Ser Phe
                725                 730                 735

His Asp Arg Lys Glu Val Ala Lys Phe Glu Ala Glu Arg Ser Lys Ala
                740                 745                 750

Lys Trp Gln Thr Gly Thr Asn Pro Leu Tyr Arg Gly Ser Thr Ser Thr
                755                 760                 765

Phe Lys Asn Val Thr Tyr Lys His Arg Glu Lys Gln Lys Val Asp Leu
        770                 775                 780

Ser Thr Asp Cys
785

<210> SEQ ID NO 25
<211> LENGTH: 4474
<212> TYPE: DNA
<213> ORGANISM: Homo sapiens

<400> SEQUENCE: 25
gtagcctctg ttttcatttc agtcttaatg aaaactttct aacttatatc tcaagtttct      60
tttcaaagca gtgtaagtag tatttaaaat gttatacttc aagaaagaaa gactttaacg     120
atattcagcg ttggtcttgt aacgctgaag gtaattcatt ttttaatcgg tctgcacagc     180
aagaactgaa acgaatgggg attgaactgc tttgcctgtt cttctatttt ctaggaagga     240
atgatcacgt acaaggtggc tgtgccctgg gaggtgcaga acctgtgaa gactgcctgc      300
ttattggacc tcagtgtgcc tggtgtgctc aggagaattt tactcatcca tctggagttg     360
gcgaaaggtg gtgcgcagac tctgcaggtg catgtccgcc agactgagga ctacccggtg     420
gatttgtatt acctcatgga cctctccgcc tccatggatg acgacctcaa cacaataaag     480
gagctgggct cccggctttc aaagagatg tctaaattaa ccagcaactt tagactgggc      540
ttcggatctt ttgtggaaaa acctgtatcc cctttgtga aaacaacacc agaagaaatt      600
gccaaccctt gcagtagtat tccatacttc tgtttaccta catttggatt caagcacatt     660
ttgccattga caatgatgc tgaaagattc aatgaaattg tgaagaatca gaaaattct      720
gctaatattg acacacccga aggtggattt gatgcaatta tgcaagctgc tgtgtgtaag     780
gaaaaaattg gctggcggaa tgactccctc cacctcctgg tctttgtgag tgatgctgat     840
tctcattttg gaatggacag caaactagca ggcatcgtca ttcctaatga cgggctctgt     900
cacttggaca gcaagaatga atactccatg tcaactgtct ggaatatcc aacaattgga     960
caactcattg ataaactggt acaaacaac gtgttattga tcttcgctgt aacccaagaa    1020
caagttcatt tatatgagaa ttacgcaaaa cttattcctg agctacagt aggtctactt    1080
cagaaggact ccggaaacat tctccagctg atcatctcag cttatgaaga actgcggtct    1140
gaggtggaac tggaagtatt aggagacact gaaggactca acttgtcatt tacagccatc    1200
tgtaacaacg gtaccctctt ccaacaccaa agaaatgct ctcacatgaa agtgggagac     1260
acagcttcct tcagcgtgac tgtgaatatc ccacactgcg agagaagaag caggcacatt    1320
atcataaagc ctgtggggct ggggatgcc ctggaattac ttgtcagccc agaatgcaac     1380
tgcgactgtc agaaagaagt ggaagtgaac agctccaaat gtcaccacgg aacggctct    1440
ttccagtgtg gggtgtgtgc ctgccaccct ggcacatgg ggcctcgctg tgagtgtggc     1500
gaggacatgc tgagcacaga ttcctgcaag gaggcccag atcatccctc ctgcagcgga    1560
agggtgact gctactgtgg gcagtgtatc tgccacttgt ctcccatgg aaacatttat    1620
gggccttatt gccagtgtga caatttctcc tgcgtgagac acaaagggct gctctgcgga    1680
```

```
ggtaacggcg actgtgactg tggtgaatgt gtgtgcagga gcggctggac tggcgagtac    1740
tgcaactgca ccaccagcac ggactcctgc gtctctgaag atggagtgct ctgcagcggg    1800
cgcggggact gtgtttgtgg caagtgtgtt tgcacaaacc ctggagcctc aggaccaacc    1860
tgtgaacgat gtcctacctg tggtgacccc tgtaactcta aacggagctg cattgagtgc    1920
cacctgtcag cagctggcca agcccgagaa gaatgtgtgg acaagtgcaa actagctggt    1980
gcgaccatca gtgaagaaga agatttctca aaggatggtt ctgtttcctg ctctctgcaa    2040
ggagaaaatg aatgtcttat tacattccta ataactacag ataatgaggg gaaaaccatc    2100
attcacagca tcaatgaaaa agattgtccg aagcctccaa acattcccat gatcatgtta    2160
ggggtttccc tggctattct tctcatcggg gttgtcctac tgtgcatctg gaagctactg    2220
gtgtcatttc atgatcgtaa agaagttgcc aaatttgaag cagaacgatc aaaagccaag    2280
tggcaaacgg gaaccaatcc actctacaga ggatccacaa gtacttttaa aaatgtaact    2340
tataaacaca gggaaaaaca aaaggtagac cttccacag attgctagaa ctactttatg    2400
```

-continued

```
agagtacagg gctaggtgaa agaattactg aaaaatcacc ttgaaaatcc gaagggctga   4080
tatacccttt atgttcctga ctgatgcgca gaacctgggg gaaatctaca gcaatataca   4140
ggttgcaatg ctgataacac aacagcaatc ctctcctcta cgtggactta ctgttgtttt   4200
tttaattatt attggaatgg gattttagaa aatagaagtt acctttgtgt gtgttttagg   4260
gaaggtagag aagaatctgc tctttctctg aatactgttt tgaccccagg caggaccttg   4320
gaaaggccaa acattaaca gtagtacttc tgttcactga agagttatgt tacatgaaga    4380
taaaatggtt ttgtcgtgtt tattattgta ttttgtgttg atataaataa acatggtaat   4440
ttaaacaatg aaaaaaaaaa aaaaaaaaaa aaaa                               4474
```

<210> SEQ ID NO 26
<211> LENGTH: 715
<212> TYPE: PRT
<213> ORGANISM: Homo sapiens

<400> SEQUENCE: 26

```
Met Ile Thr Tyr Lys Val Ala Val Pro Trp Glu Val Gln Lys Pro Val
 1               5                  10                  15

Lys Thr Ala Cys Leu Leu Asp Leu Ser Val Pro Gly Val Leu Arg Arg
            20                  25                  30

Ile Leu Leu Ile His Leu Glu Leu Ala Lys Gly Gly Ala Gln Thr Leu
        35                  40                  45

Gln Val His Val Arg Gln Thr Glu Asp Tyr Pro Val Asp Leu Tyr Tyr
    50                  55                  60

Leu Met Asp Leu Ser Ala Ser Met Asp Asp Leu Asn Thr Ile Lys
65                  70                  75                  80

Glu Leu Gly Ser Arg Leu Ser Lys Glu Met Ser Lys Leu Thr Ser Asn
                85                  90                  95

Phe Arg Leu Gly Phe Gly Ser Phe Val Glu Lys Pro Val Ser Pro Phe
            100                 105                 110

Val Lys Thr Thr Pro Glu Glu Ile Ala Asn Pro Cys Ser Ser Ile Pro
        115                 120                 125

Tyr Phe Cys Leu Pro Thr Phe Gly Phe Lys His Ile Leu Pro Leu Thr
    130                 135                 140

Asn Asp Ala Glu Arg Phe Asn Glu Ile Val Lys Asn Gln Lys Ile Ser
145                 150                 155                 160

Ala Asn Ile Asp Thr Pro Glu Gly Gly Phe Asp Ala Ile Met Gln Ala
                165                 170                 175

Ala Val Cys Lys Glu Lys Ile Gly Trp Arg Asn Asp Ser Leu His Leu
            180                 185                 190

Leu Val Phe Val Ser Asp Ala Asp Ser His Phe Gly Met Asp Ser Lys
        195                 200                 205

Leu Ala Gly Ile Val Ile Pro Asn Asp Gly Leu Cys His Leu Asp Ser
    210                 215                 220

Lys Asn Glu Tyr Ser Met Ser Thr Val Leu Glu Tyr Pro Thr Ile Gly
225                 230                 235                 240

Gln Leu Ile Asp Lys Leu Val Gln Asn Asn Val Leu Leu Ile Phe Ala
                245                 250                 255

Val Thr Gln Glu Gln Val His Leu Tyr Glu Asn Tyr Ala Lys Leu Ile
            260                 265                 270

Pro Gly Ala Thr Val Gly Leu Leu Gln Lys Asp Ser Gly Asn Ile Leu
        275                 280                 285

Gln Leu Ile Ile Ser Ala Tyr Glu Glu Leu Arg Ser Glu Val Glu Leu
```

-continued

```
            290                 295                 300
Glu Val Leu Gly Asp Thr Glu Gly Leu Asn Leu Ser Phe Thr Ala Ile
305                 310                 315                 320
Cys Asn Asn Gly Thr Leu Phe Gln His Gln Lys Lys Cys Ser His Met
                325                 330                 335
Lys Val Gly Asp Thr Ala Ser Phe Ser Val Thr Val Asn Ile Pro His
                340                 345                 350
Cys Glu Arg Arg Ser Arg His Ile Ile Ile Lys Pro Val Gly Leu Gly
                355                 360                 365
Asp Ala Leu Glu Leu Leu Val Ser Pro Glu Cys Asn Cys Asp Cys Gln
370                 375                 380
Lys Glu Val Glu Val Asn Ser Ser Lys Cys His His Gly Asn Gly Ser
385                 390                 395                 400
Phe Gln Cys Gly Val Cys Ala Cys His Pro Gly His Met Gly Pro Arg
                405                 410                 415
Cys Glu Cys Gly Glu Asp Met Leu Ser Thr Asp Ser Cys Lys Glu Ala
                420                 425                 430
Pro Asp His Pro Ser Cys Ser Gly Arg Gly Asp Cys Tyr Cys Gly Gln
                435                 440                 445
Cys Ile Cys His Leu Ser Pro Tyr Gly Asn Ile Tyr Gly Pro Tyr Cys
450                 455                 460
Gln Cys Asp Asn Phe Ser Cys Val Arg His Lys Gly Leu Leu Cys Gly
465                 470                 475                 480
Gly Asn Gly Asp Cys Asp Cys Gly Glu Cys Val Cys Arg Ser Gly Trp
                485                 490                 495
Thr Gly Glu Tyr Cys Asn Cys Thr Thr Ser Thr Asp Ser Cys Val Ser
                500                 505                 510
Glu Asp Gly Val Leu Cys Ser Gly Arg Gly Asp Cys Val Cys Gly Lys
                515                 520                 525
Cys Val Cys Thr Asn Pro Gly Ala Ser Gly Pro Thr Cys Glu Arg Cys
530                 535                 540
Pro Thr Cys Gly Asp Pro Cys Asn Ser Lys Arg Ser Cys Ile Glu Cys
545                 550                 555                 560
His Leu Ser Ala Ala Gly Gln Ala Arg Glu Glu Cys Val Asp Lys Cys
                565                 570                 575
Lys Leu Ala Gly Ala Thr Ile Ser Glu Glu Asp Phe Ser Lys Asp
                580                 585                 590
Gly Ser Val Ser Cys Ser Leu Gln Gly Glu Asn Glu Cys Leu Ile Thr
                595                 600                 605
Phe Leu Ile Thr Thr Asp Asn Glu Gly Lys Thr Ile Ile His Ser Ile
                610                 615                 620
Asn Glu Lys Asp Cys Pro Lys Pro Asn Ile Pro Met Ile Met Leu
625                 630                 635                 640
Gly Val Ser Leu Ala Ile Leu Leu Ile Gly Val Val Leu Leu Cys Ile
                645                 650                 655
Trp Lys Leu Leu Val Ser Phe His Asp Arg Lys Glu Val Ala Lys Phe
                660                 665                 670
Glu Ala Glu Arg Ser Lys Ala Lys Trp Gln Thr Gly Thr Asn Pro Leu
                675                 680                 685
Tyr Arg Gly Ser Thr Ser Thr Phe Lys Asn Val Thr Tyr Lys His Arg
                690                 695                 700
Glu Lys Gln Lys Val Asp Leu Ser Thr Asp Cys
705                 710                 715
```

<210> SEQ ID NO 27
<211> LENGTH: 4327
<212> TYPE: DNA
<213> ORGANISM: Homo sapiens

<400> SEQUENCE: 27

| | | | | | |
|---|---|---|---|---|---|
| gtagcctctg | ttttcatttc | agtcttaatg | aaaactttct | aacttatatc | tcaagtttct | 60 |
| tttcaaagca | gtgtaagtag | tatttaaaat | gttatacttc | aagaaagaaa | gactttaacg | 120 |
| atattcagcg | ttggtcttgt | aacgctgaag | gtaattcatt | ttttaatcgg | tctgcacagc | 180 |
| aagaactgaa | acgaatgggg | attgaactgc | tttgcctgtt | ctttctattt | ctaggaagga | 240 |
| atgatcacgt | acaaggtggc | tgtgccctgg | gaggtgcaga | aacctgtgaa | gactgcctgc | 300 |
| ttattggacc | tcagtgtgcc | tggtgtgctc | aggagaattt | tactcatcca | tctggagttg | 360 |
| gcgaaaggtg | tgatacccca | gcaaaccttt | tagctaaagg | atgtcaatta | aacttcatcg | 420 |
| aaaaccctgt | ctcccaagta | gaaatactta | aaaataagcc | tctcagtgta | ggcagacaga | 480 |
| aaaatagttc | tgacattgtt | cagattgcgc | ctcaaagctt | gatccttaag | ttgagaccag | 540 |
| gtggtgcgca | gactctgcag | gtgcatgtcc | gccagactga | ggactaccg | gtggatttgt | 600 |
| attacctcat | ggacctctcc | gcctccatgg | atgacgacct | caacacaata | aaggagctgg | 660 |
| gctcccggct | ttccaaagag | atgtctaaat | taaccagcaa | ctttagactg | ggcttcggat | 720 |
| cttttgtgga | aaaacctgta | tcccctttg | tgaaaacaac | accagaagaa | attgccaacc | 780 |
| cttgcagtag | tattccatac | ttctgtttac | ctacatttgg | attcaagcac | attttgccat | 840 |
| tgacaaatga | tgctgaaaga | ttcaatgaaa | ttgtgaagaa | tcagaaaatt | tctgctaata | 900 |
| ttgacacacc | cgaaggtgga | tttgatgcaa | ttatgcaagc | tgctgtgtgt | aaggaaaaaa | 960 |
| ttggctggcg | gaatgactcc | ctccacctcc | tggtctttgt | gagtgatgct | gattctcatt | 1020 |
| ttggaatgga | cagcaaacta | gcaggcatcg | tcattcctaa | tgacgggctc | tgtcacttgg | 1080 |
| acagcaagaa | tgaatactcc | atgtcaactg | tcttggaata | tccaacaatt | ggacaactca | 1140 |
| ttgataaact | ggtacaaaac | aacgtgttat | tgatcttcgc | tgtaacccaa | gaacaagttc | 1200 |
| atttatatga | gaattacgca | aaacttattc | ctggagctac | agtaggtcta | cttcagaagg | 1260 |
| actccggaaa | cattctccag | ctgatcatct | cagcttatga | agaactgcgg | tctgaggtgg | 1320 |
| aactggaagt | attaggagac | actgaaggac | tcaacttgtc | atttacagcc | atctgtaaca | 1380 |
| acggtaccct | cttccaacac | caaaagaaat | gctctcacat | gaaagtggga | gacacagctt | 1440 |
| ccttcagcgt | gactgtgaat | atcccacact | gcgagagaag | aagcaggcac | attatcataa | 1500 |
| agcctgtggg | gctgggggat | gccctggaat | tacttgtcag | cccagaatgc | aactgcgact | 1560 |
| gtcagaaaga | agtggaagtg | aacagctcca | atgtcaccca | cgggaacggc | tctttccagt | 1620 |
| gtggggtgtg | tgcctgccac | cctggccaca | tgggccctcg | ctgtgagtgt | ggcgaggaca | 1680 |
| tgctgagcac | agattcctgc | aaggaggccc | agatcatcc | ctcctgcagc | ggaaggggtg | 1740 |
| actgctactg | tgggcagtgt | atctgccact | gtctcccta | tggaaacatt | tatgggcctt | 1800 |
| attgccagtg | tgacaatttc | tcctgcgtga | gacacaaagg | gctgctctgc | ggagatttct | 1860 |
| caaaggatgg | ttctgtttcc | tgctctctgc | aaggagaaaa | tgaatgtctt | attacattcc | 1920 |
| taataactac | agataatgag | gggaaaacca | tcattcacag | catcaatgaa | aaagattgtc | 1980 |
| cgaagcctcc | aaacattccc | atgatcatgt | taggggtttc | cctggctatt | cttctcatcg | 2040 |
| gggttgtcct | actgtgcatc | tggaagctac | tggtgtcatt | tcatgatcgt | aaagaagttg | 2100 |

```
ccaaatttga agcagaacga tcaaaagcca agtggcaaac gggaaccaat ccactctaca   2160
gaggatccac aagtactttt aaaaatgtaa cttataaaca cagggaaaaa caaaaggtag   2220
acctttccac agattgctag aactacttta tgcatgaaaa aagtctgttt cactgatatg   2280
aaatgttaat gcactattta attttttttct ctttgttgct tcaaaatgag gttggtttaa   2340
gataataata ggacatctgc agataagtca tcctctacat gaaggtgaca gactgttggc   2400
agtttcaaaa taatcaagaa gagaaatatc cttagcaaag agatgacttt ggggatcatt   2460
tgaggaatac taactctgtt gcattaatgc ttcaaaaaat catcaaatga ttcatggggg   2520
cctgatttgc atttgaaaaa tgtttgaaat tagagtctca tttgtttcag gaatgcagct   2580
acctgagttt tttgtctcgg caaagtcaca agcccatat actcacattg tgtgtctata    2640
cttgccaatt aattctaaac ttgtaggaaa tatgccctct cttaaaagga aattttttt    2700
taaatctctg agaaatgaga ttctgagttt atttcagcta aaaggttgca attcttctga   2760
agatatctca aatataaggt tgaaagttaa gtgttaataa ttttgtgaa tttatacaca    2820
cctaaacgtt aagtacacaa atattttatt tgttttacaa ataaggaata agtaatttat   2880
aaattaagaa gttacctata aaaataaaaa gataacaacc ctatcatata gcttatttt    2940
aaattacctg aaaaacgata ttctacactg tttccttttt gactctgagt tttcaaactg   3000
ttacttctcc catatttctc aatccatttc actcagttgc acagtctttt aaaccctgta   3060
attgtcatac caaagtttct ttttaaaaaa aaattacttt aaatgcttag tttattcaaa   3120
gagcgatcca ataatataaa aggaacatgt gttaaacaca ataaaatttt aaatggctct   3180
aaatcaagca catcaagagt atacaagtct taaaggcttt ttaatacata ctctttttccc   3240
atctatgtaa cccaacttgc acatttcagc tgcatgtggt gaatatgcat catatatta    3300
ctttaagagg taagatttta cttgcaaaat acatgtgcaa attaggatcc atcagttgat   3360
ggaagagatg gactctagaa tattatttct tgtggttatt actcctttac aaagcacttt   3420
cgtctcactt gatcctcata aggaaactaa ggctcagaat gagtagagct gggttcagaa   3480
tctagctctt ctaactccaa gccatctcct ctttccactg caggaaactg cctcttttgt   3540
cagtgaaata atagaaagat tgtgttagtt aagtgataac tgtcatttgt ttgaaaatgt   3600
tcgagactga acaaatagca tttaaactgc tggcatatag atgagatatt gtacttttgt   3660
gcaatgttta ttacctttga ttaaattgta atgtgaagct tttactaggt gaatagttca   3720
ttatgtagtg gaggcttcgt ggttgtccat tgaattgtca cagcaaaatc tataagtttc   3780
ttcaattcta caagatagat ccatatacct ttgatcactt ggagactctt tttttgctgg   3840
tttctagata actcaggtaa atcagaccct tacagagtac agggctaggt gaaagaatta   3900
ctgaaaaatc accttgaaaa tccgaagggc tgatataccc tttatgttcc tgactgatgc   3960
gcagaacctg ggggaaatct acagcaatat acaggttgca atgctgataa cacaacagca   4020
atcctctcct ctacgtggac ttactgttgt ttttttaatt attattggaa tgggatttta   4080
gaaatagaa gttacctttg tgtgtgtttt agggaaggta gagaagaatc tgctctttct   4140
ctgaatactg ttttgacccc aggcaggacc ttggaaaggc caaaacatta acagtagtac   4200
ttctgttcac tgaagagtta tgttacatga agataaaatg gttttgtcgt gtttattatt   4260
gtattttgtg ttgatataaa taaacatggt aatttaaaca atgaaaaaaa aaaaaaaaa    4320
aaaaaaa                                                            4327
```

<210> SEQ ID NO 28
<211> LENGTH: 681

```
<212> TYPE: PRT
<213> ORGANISM: Homo sapiens

<400> SEQUENCE: 28

Met Gly Ile Glu Leu Leu Cys Leu Phe Phe Leu Phe Leu Gly Arg Asn
 1               5                   10                  15

Asp His Val Gln Gly Gly Cys Ala Leu Gly Gly Ala Glu Thr Cys Glu
             20                  25                  30

Asp Cys Leu Leu Ile Gly Pro Gln Cys Ala Trp Cys Ala Gln Glu Asn
         35                  40                  45

Phe Thr His Pro Ser Gly Val Gly Glu Arg Cys Asp Thr Pro Ala Asn
 50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                 85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
130                 135                 140

Met Asp Asp Asp Leu Asn Thr Ile Lys Glu Leu Gly Ser Arg Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
            245                 250                 255

Gly Trp Arg Asn Asp Ser Leu His Leu Leu Val Phe Val Ser Asp Ala
        260                 265                 270

Asp Ser His Phe Gly Met Asp Ser Lys Leu Ala Gly Ile Val Ile Pro
    275                 280                 285

Asn Asp Gly Leu Cys His Leu Asp Ser Lys Asn Glu Tyr Ser Met Ser
290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
            340                 345                 350

Leu Gln Lys Asp Ser Gly Asn Ile Leu Gln Leu Ile Ile Ser Ala Tyr
        355                 360                 365

Glu Glu Leu Arg Ser Glu Val Glu Leu Glu Val Leu Gly Asp Thr Glu
370                 375                 380

Gly Leu Asn Leu Ser Phe Thr Ala Ile Cys Asn Asn Gly Thr Leu Phe
385                 390                 395                 400
```

```
Gln His Gln Lys Lys Cys Ser His Met Lys Val Gly Asp Thr Ala Ser
                405                 410                 415

Phe Ser Val Thr Val Asn Ile Pro His Cys Glu Arg Arg Ser Arg His
            420                 425                 430

Ile Ile Ile Lys Pro Val Gly Leu Gly Asp Ala Leu Glu Leu Leu Val
        435                 440                 445

Ser Pro Glu Cys Asn Cys Asp Cys Gln Lys Glu Val Glu Val Asn Ser
    450                 455                 460

Ser Lys Cys His His Gly Asn Gly Ser Phe Gln Cys Gly Val Cys Ala
465                 470                 475                 480

Cys His Pro Gly His Met Gly Pro Arg Cys Glu Cys Gly Glu Asp Met
                485                 490                 495

Leu Ser Thr Asp Ser Cys Lys Glu Ala Pro Asp His Pro Ser Cys Ser
            500                 505                 510

Gly Arg Gly Asp Cys Tyr Cys Gly Gln Cys Ile Cys His Leu Ser Pro
        515                 520                 525

Tyr Gly Asn Ile Tyr Gly Pro Tyr Cys Gln Cys Asp Asn Phe Ser Cys
    530                 535                 540

Val Arg His Lys Gly Leu Leu Cys Gly Asp Phe Ser Lys Asp Gly Ser
545                 550                 555                 560

Val Ser Cys Ser Leu Gln Gly Glu Asn Glu Cys Leu Ile Thr Phe Leu
                565                 570                 575

Ile Thr Thr Asp Asn Glu Gly Lys Thr Ile Ile His Ser Ile Asn Glu
            580                 585                 590

Lys Asp Cys Pro Lys Pro Pro Asn Ile Pro Met Ile Met Leu Gly Val
        595                 600                 605

Ser Leu Ala Ile Leu Leu Ile Gly Val Val Leu Leu Cys Ile Trp Lys
    610                 615                 620

Leu Leu Val Ser Phe His Asp Arg Lys Glu Val Ala Lys Phe Glu Ala
625                 630                 635                 640

Glu Arg Ser Lys Ala Lys Trp Gln Thr Gly Thr Asn Pro Leu Tyr Arg
                645                 650                 655

Gly Ser Thr Ser Thr Phe Lys Asn Val Thr Tyr Lys His Arg Glu Lys
            660                 665                 670

Gln Lys Val Asp Leu Ser Thr Asp Cys
        675                 680

<210> SEQ ID NO 29
<211> LENGTH: 3176
<212> TYPE: DNA
<213> ORGANISM: Homo sapiens

<400> SEQUENCE: 29
tgataaccca aggtattcac agcaagatac agtgagtctt aaagttaagc accgtgcaat      60
y
tagctttgct tccttgggtt tttgaaacat gcatctgtat aaacctgcct gtgcagacat     120
y
cccgagcccc aagctgggtc tgccaaaatc cagtgaatcg gctctaaaat gtagatggca     180
y
cctagcagtg accaagactc agcctcaggc ggcctgcaaa cctgtgaggc ccagtggagc     240
y
agccgaacag aaatatgtgg aaaagtttct acgtgttcat ggaatttcgt tgcaggaaac     300
y
caccagagca gagacgggca tggcatacag gaatcttgga aaatcaggac tcagagtttc     360
y
ttgcttgggt cttggaacat gggtgacatt tggaggtcaa atttcagatg aggttgctga     420
y
acggctgatg accatcgcct atgaaagtgg tgttaacctc tttgatactg ccgaagtcta     480
y
```

```
tgctgctgga aaggctgaag tgattctggg gagcatcatc aagaagaaag gctggaggag     540
y
gtccagtctg gtcataacaa ccaaactcta ctggggtgga aaagctgaaa cagaagagg     600
y
gctgtcaaga aagcatatta ttgaaggatt gaagggctcc ctccagaggc tgcagctcga     660
y
gtatgtggat gtggtctttg caaatcgacc ggacagtaac actcccatgg aagaaattgt     720
y
ccgagccatg acacatgtga taaaccaagg catggcgatg tactgggca cctcgagatg     780
y
gagtgctatg gagatcatgg aagcctattc tgtagcaaga cagttcaata tgatcccacc     840
y
ggtctgtgaa caagctgagt accatctttt ccagagagag aaagtggagg tccagctgcc     900
y
agagctctac cacaaaatag gtgttggcgc aatgacatgg tctccacttg cctgtggaat     960
catctcagga aaatacggaa acggggtgcc tgaaagttcc agggcttcac tgaagtgcta    1020
ccagtggttg aaagaaagaa ttgtaagtga agaagggaga aaacagcaaa acaagctaaa    1080
agacctttcc ccaattgcgg agcgtctggg atgcacacta cctcagctag ctgttgcgtg    1140
gtgcctgaga aatgaaggtg tgagttctgt gctcctggga tcatccactc ctgaacaact    1200
cattgaaaac cttggtgcca ttcaggttct cccaaagatg acatcacatg tggtaaatga    1260
gattgataac atactgcgca acaagcccta cagcaagaag gactatagat cataaggcaa    1320
tgcatgaacc acagaagctg catggttaaa atagcggcct gtgcccagta cagaaaggtg    1380
ttactaacca gtcttttgaa tcacttagca gcttgctcgt caacctctag tgtccctccc    1440
tggattcttt gaggtgtctg ctgtcgctac cactgtgcac atctgaaaac tcacaaccaa    1500
gaaaatccat tctatttcct tatcttggac tggagtcacc tattcttgca ttgctgtata    1560
cacctcatgc ttatgcaatg ggaagaatat gggggccagg gggtgtggta ctaccttcag    1620
gcatttggta actcaaagaa ggctgtacag atatattttt tcaaaaagaa caaaatccac    1680
agatgcaatg tgagttgcgt aagaaacaga gtagatagac taaattcagt gaaggaaagg    1740
aattgagaga ttttcttag taaatagatt attgttaagt aaatagttat taaaaatata    1800
tctcactgca aaaaaaaaa aagcagtatc ttcactcaaa agtcttgctt ggaagaataa    1860
gcagaaagaa ttttatatat tttttttcta ttttcacatt catactaaca agttttgttc    1920
catttgttat tcaataaaac aaaaatttct aggtatttgc tttattacct ttcaaatatt    1980
tactgttgct tggccccaag aatggccttg taacttatt ccagaatgtc tattaggatt    2040
ctaatgttat gtccacttac aagtagagac agtaaaagga tgaataccca atctttagtg    2100
acaatgcagc tgatttatga agagagggc tacactgcta tggaaactta gcttcaaaga    2160
aaatgcaatg tatctgcaat taggtgttca ttttttacta catttttatta aaacctgctt    2220
tatactttca actgcttgta ggcacaactt ctgcaagttt aaatatttga gctttacaaa    2280
taaacataca catgctcagt ttttttaagt aaacctgtaa atacccagg aaggcaaatg    2340
ttcattgttt aattagcact gggatttat aatataatgt ttggtatttt tgaggcattg    2400
ttaacatgaa agtcaaccac tggctttgtg aaaaatgcta tgtcactatt cagaatatgc    2460
tgggtaaatt aacttgccta gtgaaaagca aatgttaaa gaaagaactt ctggttctat    2520
aatcatatta tatgcactaa actatatgca tgaaagttct ttgcatggat taatgggct    2580
taccccttgtt gcactcgaaa tctgaggtgt atctagccct gccactattg gctacttacc    2640
ctcattaata tccccttga gaaaaattgt gagactatac tgtgtcaata tctgtaaaaa    2700
gagagaaaac atgttttttt tttttgaag ggggtggtgt gggagtggcc ctttaactcc    2760
tatttggcta tctgaggatg tacaaaattc tcatttaatt ttctggtcag caagttcccc    2820
acacagaaat cactctgagg tttacagaag aactgtaata ttatttttaaa atgcgatttt    2880
```

-continued

```
ctgtcattag ttctagatat gtacttcatg gttaaattct aaatctgaaa atgctagtgg   2940
gagatatcaa gaaattttct ttttgattac tagtacctgt attctaacag agagtttgaa   3000
ttttttgccc gtgttatcag aatgatggaa attgatcatt ttcagttgtt cattgtgtat   3060
tcaatccagc tgaactgctg tatgtataga ggagcttgag gtgctgtcta atgggaaatg   3120
tgatttgatt gatttatttg cttagagtaa taaaagcatt ttgtgcattc aatctt        3176
```

<210> SEQ ID NO 30
<211> LENGTH: 408
<212> TYPE: PRT
<213> ORGANISM: Homo sapiens

<400> SEQUENCE: 30

```
Met His Leu Tyr Lys Pro Ala Cys Ala Asp Ile Pro Ser Pro Lys Leu
 1               5                  10                  15

Gly Leu Pro Lys Ser Ser Glu Ser Ala Leu Lys Cys Arg Trp His Leu
            20                  25                  30

Ala Val Thr Lys Thr Gln Pro Gln Ala Ala Cys Lys Pro Val Arg Pro
        35                  40                  45

Ser Gly Ala Ala Glu Gln Lys Tyr Val Glu Lys Phe Leu Arg Val His
    50                  55                  60

Gly Ile Ser Leu Gln Glu Thr Thr Arg Ala Glu Thr Gly Met Ala Tyr
65                  70                  75                  80

Arg Asn Leu Gly Lys Ser Gly Leu Arg Val Ser Cys Leu Gly Leu Gly
                85                  90                  95

Thr Trp Val Thr Phe Gly Gly Gln Ile Ser Asp Glu Val Ala Glu Arg
            100                 105                 110

Leu Met Thr Ile Ala Tyr Glu Ser Gly Val Asn Leu Phe Asp Thr Ala
        115                 120                 125

Glu Val Tyr Ala Ala Gly Lys Ala Glu Val Ile Leu Gly Ser Ile Ile
    130                 135                 140

Lys Lys Lys Gly Trp Arg Arg Ser Ser Leu Val Ile Thr Thr Lys Leu
145                 150                 155                 160

Tyr Trp Gly Gly Lys Ala Glu Thr Glu Arg Gly Leu Ser Arg Lys His
                165                 170                 175

Ile Ile Glu Gly Leu Lys Gly Ser Leu Gln Arg Leu Gln Leu Glu Tyr
            180                 185                 190

Val Asp Val Val Phe Ala Asn Arg Pro Asp Ser Asn Thr Pro Met Glu
        195                 200                 205

Glu Ile Val Arg Ala Met Thr His Val Ile Asn Gln Gly Met Ala Met
    210                 215                 220

Tyr Trp Gly Thr Ser Arg Trp Ser Ala Met Glu Ile Met Glu Ala Tyr
225                 230                 235                 240

Ser Val Ala Arg Gln Phe Asn Met Ile Pro Pro Val Cys Glu Gln Ala
                245                 250                 255

Glu Tyr His Leu Phe Gln Arg Glu Lys Val Glu Val Gln Leu Pro Glu
            260                 265                 270

Leu Tyr His Lys Ile Gly Val Gly Ala Met Thr Trp Ser Pro Leu Ala
        275                 280                 285

Cys Gly Ile Ile Ser Gly Lys Tyr Gly Asn Gly Val Pro Glu Ser Ser
    290                 295                 300

Arg Ala Ser Leu Lys Cys Tyr Gln Trp Leu Lys Glu Arg Ile Val Ser
305                 310                 315                 320
```

```
Glu Glu Gly Arg Lys Gln Gln Asn Lys Leu Lys Asp Leu Ser Pro Ile
                325                 330                 335

Ala Glu Arg Leu Gly Cys Thr Leu Pro Gln Leu Ala Val Ala Trp Cys
            340                 345                 350

Leu Arg Asn Glu Gly Val Ser Ser Val Leu Leu Gly Ser Ser Thr Pro
        355                 360                 365

Glu Gln Leu Ile Glu Asn Leu Gly Ala Ile Gln Val Leu Pro Lys Met
    370                 375                 380

Thr Ser His Val Val Asn Glu Ile Asp Asn Ile Leu Arg Asn Lys Pro
385                 390                 395                 400

Tyr Ser Lys Lys Asp Tyr Arg Ser
                405

<210> SEQ ID NO 31
<211> LENGTH: 3744
<212> TYPE: DNA
<213> ORGANISM: Homo sapiens

<400> SEQUENCE: 31
```

| | | | | | |
|---|---|---|---|---|---|
| ccacgcgtcc | ggtggcggtc | gagcgtggcg | taggcgaatc | ctcggcacta | agcatatgga | 60 |
| cctcgcggcg | gcagcggagc | cgggcgccgg | cagccagcac | ctggaggtcc | gcgacgaggt | 120 |
| ggccgagaag | tgccagaaac | tgttcctgga | cttcttggag | gagtttcaga | gcagcgatgg | 180 |
| agaaattaaa | tacttgcaat | tagcagagga | actgattcgt | cctgagagaa | acacattggt | 240 |
| tgtgagtttt | gtggacctgg | aacaatttaa | ccagcaactt | tccaccacca | ttcaaggaga | 300 |
| gttctataga | gtttacccct | acctgtgtcg | ggccttgaaa | acattcgtca | agaccgtaa | 360 |
| agagatccct | cttgccaagg | atttttatgt | tgcattccaa | gacctgccta | ccagacacaa | 420 |
| gattcgagag | ctcacctcat | ccagaattgg | tttgctcact | cgcatcagtg | ggcaggtggt | 480 |
| gcggactcac | ccagttcacc | cagagcttgt | gagcggaact | tttctgtgct | ggactgtca | 540 |
| gacagtgatc | agggatgtag | aacagcagtt | caaatacaca | cagccaaaca | tctgccgaaa | 600 |
| tccagtttgt | gccaacagga | ggagattctt | actggataca | aataaatcaa | gatttgttga | 660 |
| ttttcaaaag | gttcgtattc | aagagaccca | agctgagctt | cctcgaggga | gtatccccg | 720 |
| cagtttagaa | gtaattttaa | gggctgaagc | tgtggaatca | gctcaagctg | gtgacaagtg | 780 |
| tgacttttaca | gggacactga | ttgttgtgcc | tgacgtctcc | aagcttagca | caccaggagc | 840 |
| acgtgcagaa | actaattccc | gtgtcagtgg | tgttgatgga | tatgagacag | aaggcattcg | 900 |
| aggactccgg | gcccttggtg | ttagggacct | ttcttatagg | ctggtctttc | ttgcctgctg | 960 |
| tgttgcgcca | accaacccaa | ggtttggggg | gaaagagctc | agagatgagg | aacagacagc | 1020 |
| tgagagcatt | aagaaccaaa | tgactgtgaa | agaatgggga | aaagtgtttg | agatgagtca | 1080 |
| agataaaaat | ctataccaca | atctttgtac | cagcctgttc | cctactatac | atggcaatga | 1140 |
| tgaagtaaaa | cggggtgtcc | tgctgatgct | ctttggtggc | gttccaaaga | acaggagaa | 1200 |
| agggacctct | cttcgagggg | acataaatgt | ttgcattgtt | ggtgacccaa | gtacagctaa | 1260 |
| gagccaattt | ctcaagcacg | tggaggagtt | cagccccaga | gctgtctaca | ccagtggtaa | 1320 |
| agcgtccagt | gctgctggct | taacagcagc | tgttgtgaga | gatgaagaat | ctcatgagtt | 1380 |
| tgtcattgag | gctggagctt | tgatgttggc | tgataatggt | gtgtgttgta | ttgatgaatt | 1440 |
| tgataagatg | gacgtgcggg | atcaagttgc | tattcatgaa | gctatggaac | agcagaccat | 1500 |
| atccatcact | aaagcaggag | tgaaggctac | tctgaacgcc | cggacgtcca | ttttggcagc | 1560 |
| agcaaaccca | atcagtggac | actatgacag | atcaaaatca | ttgaaacaga | atataaattt | 1620 |

```
gtcagctccc atcatgtccc gattcgatct cttctttatc cttgtggatg aatgtaatga    1680
ggttacagat tatgccattg ccaggcgcat agtagatttg cattcaagaa ttgaggaatc    1740
aattgatcgt gtctattccc tcgatgatat cagaagatat cttctctttg caagacagtt    1800
taaacccaag atttccaaag agtcagagga cttcattgtg gagcaatata acatctccg    1860 ccagagagat ggttctggag tgaccaagtc ttcatggagg attacagtgc gacagcttga    1920
gagcatgatt cgtctctctg aagctatggc tcggatgcac tgctgtgatg aggtccaacc    1980
taaacatgtg aaggaagctt ccggttact gaataaatca atcatccgtg tggaaacacc    2040
tgatgtcaat ctagatcaag aggaagagat ccagatggag gtagatgagg gtgccggtgg    2100
catcaatggt catgctgaca gccctgctcc tgtgaacggg atcaatggct acaatgaaga    2160
cataaatcaa gagtctgctc ccaaagcctc cttaaggctg ggcttctctg agtactgccg    2220
aatctctaac cttattgtgc ttcacctcag aaaggtggaa gaagaagagg acgagtcagc    2280
attaaagagg agcgagcttg ttaactggta cttgaaggaa atcgaatcag agatagactc    2340
tgaagaagaa cttataaata aaaaaagaat catagagaaa gttattcatc gactcacaca    2400
ctatgatcat gttctaattg agctcaccca ggctggattg aaaggctcca cagagggaag    2460
tgagagctat gaagaagatc cctacttggt agttaaccct aactacttgc tcgaagattg    2520
agatagtgaa agtaactgac cagagctgag gaactgtggc acagcacctc gtggcctgga    2580
gcctggctgg agctctgcta gggacagaag tgtttctgga agtgatgctt ccaggatttg    2640
ttttcagaaa caagaattga gttgatggtc ctatgtgtca cattcatcac aggtttcata    2700
ccaacacagg cttcagcact tcctttggtg tgtttcctgt cccagtgaag ttggaaccaa    2760
ataatgtgta gtctctataa ccaataccct tgttttcatg tgtaagaaaa ggcccattac    2820
ttttaaggta tgtgctgtcc tattgagcaa ataacttttt ttcaattgcc agctactgct    2880
tttattcatc aaaataaaat aacttgttct gaagttgtct attggatttc tttctactgt    2940
accctgatta ttacttccat ctacttctga atgtgagact ttccctttt gcttaacctg    3000 gagtgaagag gtagaactgt ggtattatgg atgaggtttc tatgagaagg agtcattaga    3060
gaactcatat gaaagctaga ggccttagag atgactttcc aaggttaatt ccagttttt    3120 ttttttttaa gttatgaaaa gtttattata ctttttaaa attactcttt agtaatttat    3180
tttacttctg tgtcctaagg gtaatttctc aggattgttt tcaaattgct tttttagggg    3240
aaataggtca tttgctatat tacaagcaat ccccaaattt tatggtcttc caggaaaagt    3300
tattaccgtt tatgatacta acagttcctg agacttagct atgatcagta tgttcatgag    3360
gtggagcagt tcctgtgttg cagcttttaa caacagatgg cattcattaa atcacaaagt    3420
atgttaaagg tcacaaaagc aaaataactg tctgaggcta aggcccacgt gggacagtct    3480
aatacccatg agtactcaac ttgccttgat gtctgagctt ccagtgcaa tgtgaatttg    3540 agcagccaga aatctattag tagaaagcaa gacagattaa tataggttaa aacaatgatt    3600
taaatatgtt tctcccaata attatctctt tccctggaat caacttgtat gaaaccttgt    3660
caaaatgtac tccacaagta tgtacaatta agtattttaa aaataaatgg caaacattaa    3720
aaaaaaaaaa aaaaaaaaaa aaaa                                          3744
```

<210> SEQ ID NO 32
<211> LENGTH: 821
<212> TYPE: PRT
<213> ORGANISM: Homo sapiens -continued

```
<400> SEQUENCE: 32

Met Asp Leu Ala Ala Ala Glu Pro Gly Ala Gly Ser Gln His Leu
 1               5                  10                  15

Glu Val Arg Asp Glu Val Ala Glu Lys Cys Gln Lys Leu Phe Leu Asp
             20                  25                  30

Phe Leu Glu Glu Phe Gln Ser Ser Asp Gly Glu Ile Lys Tyr Leu Gln
         35                  40                  45

Leu Ala Glu Glu Leu Ile Arg Pro Glu Arg Asn Thr Leu Val Val Ser
     50                  55                  60

Phe Val Asp Leu Glu Gln Phe Asn Gln Gln Leu Ser Thr Thr Ile Gln
 65                  70                  75                  80

Glu Glu Phe Tyr Arg Val Tyr Pro Tyr Leu Cys Arg Ala Leu Lys Thr
                 85                  90                  95

Phe Val Lys Asp Arg Lys Glu Ile Pro Leu Ala Lys Asp Phe Tyr Val
            100                 105                 110

Ala Phe Gln Asp Leu Pro Thr Arg His Lys Ile Arg Glu Leu Thr Ser
        115                 120                 125

Ser Arg Ile Gly Leu Leu Thr Arg Ile Ser Gly Gln Val Val Arg Thr
    130                 135                 140

His Pro Val His Pro Glu Leu Val Ser Gly Thr Phe Leu Cys Leu Asp
145                 150                 155                 160

Cys Gln Thr Val Ile Arg Asp Val Glu Gln Gln Phe Lys Tyr Thr Gln
                165                 170                 175

Pro Asn Ile Cys Arg Asn Pro Val Cys Ala Asn Arg Arg Arg Phe Leu
            180                 185                 190

Leu Asp Thr Asn Lys Ser Arg Phe Val Asp Phe Gln Lys Val Arg Ile
        195                 200                 205

Gln Glu Thr Gln Ala Glu Leu Pro Arg Gly Ser Ile Pro Arg Ser Leu
    210                 215                 220

Glu Val Ile Leu Arg Ala Glu Ala Val Glu Ser Ala Gln Ala Gly Asp
225                 230                 235                 240

Lys Cys Asp Phe Thr Gly Thr Leu Ile Val Val Pro Asp Val Ser Lys
                245                 250                 255

Leu Ser Thr Pro Gly Ala Arg Ala Glu Thr Asn Ser Arg Val Ser Gly
            260                 265                 270

Val Asp Gly Tyr Glu Thr Glu Gly Ile Arg Gly Leu Arg Ala Leu Gly
        275                 280                 285

Val Arg Asp Leu Ser Tyr Arg Leu Val Phe Leu Ala Cys Cys Val Ala
    290                 295                 300

Pro Thr Asn Pro Arg Phe Gly Gly Lys Glu Leu Arg Asp Glu Glu Gln
305                 310                 315                 320

Thr Ala Glu Ser Ile Lys Asn Gln Met Thr Val Lys Glu Trp Glu Lys
                325                 330                 335

Val Phe Glu Met Ser Gln Asp Lys Asn Leu Tyr His Asn Leu Cys Thr
            340                 345                 350

Ser Leu Phe Pro Thr Ile His Gly Asn Asp Glu Val Lys Arg Gly Val
        355                 360                 365

Leu Leu Met Leu Phe Gly Gly Val Pro Lys Thr Thr Gly Glu Gly Thr
    370                 375                 380

Ser Leu Arg Gly Asp Ile Asn Val Cys Ile Val Gly Asp Pro Ser Thr
385                 390                 395                 400

Ala Lys Ser Gln Phe Leu Lys His Val Glu Glu Phe Ser Pro Arg Ala
                405                 410                 415
```

```
Val Tyr Thr Ser Gly Lys Ala Ser Ser Ala Ala Gly Leu Thr Ala Ala
            420                 425                 430

Val Val Arg Asp Glu Glu Ser His Glu Phe Val Ile Glu Ala Gly Ala
            435                 440                 445

Leu Met Leu Ala Asp Asn Gly Val Cys Cys Ile Asp Glu Phe Asp Lys
            450                 455                 460

Met Asp Val Arg Asp Gln Val Ala Ile His Glu Ala Met Glu Gln Gln
465                 470                 475                 480

Thr Ile Ser Ile Thr Lys Ala Gly Val Lys Ala Thr Leu Asn Ala Arg
            485                 490                 495

Thr Ser Ile Leu Ala Ala Ala Asn Pro Ile Ser Gly His Tyr Asp Arg
            500                 505                 510

Ser Lys Ser Leu Lys Gln Asn Ile Asn Leu Ser Ala Pro Ile Met Ser
            515                 520                 525

Arg Phe Asp Leu Phe Phe Ile Leu Val Asp Glu Cys Asn Glu Val Thr
            530                 535                 540

Asp Tyr Ala Ile Ala Arg Arg Ile Val Asp Leu His Ser Arg Ile Glu
545                 550                 555                 560

Glu Ser Ile Asp Arg Val Tyr Ser Leu Asp Asp Ile Arg Arg Tyr Leu
            565                 570                 575

Leu Phe Ala Arg Gln Phe Lys Pro Lys Ile Ser Lys Glu Ser Glu Asp
            580                 585                 590

Phe Ile Val Glu Gln Tyr Lys His Leu Arg Gln Arg Asp Gly Ser Gly
            595                 600                 605

Val Thr Lys Ser Ser Trp Arg Ile Thr Val Arg Gln Leu Glu Ser Met
            610                 615                 620

Ile Arg Leu Ser Glu Ala Met Ala Arg Met His Cys Cys Asp Glu Val
625                 630                 635                 640

Gln Pro Lys His Val Lys Glu Ala Phe Arg Leu Leu Asn Lys Ser Ile
            645                 650                 655

Ile Arg Val Glu Thr Pro Asp Val Asn Leu Asp Gln Glu Glu Glu Ile
            660                 665                 670

Gln Met Glu Val Asp Glu Gly Ala Gly Gly Ile Asn Gly His Ala Asp
            675                 680                 685

Ser Pro Ala Pro Val Asn Gly Ile Asn Gly Tyr Asn Glu Asp Ile Asn
            690                 695                 700

Gln Glu Ser Ala Pro Lys Ala Ser Leu Arg Leu Gly Phe Ser Glu Tyr
705                 710                 715                 720

Cys Arg Ile Ser Asn Leu Ile Val Leu His Leu Arg Lys Val Glu Glu
            725                 730                 735

Glu Glu Asp Glu Ser Ala Leu Lys Arg Ser Glu Leu Val Asn Trp Tyr
            740                 745                 750

Leu Lys Glu Ile Glu Ser Glu Ile Asp Ser Glu Glu Leu Ile Asn
            755                 760                 765

Lys Lys Arg Ile Ile Glu Lys Val Ile His Arg Leu Thr His Tyr Asp
            770                 775                 780

His Val Leu Ile Glu Leu Thr Gln Ala Gly Leu Lys Gly Ser Thr Glu
785                 790                 795                 800

Gly Ser Glu Ser Tyr Glu Glu Asp Pro Tyr Leu Val Val Asn Pro Asn
            805                 810                 815

Tyr Leu Leu Glu Asp
            820
```

<210> SEQ ID NO 33
<211> LENGTH: 2111
<212> TYPE: DNA
<213> ORGANISM: Homo sapiens

<400> SEQUENCE: 33

| | | | | | |
|---|---|---|---|---|---|
| ggccggccac | tcccgtctgc | tgtgacgcgc | ggacagagag | ctaccggtgg | acccacggtg | 60 |
| cctccctccc | tgggatctac | acagaccatg | gccttgccaa | cggctcgacc | cctgttgggg | 120 |
| tcctgtggga | cccccgccct | cggcagcctc | ctgttcctgc | tcttcagcct | cggatgggtg | 180 |
| cagccctcga | ggaccctggc | tggagagaca | gggcaggagg | ctgcacccct | ggacggagtc | 240 |
| ctggccaacc | cacctaacat | ttccagcctc | tcccctcgcc | aactccttgg | cttcccgtgt | 300 |
| gcggaggtgt | ccggcctgag | cacggagcgt | gtccgggagc | tggctgtggc | cttggcacag | 360 |
| aagaatgtca | agctctcaac | agagcagctg | cgctgtctgg | ctcaccggct | ctctgagccc | 420 |
| cccgaggacc | tggacgccct | cccattggac | ctgctgctat | tcctcaaccc | agatgcgttc | 480 |
| tcggggcccc | aggcctgcac | ccgtttcttc | tcccgcatca | cgaaggccaa | tgtggacctg | 540 |
| ctcccgaggg | gggctcccga | gcgacagcgg | ctgctgcctg | cggctctggc | ctgctggggt | 600 |
| gtgcggggt | ctctgctgag | cgaggctgat | gtgcgggctc | tgggaggcct | ggcttgcgac | 660 |
| ctgcctgggc | gctttgtggc | cgagtcggcc | gaagtgctgc | tacccggct | ggtgagctgc | 720 |
| ccgggacccc | tggaccagga | ccagcaggag | gcagccaggg | cggctctgca | gggcggggga | 780 |
| cccccctacg | gccccccgtc | gacatggtct | gtctccacga | tggacgctct | gcggggcctg | 840 |
| ctgcccgtgc | tgggccagcc | catcatccgc | agcatcccgc | agggcatcgt | ggccgcgtgg | 900 |
| cggcaacgct | cctctcggga | cccatcctgg | cggcagcctg | aacggaccat | cctccggccg | 960 |
| cggttccggc | gggaagtgga | gaagacagcc | tgtccttcag | gcaagaaggc | ccgcgagata | 1020 |
| gacgagagcc | tcatcttcta | caagaagtgg | gagctggaag | cctgcgtgga | tgcggccctg | 1080 |
| ctggccaccc | agatggaccg | cgtgaacgcc | atccccttca | cctacgagca | gctggacgtc | 1140 |
| ctaaagcata | aactggatga | gctctaccca | caaggttacc | ccgagtctgt | gatccagcac | 1200 |
| ctgggctacc | tcttcctcaa | gatgagccct | gaggacattg | caagtggaa | tgtgacgtcc | 1260 |
| ctggagaccc | tgaaggcttt | gcttgaagtc | aacaaagggc | acgaaatgag | tcctcaggtg | 1320 |
| gccaccctga | tcgaccgctt | tgtgaaggga | aggggccagc | tagacaaaga | caccctagac | 1380 |
| accctgaccg | ccttctaccc | tgggtacctg | tgctccctca | gccccgagga | gctgagctcc | 1440 |
| gtgccccca | gcagcatctg | gcggtcagg | cccaggacc | tggacgcgtg | tgacccaagg | 1500 |
| cagctggacg | tcctctatcc | caaggcccgc | cttgctttcc | agaacatgaa | cgggtccgaa | 1560 |
| tacttcgtga | agatccagtc | cttcctgggt | ggggccccca | cggaggattt | gaaggcgctc | 1620 |
| agtcagcaga | atgtgagcat | ggacttggcc | acgttcatga | agctgcggac | ggatgcggtg | 1680 |
| ctgccgttga | ctgtggctga | ggtgcagaaa | cttctggac | cccacgtgga | gggcctgaag | 1740 |
| gcggaggagc | ggcaccgccc | ggtgcgggac | tggatcctac | ggcagcggca | ggacgacctg | 1800 |
| gacacgctgg | ggctgggct | acagggcgg | atccccaacg | ctacctggt | cctagacctc | 1860 |
| agcgtgcaag | aggccctctc | ggggacgccc | tgcctcctag | gacctggacc | tgttctcacc | 1920 |
| gtcctggcac | tgctcctagc | ctccaccctg | gcctgagggc | cccactccct | tgctggcccc | 1980 |
| agccctgctg | gggatccccg | cctggccagg | agcaggcacg | ggtgatcccc | gttccacccc | 2040 |
| aagagaactc | gcgctcagta | aacgggaaca | tgccccctgc | agacacgtaa | aaaaaaaaa | 2100 |
| aaaaaaaaaa | a | | | | | 2111 |

-continued

<210> SEQ ID NO 34
<211> LENGTH: 622
<212> TYPE: PRT
<213> ORGANISM: Homo sapiens

<400> SEQUENCE: 34

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile

```
                  370                 375                 380
Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
        595                 600                 605

Val Leu Thr Val Leu Ala Leu Leu Ala Ser Thr Leu Ala
610                 615                 620

<210> SEQ ID NO 35
<211> LENGTH: 2731
<212> TYPE: DNA
<213> ORGANISM: Homo sapiens

<400> SEQUENCE: 35
gcgcttggcg ggagatagaa aagtgcttca acccgcgccg gcggcgactg cagttcctgc      60
gagcgaggag cgcgggacct gctgacacgc tgacgccttc gagcgcggcc cggggcccgg     120
agcggccgga gcagcccggg tcctgacccc ggcccggctc ccgctccggg ctctgccggc     180
gggcgggcga gcgcggcgcg gtccgggccg gggggatgtc tcggcggacg cgctgcgagg     240
atctggatga gctgcactac caggacacag attcagatgt gccggagcag agggatagca     300
agtgcaaggt caaatggacc catgaggagg acgagcagct gagggccctg gtgaggcagt     360
ttggacagca ggactggaag ttcctggcca gccacttccc taaccgcact gaccagcaat     420
gccagtacag gtggctgaga gttttgaatc cagaccttgt caaggggcca tggaccaaag     480
aggaagacca aaaagtcatc gagctggtta agaagtatgg cacaaagcag tggacactga     540
ttgccaagca cctgaagggc cggctgggga gcagtgccg tgaacgctgg cacaaccacc     600
tcaaccctga ggtgaagaag tcttgctgga ccgaggagga ggaccgcatc atctgcgagg     660
cccacaaggt gctgggcaac cgctgggccg agatcgccaa gatgttgcca gggaggacag     720
```

```
acaatgctgt gaagaatcac tggaactcta ccatcaaaag gaaggtgac  acaggaggct      780 tcttgagcga gtccaaagac tgcaagcccc cagtgtactt gctgctggag ctcgaggaca      840
aggacggcct ccagagtgcc cagcccacgg aaggccaggg aagtcttctg accaactggc      900
cctccgtccc tcctaccata aggaggagg  aaaacagtga ggaggaactt gcagcagcca      960
ccacatcgaa ggaacaggag cccatcggta cagatctgga cgcagtgcga acaccagagc     1020
ccttggagga attcccgaag cgtgaggacc aggaaggctc cccaccagaa cgagcctgc      1080 cttacaagtg ggtggtggag gcagctaacc tcctcatccc cgctgtgggt tctagcctct     1140
ctgaagccct ggacttgatc gagtcggacc ctgatgcttg gtgtgacctg agtaaatttg     1200
acctccctga ggaaccatct gcagaggaca gtatcaacaa cagcctagtg cagctgcaag     1260
cgtcacatca gcagcaagtc ctgccacccc gccagccttc cgcctggtg cccagtgtga      1320 ccgagtaccg cctggatggc cacaccatct cagacctgag ccggagcagc cggggcgagc     1380
tgatccccat ctcccccagc actgaagtcg ggggctctgg cattggcaca ccgccctctg     1440
tgctcaagcg gcagaggaag aggcgtgtgg ctctgtcccc tgtcactgag aatagcacca     1500
gtctgtcctt cctggattcc tgtaacagcc tcacgcccaa gagcacacct gttaagaccc     1560
tgcccttctc gccctcccag tttctgaact tctggaacaa acaggacaca ttggagctgg     1620 agagccctc  gctgacatcc accccagtgt gcagccagaa ggtggtggtc accacaccac     1680
tgcaccggga caagacaccc ctgcaccaga acatgctgc  gtttgtaacc ccagatcaga     1740
agtactccat ggacaacact ccccacacgc caaccccgtt caagaacgcc ctggagaagt     1800 acggaccct  gaagcccctg ccacagaccc cgcacctgga ggaggacttg aaggaggtgc     1860
tgcgttctga ggctggcatc gaactcatca tcgaggacga catcaggccc gagaagcaga     1920
agaggaagcc tgggctgcgg cggagcccca tcaagaaagt ccggaagtct ctggctcttg     1980
acattgtgga tgaggatgtg aagctgatga tgtccacact gcccaagtct ctatccttgc     2040
cgacaactgc cccttcaaac tcttccagcc tcaccctgtc aggtatcaaa gaagacaaca     2100
gcttgctcaa ccagggcttc ttgcaggcca agcccgagaa ggcagcagtg gcccagaagc     2160
cccgaagcca cttcacgaca cctgccccta tgtccagtgc ctggaagacg gtggcctgcg     2220
gggggaccag ggaccagctt ttcatgcagg agaaagcccg gcagctcctg ggccgcctga     2280
agcccagcca cacatctcgg accctcatct tgtcctgagg tgttgagggt gtcacgagcc     2340
cattctcatg tttacagggg ttgtgggggc agagggggtc tgtgaatctg agagtcattc     2400
aggtgacctc ctgcagggag ccttctgcca ccagcccctc cccagactct caggtggagg     2460
caacagggcc atgtgctgcc ctgttgccga gcccagctgt gggcggctcc tggtgctaac     2520
aacaaagttc cacttccagg tctgcctggt tccctcccca aggccacagg agctccgtc      2580 agcttctccc aagcccacgt caggcctggc ctcatctcag accctgctta ggatggggga     2640
tgtggccagg ggtgctcctg tgctcaccct tcttggtgc  atttttttgg aagaataaaa     2700
ttgcctctct cttaaaaaaa aaaaaaaaaa a                                    2731
```

<210> SEQ ID NO 36
<211> LENGTH: 700
<212> TYPE: PRT
<213> ORGANISM: Homo sapiens

<400> SEQUENCE: 36

```
Met Ser Arg Arg Thr Arg Cys Glu Asp Leu Asp Glu Leu His Tyr Gln
1               5                   10                  15
```

-continued

```
Asp Thr Asp Ser Asp Val Pro Glu Gln Arg Asp Ser Lys Cys Lys Val
             20                  25                  30

Lys Trp Thr His Glu Glu Asp Glu Gln Leu Arg Ala Leu Val Arg Gln
         35                  40                  45

Phe Gly Gln Gln Asp Trp Lys Phe Leu Ala Ser His Phe Pro Asn Arg
     50                  55                  60

Thr Asp Gln Gln Cys Gln Tyr Arg Trp Leu Arg Val Leu Asn Pro Asp
 65                  70                  75                  80

Leu Val Lys Gly Pro Trp Thr Lys Glu Glu Asp Gln Lys Val Ile Glu
                 85                  90                  95

Leu Val Lys Lys Tyr Gly Thr Lys Gln Trp Thr Leu Ile Ala Lys His
            100                 105                 110

Leu Lys Gly Arg Leu Gly Lys Gln Cys Arg Glu Arg Trp His Asn His
        115                 120                 125

Leu Asn Pro Glu Val Lys Lys Ser Cys Trp Thr Glu Glu Glu Asp Arg
130                 135                 140

Ile Ile Cys Glu Ala His Lys Val Leu Gly Asn Arg Trp Ala Glu Ile
145                 150                 155                 160

Ala Lys Met Leu Pro Gly Arg Thr Asp Asn Ala Val Lys Asn His Trp
                165                 170                 175

Asn Ser Thr Ile Lys Arg Lys Val Asp Thr Gly Gly Phe Leu Ser Glu
            180                 185                 190

Ser Lys Asp Cys Lys Pro Pro Val Tyr Leu Leu Glu Leu Glu Asp
        195                 200                 205

Lys Asp Gly Leu Gln Ser Ala Gln Pro Thr Glu Gly Gln Gly Ser Leu
210                 215                 220

Leu Thr Asn Trp Pro Ser Val Pro Pro Thr Ile Lys Glu Glu Asn
225                 230                 235                 240

Ser Glu Glu Glu Leu Ala Ala Thr Thr Ser Lys Glu Gln Glu Pro
                245                 250                 255

Ile Gly Thr Asp Leu Asp Ala Val Arg Thr Pro Glu Pro Leu Glu Glu
            260                 265                 270

Phe Pro Lys Arg Glu Asp Gln Glu Gly Ser Pro Pro Glu Thr Ser Leu
        275                 280                 285

Pro Tyr Lys Trp Val Val Glu Ala Ala Asn Leu Leu Ile Pro Ala Val
    290                 295                 300

Gly Ser Ser Leu Ser Glu Ala Leu Asp Leu Ile Glu Ser Asp Pro Asp
305                 310                 315                 320

Ala Trp Cys Asp Leu Ser Lys Phe Asp Leu Pro Glu Pro Ser Ala
                325                 330                 335

Glu Asp Ser Ile Asn Asn Ser Leu Val Gln Leu Gln Ala Ser His Gln
            340                 345                 350

Gln Gln Val Leu Pro Pro Arg Gln Pro Ser Ala Leu Val Pro Ser Val
        355                 360                 365

Thr Glu Tyr Arg Leu Asp Gly His Thr Ile Ser Asp Leu Ser Arg Ser
    370                 375                 380

Ser Arg Gly Glu Leu Ile Pro Ile Ser Pro Ser Thr Glu Val Gly Gly
385                 390                 395                 400

Ser Gly Ile Gly Thr Pro Pro Ser Val Leu Lys Arg Gln Arg Lys Arg
                405                 410                 415

Arg Val Ala Leu Ser Pro Val Thr Glu Asn Ser Thr Ser Leu Ser Phe
            420                 425                 430

Leu Asp Ser Cys Asn Ser Leu Thr Pro Lys Ser Thr Pro Val Lys Thr
```

```
                435                 440                 445
Leu Pro Phe Ser Pro Ser Gln Phe Leu Asn Phe Trp Asn Lys Gln Asp
    450                 455                 460

Thr Leu Glu Leu Glu Ser Pro Ser Leu Thr Ser Thr Pro Val Cys Ser
465                 470                 475                 480

Gln Lys Val Val Thr Thr Pro Leu His Arg Asp Lys Thr Pro Leu
                485                 490                 495

His Gln Lys His Ala Ala Phe Val Thr Pro Asp Gln Lys Tyr Ser Met
            500                 505                 510

Asp Asn Thr Pro His Thr Pro Thr Pro Phe Lys Asn Ala Leu Glu Lys
        515                 520                 525

Tyr Gly Pro Leu Lys Pro Leu Pro Gln Thr Pro His Leu Glu Glu Asp
    530                 535                 540

Leu Lys Glu Val Leu Arg Ser Glu Ala Gly Ile Glu Leu Ile Ile Glu
545                 550                 555                 560

Asp Asp Ile Arg Pro Glu Lys Gln Lys Arg Lys Pro Gly Leu Arg Arg
                565                 570                 575

Ser Pro Ile Lys Lys Val Arg Lys Ser Leu Ala Leu Asp Ile Val Asp
            580                 585                 590

Glu Asp Val Lys Leu Met Met Ser Thr Leu Pro Lys Ser Leu Ser Leu
        595                 600                 605

Pro Thr Thr Ala Pro Ser Asn Ser Ser Ser Leu Thr Leu Ser Gly Ile
    610                 615                 620

Lys Glu Asp Asn Ser Leu Leu Asn Gln Gly Phe Leu Gln Ala Lys Pro
625                 630                 635                 640

Glu Lys Ala Ala Val Ala Gln Lys Pro Arg Ser His Phe Thr Thr Pro
                645                 650                 655

Ala Pro Met Ser Ser Ala Trp Lys Thr Val Ala Cys Gly Gly Thr Arg
            660                 665                 670

Asp Gln Leu Phe Met Gln Glu Lys Ala Arg Gln Leu Leu Gly Arg Leu
        675                 680                 685

Lys Pro Ser His Thr Ser Arg Thr Leu Ile Leu Ser
    690                 695                 700

<210> SEQ ID NO 37
<211> LENGTH: 2304
<212> TYPE: DNA
<213> ORGANISM: Homo sapiens

<400> SEQUENCE: 37
gtccccgcag cgccgtcgcg ccctcctgcc gcaggccacc gaggccgccg ccgtctagcg     60
ccccgacctc gccaccatga gagccctgct ggcgcgcctg cttctctgcg tcctggtcgt    120
gagcgactcc aaaggcagca atgaacttca tcaagttcca tcgaactgtg actgtctaaa    180
tggaggaaca tgtgtgtcca acaagtactt ctccaacatt cactggtgca actgcccaaa    240
gaaattcgga gggcagcact gtgaaataga taagtcaaaa acctgctatg aggggaatgg    300
tcacttttac cgaggaaagg ccagcactga caccatgggc cggccctgcc tgccctggaa    360
ctctgccact gtccttcagc aaacgtacca tgcccacaga tctgatgctc ttcagctggg    420
cctggggaaa cataattact gcaggaaccc agacaaccgg aggcgaccct ggtgctatgt    480
gcaggtgggc ctaaagccgc ttgtccaaga gtgcatggtg catgactgcg cagatggaaa    540
aaagccctcc tctcctccag aagaattaaa atttcagtgt ggccaaagag ctctgaggcc    600
ccgctttaag attattgggg gagaattcac caccatcgag aaccagccct ggtttgcggc    660
```

-continued

```
catctacagg aggcaccggg ggggctctgt cacctacgtg tgtggaggca gcctcatcag      720
cccttgctgg gtgatcagcg ccacacactg cttcattgat tacccaaaga aggaggacta      780
catcgtctac ctgggtcgct caaggcttaa ctccaacacg caaggggaga tgaagtttga      840
ggtggaaaac ctcatcctac acaaggacta cagcgctgac acgcttgctc accacaacga      900
cattgccttg ctgaagatcc gttccaagga gggcaggtgt gcgcagccat cccgactat       960 acagaccatc tgcctgccct cgatgtataa cgatcccag  tttggcacaa gctgtgagat     1020
cactggcttt ggaaaagaga attctaccga ctatctctat ccggagcagc tgaaaatgac     1080
tgttgtgaag ctgatttccc accgggagtg tcagcagccc cactactacg gctctgaagt     1140
caccaccaaa atgctatgtg ctgctgaccc caatggaaaa acagattcct gccagggaga     1200
ctcaggggga cccctcgtct gttccctcca aggccgcatg actttgactg gaattgtgag     1260 ctgggggccgt ggatgtgccc tgaaggacaa gccaggcgtc tacacagagag tctcacactt    1320 cttaccctgg atccgcagtc acaccaagga agagaatggc ctggccctct gagggtcccc     1380
agggaggaaa cgggcaccac ccgctttctt gctggttgtc attttttgcag tagagtcatc     1440 tccatcagct gtaagaagag actgggaaga taggctctgc acagatggat ttgcctgtgg     1500
caccaccagg gtgaacgaca atagctttac cctcacggat aggcctgggt gctggctgcc     1560
cagaccctct ggccaggatg gagggtggt  cctgactcaa catgttactg accagcaact     1620
tgtctttttc tggactgaag cctgcaggag ttaaaaaggg cagggcatct cctgtgcatg     1680
ggctcgaagg gagagccagc tcccccgacc ggtgggcatt tgtgaggccc atggttgaga     1740
aatgaataat ttcccaatta ggaagtgtaa gcagctgagg tctcttgagg gagcttagcc     1800
aatgtgggag cagcggtttg gggagcagag acactaacga cttcagggca gggctctgat     1860
attccatgaa tgtatcagga aatatatatg tgtgtgtatg tttgcacact tgttgtgtgg     1920
gctgtgagtg taagtgtgag taagagctgg tgtctgattg ttaagtctaa atatttcctt     1980
aaactgtgtg gactgtgatg ccacacagag tggtctttct ggagaggtta taggtcactc     2040
ctggggcctc ttgggtcccc cacgtgacag tgcctgggaa tgtacttatt ctgcagcatg     2100
acctgtgacc agcactgtct cagtttcact ttcacataga tgtcccttttc ttggccagtt    2160 atcccttcct tttagcctag ttcatccaat cctcactggg tggggtgagg accactcctt     2220
acactgaata tttatatttc actatttta  tttatatttt tgtaattttta aataaaagtg    2280 atcaataaaa tgtgattttt ctga                                            2304
```

<210> SEQ ID NO 38
<211> LENGTH: 431
<212> TYPE: PRT
<213> ORGANISM: Homo sapiens

<400> SEQUENCE: 38

```
Met Arg Ala Leu Leu Ala Arg Leu Leu Leu Cys Val Leu Val Val Ser
 1               5                  10                  15

Asp Ser Lys Gly Ser Asn Glu Leu His Gln Val Pro Ser Asn Cys Asp
            20                  25                  30

Cys Leu Asn Gly Gly Thr Cys Val Ser Asn Lys Tyr Phe Ser Asn Ile
        35                  40                  45

His Trp Cys Asn Cys Pro Lys Lys Phe Gly Gly Gln His Cys Glu Ile
    50                  55                  60

Asp Lys Ser Lys Thr Cys Tyr Glu Gly Asn Gly His Phe Tyr Arg Gly
65                  70                  75                  80
```

```
Lys Ala Ser Thr Asp Thr Met Gly Arg Pro Cys Leu Pro Trp Asn Ser
                 85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
                180                 185                 190

Phe Ala Ala Ile Tyr Arg Arg His Arg Gly Gly Ser Val Thr Tyr Val
            195                 200                 205

Cys Gly Gly Ser Leu Ile Ser Pro Cys Trp Val Ile Ser Ala Thr His
        210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
                260                 265                 270

His Asn Asp Ile Ala Leu Leu Lys Ile Arg Ser Lys Glu Gly Arg Cys
            275                 280                 285

Ala Gln Pro Ser Arg Thr Ile Gln Thr Ile Cys Leu Pro Ser Met Tyr
        290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
    370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
                405                 410                 415

Pro Trp Ile Arg Ser His Thr Lys Glu Glu Asn Gly Leu Ala Leu
                420                 425                 430

<210> SEQ ID NO 39
<211> LENGTH: 1760
<212> TYPE: DNA
<213> ORGANISM: Homo sapiens

<400> SEQUENCE: 39
gcagcaggcc aagggggagg tgcgagcgtg gacctgggac gggtctgggc ggctctcggt    60
ggttggcacg ggttcgcaca cccattcaag cggcaggacg cacttgtctt agcagttctc   120
```

-continued

```
gctgaccgcg ctagctgcgg cttctacgct ccggcactct gagttcatca gcaaacgccc    180
tggcgtctgt cctcaccatg cctagccttt gggaccgctt ctcgtcgtcg tccacctcct    240
cttcgccctc gtccttgccc cgaactccca ccccagatcg gccgccgcgc tcagcctggg    300
ggtcggcgac ccgggaggag gggtttgacc gctccacgag cctggagagc tcggactgcg    360
agtccctgga cagcagcaac agtggcttcg gccggagga agacacggct tacctggatg    420
gggtgtcgtt gcccgacttc gagctgctca gtgaccctga ggatgaacac ttgtgtgcca    480
acctgatgca gctgctgcag gagagcctgg cccaggcgcg gctgggctct cgacgccctg    540
cgcgcctgct gatgcctagc cagttggtaa gccaggtggg caaagaacta ctgcgcctgg    600
cctacagcga gccgtgcggc ctgcgggggg cgctgctgga cgtctgcgtg gagcagggca    660
agagctgcca cagcgtgggc cagctggcac tcgaccccag cctggtgccc accttccagc    720
tgaccctcgt gctgcgcctg gactcacgac tctggcccaa gatccagggg ctgtttagct    780
ccgccaactc tccttcctc cctggcttca gccagtccct gacgctgagc actggcttcc    840
gagtcatcaa gaagaagctg tacagctcgg aacagctgct cattgaggag tgttgaactt    900
caacctgagg gggccgacag tgccctccaa gacagagacg actgaacttt tggggtggag    960
actagaggca ggagctgagg gactgattcc agtggttgga aaactgaggc agccacctaa   1020
ggtggaggtg ggggaatagt gtttcccagg aagctcattg agttgtgtgc gggtggctgt   1080
gcattgggga cacataccc tcagtactgt agcatggaac aaaggcttag gggccaacaa   1140
ggcttccagc tggatgtgtg tgtagcatgt accttattat ttttgttact gacagttaac   1200
agtggtgtga catccagaga gcagctgggc tgctcccgcc ccagcctggc ccagggtgaa   1260
ggaagaggca cgtgctcctc agagcagccg gagggagggg ggaggtcgga ggtcgtggag   1320
gtggtttgtg tatcttactg gtctgaaggg accaagtgtg tttgttgttt gttttgtatc   1380
ttgtttttct gatcggagca tcactactga cctgttgtag gcagctatct tacagacgca   1440
tgaatgtaag agtaggaagg ggtgggtgtc agggatcact tgggatcttt gacacttgaa   1500
aaattacacc tggcagctgc gtttaagcct tcccccatcg tgtactgcag agttgagctg   1560 gcagggagg ggctgagagg gtggggctg gaacccctcc ccgggaggag tgccatctgg   1620
gtcttccatc tagaactgtt tacatgaaga taagatactc actgttcatg aatacacttg   1680
atgttcaagt attaagacct atgcaatatt ttttacttt ctaataaaca tgtttgttaa   1740
aacaaaaaaa aaaaaaaaa                                                 1760
```

<210> SEQ ID NO 40
<211> LENGTH: 232
<212> TYPE: PRT
<213> ORGANISM: Homo sapiens

<400> SEQUENCE: 40

```
Met Pro Ser Leu Trp Asp Arg Phe Ser Ser Ser Thr Ser Ser Ser
 1               5                  10                  15

Pro Ser Ser Leu Pro Arg Thr Pro Thr Pro Asp Arg Pro Pro Arg Ser
                20                  25                  30

Ala Trp Gly Ser Ala Thr Arg Glu Glu Gly Phe Asp Arg Ser Thr Ser
            35                  40                  45

Leu Glu Ser Ser Asp Cys Glu Ser Leu Asp Ser Ser Asn Ser Gly Phe
        50                  55                  60

Gly Pro Glu Glu Asp Thr Ala Tyr Leu Asp Gly Val Ser Leu Pro Asp
65                  70                  75                  80
```

```
Phe Glu Leu Leu Ser Asp Pro Glu Asp Glu His Leu Cys Ala Asn Leu
                85                  90                  95
Met Gln Leu Leu Gln Glu Ser Leu Ala Gln Ala Arg Leu Gly Ser Arg
            100                 105                 110
Arg Pro Ala Arg Leu Leu Met Pro Ser Gln Leu Val Ser Gln Val Gly
        115                 120                 125
Lys Glu Leu Leu Arg Leu Ala Tyr Ser Glu Pro Cys Gly Leu Arg Gly
    130                 135                 140
Ala Leu Leu Asp Val Cys Val Glu Gln Gly Lys Ser Cys His Ser Val
145                 150                 155                 160
Gly Gln Leu Ala Leu Asp Pro Ser Leu Val Pro Thr Phe Gln Leu Thr
                165                 170                 175
Leu Val Leu Arg Leu Asp Ser Arg Leu Trp Pro Lys Ile Gln Gly Leu
            180                 185                 190
Phe Ser Ser Ala Asn Ser Pro Phe Leu Pro Gly Phe Ser Gln Ser Leu
        195                 200                 205
Thr Leu Ser Thr Gly Phe Arg Val Ile Lys Lys Lys Leu Tyr Ser Ser
    210                 215                 220
Glu Gln Leu Leu Ile Glu Glu Cys
225                 230

<210> SEQ ID NO 41
<211> LENGTH: 5698
<212> TYPE: DNA
<213> ORGANISM: Homo sapiens

<400> SEQUENCE: 41
```

| | | | | | |
|---|---|---|---|---|---|
| aggttcaagt | ggagctctcc | taaccgacgc | gcgtctgtgg | agaagcggct | tggtcggggg | 60 |
| tggtctcgtg | gggtcctgcc | tgtttagtcg | ctttcagggt | tcttgagccc | cttcacgacc | 120 |
| gtcaccatgg | aagtgtcacc | attgcagcct | gtaaatgaaa | atatgcaagt | caacaaaata | 180 |
| aagaaaaatg | aagatgctaa | gaaaagactg | tctgttgaaa | gaatctatca | aagaaaaca | 240 |
| caattggaac | atattttgct | ccgcccagac | acctacattg | gttctgtgga | attagtgacc | 300 |
| cagcaaatgt | gggtttacga | tgaagatgtt | ggcattaact | atagggaagt | cacttttgtt | 360 |
| cctggtttgt | acaaaatctt | tgatgagatt | ctagttaatg | ctgcggacaa | caaacaaagg | 420 |
| gacccaaaaa | tgtcttgtat | tagagtcaca | attgatccgg | aaaacaattt | aattagtata | 480 |
| tggaataatg | aaaaggtat | tcctgttgtt | gaacacaaag | ttgaaaagat | gtatgtccca | 540 |
| gctctcatat | ttggacagct | cctaacttct | agtaactatg | atgatgatga | aaagaaagtg | 600 |
| acaggtggtc | gaaatggcta | tggagccaaa | ttgtgtaaca | tattcagtac | caaatttact | 660 |
| gtggaaacag | ccagtagaga | atacaagaaa | atgttcaaac | agacatggat | ggataatatg | 720 |
| ggaagagctg | gtgagatgga | actcaagccc | tcaatggag | aagattatac | atgtatcacc | 780 |
| tttcagcctg | atttgtctaa | gtttaaaatg | caaagcctgg | acaaagatat | tgttgcacta | 840 |
| atggtcagaa | gagcatatga | tattgctgga | tccaccaaag | atgtcaaagt | ctttcttaat | 900 |
| ggaaataaac | tgccagtaaa | aggatttcgt | agttatgtgg | acatgtattt | gaaggacaag | 960 |
| ttggatgaaa | ctggtaactc | cttgaaagta | atacatgaac | aagtaaacca | caggtgggaa | 1020 |
| gtgtgtttaa | ctatgagtga | aaaggctttt | cagcaaatta | gctttgtcaa | cagcattgct | 1080 |
| acatccaagg | gtggcagaca | tgttgattat | gtagctgatc | agattgtgac | taaacttgtt | 1140 |
| gatgttgtga | agaagaagaa | caagggtggt | gttgcagtaa | aagcacatca | ggtgaaaaat | 1200 |
| cacatgtgga | ttttttgtaaa | tgccttaatt | gaaaaacccaa | cctttgactc | tcagacaaaa | 1260 |

```
gaaaacatga ctttacaacc caagagcttt ggatcaacat gccaattgag tgaaaaattt   1320
atcaaagctg ccattggctg tggtattgta gaaagcatac taaactgggt gaagtttaag   1380
gcccaagtcc agttaaacaa gaagtgttca gctgtaaaac ataatagaat caagggaatt   1440
cccaaactcg atgatgccaa tgatgcaggg ggccgaaact ccactgagtg tacgcttatc   1500
ctgactgagg gagattcagc caaaactttg gctgtttcag gccttggtgt ggttgggaga   1560
gacaaatatg gggttttccc tcttagagga aaaatactca atgttcgaga agcttctcat   1620
aagcagatca tggaaaatgc tgagattaac aatatcatca agattgtggg tcttcagtac   1680
aagaaaaact atgaagatga agattcattg aagacgcttc gttatgggaa gataatgatt   1740
atgacagatc aggaccaaga tggttccac atcaaaggct tgctgattaa ttttatccat   1800
cacaactggc cctctcttct gcgacatcgt tttctggagg aatttatcac tcccattgta   1860
aaggtatcta aaaacaagca agaaatggca ttttacagcc ttcctgaatt tgaagagtgg   1920
aagagttcta ctccaaatca taaaaaatgg aaagtcaaat attacaaagg tttgggcacc   1980
agcacatcaa aggaagctaa agaatacttt gcagatatga aaagacatcg tatccagttc   2040
aaatattctg gtcctgaaga tgatgctgct atcagcctgg cctttagcaa aaaacagata   2100
gatgatcgaa aggaatggtt aactaatttc atggaggata gaagcaacg aaagttactt   2160
gggcttcctg aggattactt gtatggacaa actaccacat atctgacata taatgacttc   2220
atcaacaagg aacttatctt gttctcaaat tctgataacg agagatctat cccttctatg   2280
gtggatggtt tgaaaccagg tcagagaaag gttttgttta cttgcttcaa acggaatgac   2340
aagcgagaag taaaggttgc ccaattagct ggatcagtgg ctgaaatgtc ttcttatcat   2400
catggtgaga tgtcactaat gatgaccatt atcaatttgg ctcagaattt tgtgggtagc   2460
aataatctaa acctcttgca gcccattggt cagtttggta ccaggctaca tggtggcaag   2520
gattctgcta gtccacgata catctttaca atgctcagct cttttggctcg attgttattt   2580
ccaccaaaag atgatcacac gttgaagttt ttatatgatg acaaccagcg tgttgagcct   2640
gaatggtaca ttcctattat tcccatggtg ctgataaatg gtgctgaagg aatcggtact   2700
gggtggtcct gcaaaatccc caactttgat gtgcgtgaaa ttgtaaataa catcaggcgt   2760
tgatggatg gagaagaacc tttgccaatg cttccaagtt acaagaactt caagggtact   2820
attgaagaac tggctccaaa tcaatatgtg attagtggtg aagtagctat tcttaattct   2880
acaaccattg aaatctcaga gcttcccgtc agaacatgga cccagacata caagaacaa   2940
gttctagaac ccatgttgaa tggcaccgag aagacacctc ctctcataac agactatagg   3000
gaataccata cagataccac tgtgaaattt gttgtgaaga tgactgaaga aaaactggca   3060
gaggcagaga gagttggact acacaaagtc ttcaaactcc aaactagtct cacatgcaac   3120
tctatggtgc ttttttgacca cgtaggctgt ttaaagaaat atgacacggt gttggatatt   3180
ctaagagact tttttgaact cagacttaaa tattatggat taagaaaaga atggctccta   3240
ggaatgcttg tgtctgaatc tgctaaactg aataatcagg ctcgctttat cttagagaaa   3300
atagatggca aaataatcat tgaaaataag cctaagaaag aattaattaa agttctgatt   3360
cagaggggat atgattcgga tcctgtgaag gcctggaaag aagcccagca aaaggttcca   3420
gatgaagaag aaaatgaaga gagtgacaac gaaaaggaaa ctgaaaagag tgactccgta   3480
acagattctg gaccaacctt caactatctt cttgatatgc ccctttggta tttaaccaag   3540
gaaaagaaag atgaactctg caggctaaga aatgaaaaag aacaagagct ggacacatta   3600
```

```
aaaagaaaga gtccatcaga tttgtggaaa gaagacttgg ctacatttat tgaagaattg    3660
gaggctgttg aagccaagga aaacaagat gaacaagtcg gacttcctgg gaaggggggg    3720
aaggccaagg ggaaaaaaac acaaatggct gaagttttgc cttctccgcg tggtcaaaga    3780
gtcattccac gaataaccat agaaatgaaa gcagaggcag aaaagaaaaa taaaaagaaa    3840
attaagaatg aaaatactga aggaagccct caagaagatg gtgtggaact agaaggccta    3900
aaacaaagat tagaaaagaa acagaaaaga gaaccaggta caaagacaaa gaaacaaact    3960
acattggcat ttaagccaat caaaaaagga agaagagaaa tccctggtc tgattcagaa     4020 tcagatagga gcagtgacga aagtaatttt gatgtccctc cacgagaaac agagccacgg    4080
agagcagcaa caaaaacaaa attcacaatg gatttggatt cagatgaaga tttctcagat    4140
tttgatgaaa aaactgatga tgaagatttt gtcccatcag atgctagtcc acctaagacc    4200
aaaacttccc caaaacttag taacaaagaa ctgaaaccac agaaaagtgt cgtgtcagac    4260
cttgaagctg atgatgttaa gggcagtgta ccactgtctt caagccctcc tgctacacat    4320
ttcccagatg aaactgaaat tacaaaccca gttcctaaaa agaatgtgac agtgaagaag    4380
acagcagcaa aaagtcagtc ttccacctcc actaccggtg ccaaaaaaag ggctgcccca    4440
aaaggaacta aaagggatcc agctttgaat tctggtgtct ctcaaaagcc tgatcctgcc    4500
aaaaccaaga atcgccgcaa aaggaagcca tccacttctg atgattctga ctctaatttt    4560
gagaaaattg tttcgaaagc agtcacaagc aagaaatcca aggggagag tgatgacttc    4620 catatggact ttgactcagc tgtggctcct cgggcaaaat ctgtacgggc aaagaaacct    4680
ataaagtacc tggaagagtc agatgaagat gatctgtttt aaaatgtgag gcgattattt    4740
taagtaatta tcttaccaag cccaagactg gttttaaagt tacctgaagc tcttaacttc    4800
ctcccctctg aatttagttt ggggaaggtg tttttagtac aagacatcaa agtgaagtaa    4860
agcccaagtg ttctttagct ttttataata ctgtctaaat agtgaccatc tcatgggcat    4920
tgttttcttc tctgctttgt ctgtgttttg agtctgcttt cttttgtctt taaaacctga    4980
tttttaagtt cttctgaact gtagaaatag ctatctgatc acttcagcgt aaagcagtgt    5040
gtttattaac catccactaa gctaaaacta gagcagtttg atttaaaagt gtcactcttc    5100 ctcctttttct actttcagta gatatgagat agagcataat tatctgtttt atcttagttt    5160
tatacataat ttaccatcag atagaacttt atggttctag tacagatact ctactacact    5220
cagcctctta tgtgccaagt ttttctttaa gcaatgagaa attgctcatg ttcttcatct    5280
tctcaaatca tcagaggcca agaaaaaaca ctttggctgt gtctataact tgacacagtc    5340
aatagaatga agaaaattag agtagttatg tgattatttc agctcttgac ctgtcccctc    5400
tggctgcctc tgagtctgaa tctcccaaag agagaaacca atttctaaga ggactggatt    5460
gcagaagact cggggacaac atttgatcca agatcttaaa tgttatattg ataaccatgc    5520
tcagcaatga gctattagat tcattttggg aaatctccat aatttcaatt tgtaaacttt    5580
gttaagacct gtctacattg ttatatgtgt gtgacttgag taatgttatc aacgttttg    5640 taaatattta ctatgttttt ctattagcta aattccaaca attttgtact ttaataaa    5698
```

<210> SEQ ID NO 42
<211> LENGTH: 1531
<212> TYPE: PRT
<213> ORGANISM: Homo sapiens

<400> SEQUENCE: 42

Met Glu Val Ser Pro Leu Gln Pro Val Asn Glu Asn Met Gln Val Asn

-continued

```
  1               5                  10                 15
Lys Ile Lys Lys Asn Glu Asp Ala Lys Arg Leu Ser Val Glu Arg
                 20                 25                 30

Ile Tyr Gln Lys Lys Thr Gln Leu Glu His Ile Leu Leu Arg Pro Asp
                 35                 40                 45

Thr Tyr Ile Gly Ser Val Glu Leu Val Thr Gln Gln Met Trp Val Tyr
 50                  55                 60

Asp Glu Asp Val Gly Ile Asn Tyr Arg Glu Val Thr Phe Val Pro Gly
 65                  70                 75                 80

Leu Tyr Lys Ile Phe Asp Glu Ile Leu Val Asn Ala Ala Asp Asn Lys
                 85                 90                 95

Gln Arg Asp Pro Lys Met Ser Cys Ile Arg Val Thr Ile Asp Pro Glu
                100                105                110

Asn Asn Leu Ile Ser Ile Trp Asn Asn Gly Lys Gly Ile Pro Val Val
                115                120                125

Glu His Lys Val Glu Lys Met Tyr Val Pro Ala Leu Ile Phe Gly Gln
                130                135                140

Leu Leu Thr Ser Ser Asn Tyr Asp Asp Asp Glu Lys Lys Val Thr Gly
145                150                155                160

Gly Arg Asn Gly Tyr Gly Ala Lys Leu Cys Asn Ile Phe Ser Thr Lys
                165                170                175

Phe Thr Val Glu Thr Ala Ser Arg Glu Tyr Lys Lys Met Phe Lys Gln
                180                185                190

Thr Trp Met Asp Asn Met Gly Arg Ala Gly Glu Met Glu Leu Lys Pro
                195                200                205

Phe Asn Gly Glu Asp Tyr Thr Cys Ile Thr Phe Gln Pro Asp Leu Ser
                210                215                220

Lys Phe Lys Met Gln Ser Leu Asp Lys Asp Ile Val Ala Leu Met Val
225                230                235                240

Arg Arg Ala Tyr Asp Ile Ala Gly Ser Thr Lys Asp Val Lys Val Phe
                245                250                255

Leu Asn Gly Asn Lys Leu Pro Val Lys Gly Phe Arg Ser Tyr Val Asp
                260                265                270

Met Tyr Leu Lys Asp Lys Leu Asp Glu Thr Gly Asn Ser Leu Lys Val
                275                280                285

Ile His Glu Gln Val Asn His Arg Trp Glu Val Cys Leu Thr Met Ser
                290                295                300

Glu Lys Gly Phe Gln Gln Ile Ser Phe Val Asn Ser Ile Ala Thr Ser
305                310                315                320

Lys Gly Gly Arg His Val Asp Tyr Val Ala Asp Gln Ile Val Thr Lys
                325                330                335

Leu Val Asp Val Val Lys Lys Asn Lys Gly Gly Val Ala Val Lys
                340                345                350

Ala His Gln Val Lys Asn His Met Trp Ile Phe Val Asn Ala Leu Ile
                355                360                365

Glu Asn Pro Thr Phe Asp Ser Gln Thr Lys Glu Asn Met Thr Leu Gln
                370                375                380

Pro Lys Ser Phe Gly Ser Thr Cys Gln Leu Ser Glu Lys Phe Ile Lys
385                390                395                400

Ala Ala Ile Gly Cys Gly Ile Val Glu Ser Ile Leu Asn Trp Val Lys
                405                410                415

Phe Lys Ala Gln Val Gln Leu Asn Lys Lys Cys Ser Ala Val Lys His
                420                425                430
```

-continued

```
Asn Arg Ile Lys Gly Ile Pro Lys Leu Asp Asp Ala Asn Asp Ala Gly
            435                 440                 445

Gly Arg Asn Ser Thr Glu Cys Thr Leu Ile Leu Thr Glu Gly Asp Ser
        450                 455                 460

Ala Lys Thr Leu Ala Val Ser Gly Leu Gly Val Val Gly Arg Asp Lys
465                 470                 475                 480

Tyr Gly Val Phe Pro Leu Arg Gly Lys Ile Leu Asn Val Arg Glu Ala
                485                 490                 495

Ser His Lys Gln Ile Met Glu Asn Ala Glu Ile Asn Asn Ile Ile Lys
            500                 505                 510

Ile Val Gly Leu Gln Tyr Lys Lys Asn Tyr Glu Asp Glu Asp Ser Leu
        515                 520                 525

Lys Thr Leu Arg Tyr Gly Lys Ile Met Ile Met Thr Asp Gln Asp Gln
        530                 535                 540

Asp Gly Ser His Ile Lys Gly Leu Leu Ile Asn Phe Ile His His Asn
545                 550                 555                 560

Trp Pro Ser Leu Leu Arg His Arg Phe Leu Glu Glu Phe Ile Thr Pro
                565                 570                 575

Ile Val Lys Val Ser Lys Asn Lys Gln Glu Met Ala Phe Tyr Ser Leu
            580                 585                 590

Pro Glu Phe Glu Glu Trp Lys Ser Ser Thr Pro Asn His Lys Lys Trp
        595                 600                 605

Lys Val Lys Tyr Tyr Lys Gly Leu Gly Thr Ser Thr Ser Lys Glu Ala
        610                 615                 620

Lys Glu Tyr Phe Ala Asp Met Lys Arg His Arg Ile Gln Phe Lys Tyr
625                 630                 635                 640

Ser Gly Pro Glu Asp Asp Ala Ala Ile Ser Leu Ala Phe Ser Lys Lys
                645                 650                 655

Gln Ile Asp Asp Arg Lys Glu Trp Leu Thr Asn Phe Met Glu Asp Arg
            660                 665                 670

Arg Gln Arg Lys Leu Leu Gly Leu Pro Glu Asp Tyr Leu Tyr Gly Gln
        675                 680                 685

Thr Thr Thr Tyr Leu Thr Tyr Asn Asp Phe Ile Asn Lys Glu Leu Ile
        690                 695                 700

Leu Phe Ser Asn Ser Asp Asn Glu Arg Ser Ile Pro Ser Met Val Asp
705                 710                 715                 720

Gly Leu Lys Pro Gly Gln Arg Lys Val Leu Phe Thr Cys Phe Lys Arg
                725                 730                 735

Asn Asp Lys Arg Glu Val Lys Val Ala Gln Leu Ala Gly Ser Val Ala
            740                 745                 750

Glu Met Ser Ser Tyr His His Gly Glu Met Ser Leu Met Met Thr Ile
        755                 760                 765

Ile Asn Leu Ala Gln Asn Phe Val Gly Ser Asn Asn Leu Asn Leu Leu
        770                 775                 780

Gln Pro Ile Gly Gln Phe Gly Thr Arg Leu His Gly Gly Lys Asp Ser
785                 790                 795                 800

Ala Ser Pro Arg Tyr Ile Phe Thr Met Leu Ser Ser Leu Ala Arg Leu
                805                 810                 815

Leu Phe Pro Pro Lys Asp Asp His Thr Leu Lys Phe Leu Tyr Asp Asp
            820                 825                 830

Asn Gln Arg Val Glu Pro Glu Trp Tyr Ile Pro Ile Ile Pro Met Val
        835                 840                 845
```

-continued

```
Leu Ile Asn Gly Ala Glu Gly Ile Gly Thr Gly Trp Ser Cys Lys Ile
    850                 855                 860
Pro Asn Phe Asp Val Arg Glu Ile Val Asn Asn Ile Arg Arg Leu Met
865                 870                 875                 880
Asp Gly Glu Glu Pro Leu Pro Met Leu Pro Ser Tyr Lys Asn Phe Lys
                885                 890                 895
Gly Thr Ile Glu Glu Leu Ala Pro Asn Gln Tyr Val Ile Ser Gly Glu
                900                 905                 910
Val Ala Ile Leu Asn Ser Thr Thr Ile Glu Ile Ser Glu Leu Pro Val
            915                 920                 925
Arg Thr Trp Thr Gln Thr Tyr Lys Glu Gln Val Leu Glu Pro Met Leu
    930                 935                 940
Asn Gly Thr Glu Lys Thr Pro Pro Leu Ile Thr Asp Tyr Arg Glu Tyr
945                 950                 955                 960
His Thr Asp Thr Val Lys Phe Val Val Lys Met Thr Glu Lys
                965                 970                 975
Leu Ala Glu Ala Glu Arg Val Gly Leu His Lys Val Phe Lys Leu Gln
                980                 985                 990
Thr Ser Leu Thr Cys Asn Ser Met Val Leu Phe Asp His Val Gly Cys
            995                 1000                1005
Leu Lys Lys Tyr Asp Thr Val Leu Asp Ile Leu Arg Asp Phe Phe Glu
    1010                1015                1020
Leu Arg Leu Lys Tyr Tyr Gly Leu Arg Lys Glu Trp Leu Leu Gly Met
1025                1030                1035                1040
Leu Gly Ala Glu Ser Ala Lys Leu Asn Asn Gln Ala Arg Phe Ile Leu
                1045                1050                1055
Glu Lys Ile Asp Gly Lys Ile Ile Glu Asn Lys Pro Lys Lys Glu
    1060                1065                1070
Leu Ile Lys Val Leu Ile Gln Arg Gly Tyr Asp Ser Asp Pro Val Lys
    1075                1080                1085
Ala Trp Lys Glu Ala Gln Gln Lys Val Pro Asp Glu Glu Asn Glu
    1090                1095                1100
Glu Ser Asp Asn Glu Lys Glu Thr Glu Lys Ser Asp Ser Val Thr Asp
1105                1110                1115                1120
Ser Gly Pro Thr Phe Asn Tyr Leu Leu Asp Met Pro Leu Trp Tyr Leu
                1125                1130                1135
Thr Lys Glu Lys Lys Asp Glu Leu Cys Arg Leu Arg Asn Glu Lys Glu
                1140                1145                1150
Gln Glu Leu Asp Thr Leu Lys Arg Lys Ser Pro Ser Asp Leu Trp Lys
            1155                1160                1165
Glu Asp Leu Ala Thr Phe Ile Glu Glu Leu Glu Ala Val Glu Ala Lys
    1170                1175                1180
Glu Lys Gln Asp Glu Gln Val Gly Leu Pro Gly Lys Gly Lys Ala
1185                1190                1195                1200
Lys Gly Lys Lys Thr Gln Met Ala Glu Val Leu Pro Ser Pro Arg Gly
            1205                1210                1215
Gln Arg Val Ile Pro Arg Ile Thr Ile Glu Met Lys Ala Glu Ala Glu
                1220                1225                1230
Lys Lys Asn Lys Lys Ile Lys Asn Glu Asn Thr Glu Gly Ser Pro
            1235                1240                1245
Gln Glu Asp Gly Val Glu Leu Glu Gly Leu Lys Gln Arg Leu Glu Lys
    1250                1255                1260
Lys Gln Lys Arg Glu Pro Gly Thr Lys Thr Lys Lys Gln Thr Thr Leu
```

```
                 1265                1270                1275                1280
       Ala Phe Lys Pro Ile Lys Lys Gly Lys Lys Arg Asn Pro Trp Ser Asp
                     1285                1290                1295
       Ser Glu Ser Asp Arg Ser Ser Asp Ser Asn Phe Asp Val Pro Pro
                 1300                1305                1310
       Arg Glu Thr Glu Pro Arg Arg Ala Ala Thr Lys Thr Lys Phe Thr Met
                     1315                1320                1325
       Asp Leu Asp Ser Asp Glu Asp Phe Ser Asp Phe Asp Glu Lys Thr Asp
                 1330                1335                1340
       Asp Glu Asp Phe Val Pro Ser Asp Ala Ser Pro Pro Lys Thr Lys Thr
       1345                1350                1355                1360
       Ser Pro Lys Leu Ser Asn Lys Glu Leu Lys Pro Gln Lys Ser Val Val
                     1365                1370                1375
       Ser Asp Leu Glu Ala Asp Asp Val Lys Gly Ser Val Pro Leu Ser Ser
                 1380                1385                1390
       Ser Pro Pro Ala Thr His Phe Pro Asp Glu Thr Glu Ile Thr Asn Pro
                     1395                1400                1405
       Val Pro Lys Lys Asn Val Thr Val Lys Lys Thr Ala Ala Lys Ser Gln
                 1410                1415                1420
       Ser Ser Thr Ser Thr Thr Gly Ala Lys Lys Arg Ala Ala Pro Lys Gly
       1425                1430                1435                1440
       Thr Lys Arg Asp Pro Ala Leu Asn Ser Gly Val Ser Gln Lys Pro Asp
                     1445                1450                1455
       Pro Ala Lys Thr Lys Asn Arg Arg Lys Arg Lys Pro Ser Thr Ser Asp
                 1460                1465                1470
       Asp Ser Asp Ser Asn Phe Glu Lys Ile Val Ser Lys Ala Val Thr Ser
                     1475                1480                1485
       Lys Lys Ser Lys Gly Glu Ser Asp Asp Phe His Met Asp Phe Asp Ser
                 1490                1495                1500
       Ala Val Ala Pro Arg Ala Lys Ser Val Arg Ala Lys Lys Pro Ile Lys
       1505                1510                1515                1520
       Tyr Leu Glu Glu Ser Asp Glu Asp Asp Leu Phe
                     1525                1530

<210> SEQ ID NO 43
<211> LENGTH: 4797
<212> TYPE: DNA
<213> ORGANISM: Homo sapiens

<400> SEQUENCE: 43
gcagtgaaca caacctttcc cctgagccac tggaattgga cagaatgccc cattctcctc      60
tgatctccat tcctcatgtg tggtgtcacc cagaagagga ggaaagaatg catgatgaac     120
ttctacaagc agtatccaag gggccggtga tgttcaggga tgtttccata gacttctctc     180
aagaggaatg gaatgcctg  acgctgatc agatgaattt atacaaagaa gtgatgttgg     240
agaatttcag caacctggtt tcagtgggac tttccaattc taagccagct gtgatctcct     300
tattggaaca aggaaaagag ccctggatgg ttgatagaga gctgactaga ggcctgtgtt     360
cagatctgga atcaatgtgt gagaccaaaa tattatctct aaagaagaga catttcagtc     420
aagtaataat tacccgtgaa gacatgtcta cttttattca gcccacattt cttattccac     480
ctcaaaaaac tatgagtgaa gagaaaccat gggaatgtaa gatatgtgga aagacccttta    540 atcaaaactc acaatttatc caacatcaga gaattcattt tggtgaaaaa cactatgaat     600
ctaaggagta tgggaagtcc tttagtcgtg gctcactcgt tactcgacat cagaggattc     660
```

-continued

```
acactggtaa aaaaccctat gaatgtaagg aatgtggcaa ggcttttagt tgtagttcat    720 attttctca acatcagagg attcacactg gtgagaaacc ctatgaatgt aaggaatgtg    780
gaaaagcctt taagtattgc tcaaaccttg atgatcatca gagaattcac actggtgaga    840
aaccctatga atgtaaagta tgtggaaaag cctttactaa aagttcacaa cttttctac    900 atctgagaat tcatactggt gagaaacctt atgaatgtaa agaatgtggg aaagccttta    960
ctcaacactc aaggcttatt cagcatcaga gaatgcatac tggtgagaaa ccttatgaat   1020
gtaagcagtg tgggaaggcc tttaatagtg cctcaacact tactaaccat cacagaattc   1080
atgctggtga gaagctctat gaatgtgaag aatgtagaaa ggcctttatt cagagctcag   1140
aacttattca acatcagaga atccatacag atgaaaaacc atatgaatgt aatgaatgtg   1200
ggaaggcctt taataaaggc tcaaatctta ctcgacatca gagaattcac actggtgaga   1260
aaccctatga ctgtaaggaa tgtggaaagg cttttggtag tcgctctgac ctcattcgcc   1320
atgagggaat tcatactggt tgaatgacag taaagtaaga ccattttgtt aacctttata   1380 ataattttt taaacaggt aaggagaaca aattaggata catattatca aaggttctcc   1440
tatgtattcg ttttaaacg atacgataac aaagtaccaa gtaccaaaac cttggtggct   1500
taaaacaaga gaaatttatt ctctcatagt ttagagcctg gaaatctaaa ctcaagggtg   1560
ctgatcgttt tggttccttc tgaggactct gaggatctgt tctatgcctt tttcctaacc   1620
tctgttaaca gctggcagtc cttggcattc catggctttt acatacacca ttccaatctc   1680
tgcctccatc ttcacattgc attctcgctg tgtatctctg tgtatgtctt ttatttggac   1740
accagtcagg ttagattggg gctacctggt gacctcatct taacttgatt atatctgcca   1800
agaccctgtt tccaagtaag gtcacattta ccggtaccag gggttaggac ttcagcatat   1860 cttttaggg gatacagttc aacccataat accctgttag aatgattttg tctaatatat   1920
ttgtaatttc cttttataca taagttgtta gtcaaattta ttttatttta ttttattttg   1980
agacagagtc tcgctctgtt gcccaggctg gagtgcagtg gtgtgatctc agctcactgc   2040
aacctccagc tcctgagttc aagcgattct tgtgcctcag cctctcaagt agttgggatt   2100
acaggcatgc gccaccatgc ccggctaatt ttttttttt tttttttgta ttttagtag   2160 cgacggggtt tcaccatgtt ggccaggctg gtcttgaact cctgacttca agtgatctgc   2220
ccgcctcagc ctcccaaagt gctgggatta cagacgtgag ccaccgtgat ggccaaaaca   2280
gactttatac aacaaaaat taaaaggac aaagaaggtc atttataatg ataaaggata   2340
aattcaacaa gaagataaaa caatcctaaa tatgtatgca cccaacactg caacacccag   2400
atccataaca cagatactac tagacctaag aaaagagata gacagcaata caacaatagc   2460 agggacttc accactccat tgacagcact agacagatca ctgggacaga aatcaacaaa   2520
gaaactctgg acttaaattg gactctacac caaatggacc caacagacat ctgaagaaca   2580
ttctacccaa caaccacaga atatatactc ttctcttctg tgcatggaac attctcaaaa   2640
ataggtcata tactggacca caaagcaagt atcaataaat tttaaaaaaa caaaatcata   2700
tctaacatct tctctgacca tagtggaata aaactagata tcaataccaa gaggaactct   2760
caaaacagat acatggaatt taaacagctt gctcctgaat gattttgga tcaatgatga   2820 aactaaggtg gaaatttaaa attttttgaa ataaatgaaa atagagacaa acacatgaa   2880 aacatctgag atacagcaaa agcagtgcta agagaggatt ttatagcatt aaatgcctac   2940
accaaaaaga tagaaaaatc tcaaatgaat agcctaacgt cacatctcaa ggaactagga   3000
```

-continued

```
aaaaacaaaa caaactcaac ccaaagctgg cagaagaaaa gcaataacaa atatcagagc    3060
aggcaaaaat gagactgaga acaaaggaat gcaaagatc aataaaagaa aaagttggtt     3120
ctttgtaaag ataaaactga cagaccacta gctagattaa ccaagaaaaa aagaagattc    3180
aaataaatac aatcagaaat gataaggtga tattataact gataacacag acatataaaa   3240
tatcagcaga aactatatgc acatattaga aaacctagag gaagtggata aattcctaga    3300
aacacataac cttccaagat tgaaccaggg agaaatagga atcctcaaca gactactgag    3360
tattgaaatt gaatcagtaa tagaaaaaaa tcttgcaaaa acaaaaagcc caggaccaga    3420
cagattcaca gctgaattct actagacatg caaggaagaa ctagtaacag cactattgaa    3480
actattccaa aaattatagg agggaatcct ccctaactca ttctacaaag ccagtatcat    3540
cctgatactg aagccaggca aggataaaac acacaaaaaa actacaagcc aatatccctg    3600
atgaaaatag acacaaaaat cttcagcaaa atactagcaa accaaatcaa acagtacata    3660
aaaaagatag taacagcaca gtcaagtgga tttattcct ggggtgtaag gatggctcaa     3720
catatgcaac tcaatacatg attcatcaca tacacagaat taaaaataag ccaggcactc    3780
acacctgtaa tcccagcact ttgcaaggcc aaggcgggca gatcacatga tgtcaagagt    3840
ttgagaccag tctggctgac atggcgaaac cctgtctcta ctaaaaatag aaaaattggc    3900
tgggcatggt ggcaggcact gtagtcccag ctacttggga ggctgaggca ggagaattac    3960
ttgaacctga gaagcggagg ttgcagtgag ctgagatagt gccattgcac tccagcctgg    4020
gcaacagagc aaattgcttg aatgtgggag gtggaggttg cagtgagccg agattatgcc    4080
attgcactcc agccggggga gcaacaaagc cagactccat ctcaaaaaaa aaccaaaaaa    4140
aatcctattt agtacaaggt acattattta ggtaatgagt ccattaaaag ccaacacttt    4200
ccccactaca ctatatgtgt atgtaacaca actgcccttg taacttccta aacctataat    4260
taagaaacaa taaaggcaa attaagaatg cttttttaaa aggtgggggc attatgctaa     4320
taagttactg tggatttcag agtgcagagt agaaagatca caagaattta gtgtggtagg    4380
tgggaacaga aaatgggtgt ataaatttta ttgacgtggg agtactggat attgtagaga    4440
cagatatcat cagggcaagg agattaaaga ttttttgcatt gacggtttga cactatattg    4500
tggtaataac actgtatgtg ttgggagata gaacaggaaa catcttccct ggaatatgta    4560
tactattaaa tgttttatca aacttttgat caaacaagac agcacaattt ataatttcat    4620
ttctattttct atgttatgag aaactgatca tttattcaaa tgtttaacag gcatgttcat    4680
gttactataa actcttctgt ttctccatca cgttgttggt catctttact gattacaaat    4740
ttctttacat atttaagaaa tatatatatt tctttatata ttaaaaaaaa aaaaaaa      4797
```

<210> SEQ ID NO 44
<211> LENGTH: 432
<212> TYPE: PRT
<213> ORGANISM: Homo sapiens

<400> SEQUENCE: 44

```
Met Pro His Ser Pro Leu Ile Ser Ile Pro His Val Trp Cys His Pro
 1               5                  10                  15

Glu Glu Glu Glu Arg Met His Asp Glu Leu Leu Gln Ala Val Ser Lys
            20                  25                  30

Gly Pro Val Met Phe Arg Asp Val Ser Ile Asp Phe Ser Gln Glu Glu
        35                  40                  45

Trp Glu Cys Leu Asp Ala Asp Gln Met Asn Leu Tyr Lys Glu Val Met
    50                  55                  60
```

-continued

```
Leu Glu Asn Phe Ser Asn Leu Val Ser Val Gly Leu Ser Asn Ser Lys
 65                  70                  75                  80

Pro Ala Val Ile Ser Leu Leu Glu Gln Gly Lys Glu Pro Trp Met Val
                 85                  90                  95

Asp Arg Glu Leu Thr Arg Gly Leu Cys Ser Asp Leu Glu Ser Met Cys
            100                 105                 110

Glu Thr Lys Ile Leu Ser Leu Lys Lys Arg His Phe Ser Gln Val Ile
        115                 120                 125

Ile Thr Arg Glu Asp Met Ser Thr Phe Ile Gln Pro Thr Phe Leu Ile
    130                 135                 140

Pro Pro Gln Lys Thr Met Ser Glu Glu Lys Pro Trp Glu Cys Lys Ile
145                 150                 155                 160

Cys Gly Lys Thr Phe Asn Gln Asn Ser Gln Phe Ile Gln His Gln Arg
                165                 170                 175

Ile His Phe Gly Glu Lys His Tyr Glu Ser Lys Glu Tyr Gly Lys Ser
            180                 185                 190

Phe Ser Arg Gly Ser Leu Val Thr Arg His Gln Arg Ile His Thr Gly
        195                 200                 205

Lys Lys Pro Tyr Glu Cys Lys Glu Cys Gly Lys Ala Phe Ser Cys Ser
    210                 215                 220

Ser Tyr Phe Ser Gln His Gln Arg Ile His Thr Gly Glu Lys Pro Tyr
225                 230                 235                 240

Glu Cys Lys Glu Cys Gly Lys Ala Phe Lys Tyr Cys Ser Asn Leu Asn
                245                 250                 255

Asp His Gln Arg Ile His Thr Gly Glu Lys Pro Tyr Glu Cys Lys Val
            260                 265                 270

Cys Gly Lys Ala Phe Thr Lys Ser Gln Leu Phe Leu His Leu Arg
        275                 280                 285

Ile His Thr Gly Glu Lys Pro Tyr Glu Cys Lys Glu Cys Gly Lys Ala
    290                 295                 300

Phe Thr Gln His Ser Arg Leu Ile Gln His Gln Arg Met His Thr Gly
305                 310                 315                 320

Glu Lys Pro Tyr Glu Cys Lys Gln Cys Gly Lys Ala Phe Asn Ser Ala
                325                 330                 335

Ser Thr Leu Thr Asn His His Arg Ile His Ala Gly Glu Lys Leu Tyr
            340                 345                 350

Glu Cys Glu Glu Cys Arg Lys Ala Phe Ile Gln Ser Ser Glu Leu Ile
        355                 360                 365

Gln His Gln Arg Ile His Thr Asp Glu Lys Pro Tyr Glu Cys Asn Glu
    370                 375                 380

Cys Gly Lys Ala Phe Asn Lys Gly Ser Asn Leu Thr Arg His Gln Arg
385                 390                 395                 400

Ile His Thr Gly Glu Lys Pro Tyr Asp Cys Lys Glu Cys Gly Lys Ala
                405                 410                 415

Phe Gly Ser Arg Ser Asp Leu Ile Arg His Glu Gly Ile His Thr Gly
            420                 425                 430
```

COMPOSITIONS, KITS, AND METHODS FOR IDENTIFICATION, ASSESSMENT, PREVENTION, AND THERAPY OF CERVICAL CANCER

RELATED APPLICATION

The present application claims priority from U.S. provisional patent application Ser. No. 60/404,770, filed on Aug. 20, 2002, which is expressly incorporated by reference.

FIELD OF THE INVENTION

The field of the invention is cervical cancer, including diagnosis, characterization, management, and therapy of cervical cancer.

BACKGROUND OF THE INVENTION

The increased number of cancer cases reported in the United States, and, indeed, around the world, is a major concern. Currently there are only a handful of treatments available for specific types of cancer, and these provide no absolute guarantee of success. In order to be most effective, these treatments require not only an early detection of the malignancy, but a reliable assessment of the severity of the malignancy.

Cancer of the cervix is one of the most common malignancies in women and remains a significant public health problem throughout the world. In the United States alone, invasive cervical cancer accounts for approximately 19% of all gynecological cancers. In 1996, it was estimated that there were 14,700 newly diagnosed cases and 4900 deaths attributed to this disease (American Cancer Society, Cancer Facts & Figures 1996, Atlanta, Ga.: American Cancer Society, 1996). In many developing countries, where mass screening programs are not widely available, the clinical problem is more serious. Worldwide, the number of new cases is estimated to be 471,000 with a four-year survival rate of only 40% (Munoz et al., 1989, *Epidemiology of Cervical Cancer* In: "Human Papillomavirus", New York, Oxford Press, pp 9-39; National Institutes of Health, Consensus Development Conference Statement on Cervical Cancer, Apr. 1-3, 1996).

In light of this, cervical cancer remains a highly preventable form of cancer when pre-invasive lesions are detected early. Cytological examination of Papanicolaou-stained cervical smears (also referred to as Pap smears or Pap tests) is currently the principle method for detecting cervical cancer and is the most cost-effective cancer screening test developed to date (Greenberg, M. D., et al., 1995, *Clin Obstet Gynecol* 38(3): 600-609). It has dramatically decreased the incidence and mortality rates of cervical cancer by more than 70% since it was introduced in the United States and many other countries of the world (Eddy D. M., 1990, *Ann. Intern. Med.* 113(3): 214-226). The abnormal morphologic changes of Pap tests described by The Bethesda System include ASCUS (atypical squamous cells of undetermined significance), AGUS (atypical glandular cells of undetermined significance), LSIL (low-grade squamous intraepithelial lesion), HSIL (high-grade squamous intraepithelial lesion), and squamous and adenocarcinoma (National Cancer Institute Workshop: The 1988 Bethesda System for reporting cervical/vaginal cytologic diagnosis. *JAMA*, 262 (7): 931-934). The success of Pap tests is attributed mostly to the diagnosis and treatment of precancerous lesions.

Currently, management of patients with HSIL and more advanced diseases is relatively standard. Most women with such lesions undergo colposcopy and appropriately directed biopsies. If the histologic diagnosis is confirmed, ablative or excisional treatment such as electrosurgical loop excision procedure (LEEP), cryosurgery or conization is performed. However, management of ambiguous or low-grade cytological results (ASCUS and LSIL) is very controversial. This is mainly due to the nature of this morphology-based test, which inevitably leads to interobserver variability and some Pap test discordance with histological follow-up. It was reported that the mean sensitivity of primary Pap tests is approximately 58% and the accuracy of a repeat test is only about 66% (Fahey M. T., et al., 1995, *Am. J. Epidemiol.* 141: 680-689). The low sensitivity and poor reproducibility have complicated the management of ASCUS and LSIL patients. If an "accelerated repeat Pap test" is recommended for the follow-up of women with primary diagnosis of ASCUS or LSIL, patients will risk delay in diagnosis of potential high-grade lesions. However, if these patients are universally referred to colposcopy, the vast majority of women will be over treated. Only 5-10% of women with ASCUS have high-grade disease upon colposcopy, and more than 80% of LSIL will regress to normal or stay in their current state (Cox, J. T., 2000, *Clinics in Laboratory Medicine.* 20(2): 303-343, Ostor A. G., 1993, *Int. J. Gynecol. Pathol.* 12(2): 186-192).

AGUS represents a much greater risk than ASCUS or LSIL because cytology is less sensitive for this condition and the disease progresses more rapidly (Anderson M. C., 1995, *Baillieres Clin. Obstet. Gynecol.* 9:105). It was found that 9-54% of women with AGUS have biopsy-confirmed cervical intraepithelial neoplasias, 0-8% have biopsy-confirmed adenocarcinoma in situ (AIS), and less than 1-9% have invasive carcinoma (Wright, T. C., et al., 2002, *JAMA*, 287(16): 2120-2129). Due to the greater risk, all patients with AGUS are referred to colposcopy (Wright, T. C., et al., 2002).

The subjectivity of cervical cytology could be reduced by objective markers that determine the presence and severity of dysplastic cells. Since high-risk human papillomavirus (HPV) infection is strongly associated with cervical cancer development (Walboomers, J. M., et al., 1999, *J. Pathol.* 189: 12-19), HPV testing using methods like Hybrid Capture II (Digene Diagnostics, Silver Spring, Md.) or PCR appears to provide an objective measurement (Wick, M. J., 2000, *Clinics in Laboratory Medicine*, 20(2): 271-287). However, since the vast majority of HPV infections and the resulting squamous intraepithelial lesions regress spontaneously, especially in young women, HPV testing cannot specifically identify patients whose lesions will persist or progress to invasive carcinoma (Sasieni, P. D., 2000, *J. Am. Med. Womens Assoc.* 55(4): 216-219, Sasieni, P. D., 2000, *Br. J. Cancer*, 83(5): 561-565). As reported in the ASCUS-LSEL Triage Study (ALTS), 83% of woman with LSIL Pap results test positive for high-risk HPV types, a level too high to be useful for triage (Human papillomavirus testing for triage of women with cytologic evidence of low-grade squamous intraepithelial lesions: baseline data from a randomized trial. The Atypical Squamous Cells of Undetermined Significance/Low-Grade Squamous Intraepithelial Lesions Triage Study (ALTS) Group, 2000, *J. Natl. Cancer Ist.* 92:397-402). Although triage using HPV testing significantly improved the sensitivity for detecting HSIL in women with ASCUS Pap results, the specificity was comparable to using conventional cytology (Solomon, D., et al., 2001, *J. Natl. Cancer Inst.* 93(4): 293-299). A more desirable cervical screening marker would identify all cervical cancers, the majority of HSIL, and the small percentage of true precancers amongst patients with LSIL and ASCUS on Pap.

It is now well accepted that cervical carcinogenesis occurs in a step-wise fashion (Ried, T., et al., 1999, *Genes Chromosomes Cancer*, 25(3): 195-204). The transition of normal epithelium to preneoplastic lesions and invasive carcinoma occurs sequentially. The morphologically defined steps of dysplastic and malignant abnormalities are a reflection of cellular gene alterations during tumorgenesis. It would thus be desirable to provide biomarkers useful for the identification, assessment, prevention and therapy of cervical cancer.

SUMMARY OF THE INVENTION

The invention relates to cancer markers (hereinafter "markers" or "markers of the inventions"), which are listed in Table 1. The invention provides nucleic acids and proteins that are encoded by or correspond to the markers (hereinafter "marker nucleic acids" and "marker proteins," respectively). Table 1 provides the sequence identifiers of the sequences of such marker nucleic acids and proteins listed in the accompanying Sequence Listing (SEQ ID NOs:1-44). Table 2 lists newly-identified nucleotide and amino acid sequences. Table 3 lists newly-identified nucleotide sequences. Tables 1-3 provide the sequence identifier numbers of the sequences of such marker nucleic acids and proteins listed in the accompanying Sequence Listing, and the gene names of the markers. The invention further provides antibodies, antibody derivatives and antibody fragments which bind specifically with such proteins and/or fragments of the proteins.

The invention also relates to various methods, reagents and kits for diagnosing, staging, prognosing, monitoring and treating cervical cancer. "Cervical cancer" as used herein includes carcinomas, (e.g., carcinoma in situ, invasive carcinoma, metastatic carcinoma) and pre-malignant conditions, (e.g., dysplasia, including CIN or SIL). In one embodiment, the invention provides a diagnostic method of assessing whether a patient has cervical cancer or has higher than normal risk for developing cervical cancer, comprising the steps of comparing the level of expression of a marker of the invention in a patient sample and the normal level of expression of the marker in a control, e.g., a sample from a patient without cervical cancer. A significantly higher level of expression of the marker in the patient sample as compared to the normal level is an indication that the patient is afflicted with cervical cancer or has higher than normal risk for developing cervical cancer.

According to the invention, the markers are selected such that the positive predictive value of the methods of the invention is at least about 10%, preferably about 25%, more preferably about 50% and most preferably about 90%. Also preferred for use in the methods of the invention are markers that are differentially expressed, as compared to normal cervical cells, by at least two-fold in at least about 20%, more preferably about 50% and most preferably about 75% of any of the following conditions: stage 0 cervical cancer patients, stage I cervical cancer patients, stage II cervical cancer patients, stage III cervical cancer patients, stage IV cervical cancer patients, grade I cervical cancer patients, grade II cervical cancer patients, grade III cervical cancer patients, squamous cell (epidermoid) cervical cancer patients, cervical adenocarcinoma patients, cervical adenosquamous carcinoma patients, small-cell cervical carcinoma patients, malignant cervical cancer patients, patients with primary carcinomas of the cervix, patients with primary malignant lymphomas of the cervix and patients with secondary malignant lymphomas of the cervix, and all other types of cancers, malignancies and transformations associated with the cervix.

In one embodiment, the present invention provides a diagnostic method of assessing whether a patient is afflicted with cervical cancer (e.g., new detection ("screening"), detection of recurrence, reflex testing), the method comprises comparing:
 a) the level of expression of a marker of the invention in a patient sample, and
 b) the normal level of expression of the marker in a control non-cervical cancer sample.

A significantly higher level of expression of the marker in the patient sample as compared to the normal level is an indication that the patient is afflicted with cervical cancer.

In another embodiment, the invention provides a diagnostic method of assessing whether a patient is afflicted with cervical cancer (e.g., new detection ("screening"), detection of recurrence, reflex testing), the method comprises comparing:
 a) the level of expression of a marker set of the invention in a patient sample, and
 b) the normal level of expression of the marker set in a control non-cervical cancer sample.

A significantly higher level of expression of the marker set in the patient sample as compared to the normal level is an indication that the patient is afflicted with cervical cancer.

The invention also provides diagnostic methods for assessing the efficacy of a therapy for inhibiting cervical cancer in a patient. Such methods comprise comparing:
 a) expression of a marker of the invention in a first sample obtained from the patient prior to providing at least a portion of the therapy to the patient, and
 b) expression of the marker in a second sample obtained from the patient following provision of the portion of the therapy.

A significantly lower level of expression of the marker in the second sample relative to that in the first sample is an indication that the therapy is efficacious for inhibiting cervical cancer in the patient.

It will be appreciated that in these methods the "therapy" may be any therapy for treating cervical cancer including, but not limited to, chemotherapy, radiation therapy, surgical removal of tumor tissue, gene therapy and biologic therapy such as the administering of antibodies and chemokines. Thus, the methods of the invention may be used to evaluate a patient before, during and after therapy, for example, to evaluate the reduction in tumor burden.

In a preferred embodiment, the diagnostic methods are directed to therapy using a chemical or biologic agent. These methods comprise comparing:
 a) expression of a marker of the invention in a first sample obtained from the patient and maintained in the presence of the chemical or biologic agent, and
 b) expression of the marker in a second sample obtained from the patient and maintained in the absence of the agent.

A significantly lower level of expression of the marker in the second sample relative to that in the first sample is an indication that the agent is efficacious for inhibiting cervical cancer, in the patient. In one embodiment, the first and second samples can be portions of a single sample obtained from the patient or portions of pooled samples obtained from the patient.

The invention additionally provides a monitoring method for assessing the progression of cervical cancer in a patient, the method comprising:
  a) detecting in a patient sample at a first time point, the expression of a marker of the invention;
  b) repeating step a) at a subsequent time point in time; and
  c) comparing the level of expression detected in steps a) and b), and therefrom monitoring the progression of cervical cancer in the patient.

A significantly higher level of expression of the marker in the sample at the subsequent time point from that of the sample at the first time point is an indication that the cervical cancer has progressed, whereas a significantly lower level of expression is an indication that the cervical cancer has regressed.

The invention further provides a diagnostic method for determining whether cervical cancer has metastasized or is likely to metastasize in the future, the method comprising comparing:
  a) the level of expression of a marker of the invention in a patient sample, and
  b) the normal level (or non-metastatic level) of expression of the marker in a control sample.

A significantly higher level of expression in the patient sample as compared to the normal level (or non-metastatic level) is an indication that the cervical cancer has metastasized or is likely to metastasize in the future.

The invention moreover provides a test method for selecting a composition for inhibiting cervical cancer in a patient. This method comprises the steps of:
  a) obtaining a sample comprising cancer cells from the patient;
  b) separately maintaining aliquots of the sample in the presence of a plurality of test compositions;
  c) comparing expression of a marker of the invention in each of the aliquots; and
  d) selecting one of the test compositions which significantly reduces the level of expression of the marker in the aliquot containing that test composition, relative to the levels of expression of the marker in the presence of the other test compositions.

The invention additionally provides a test method of assessing the cervical carcinogenic potential of a compound. This method comprises the steps of:
  a) maintaining separate aliquots of cervical cells in the presence and absence of the compound; and
  b) comparing expression of a marker of the invention in each of the aliquots.

A significantly higher level of expression of the marker in the aliquot maintained in the presence of the compound, relative to that of the aliquot maintained in the absence of the compound, is an indication that the compound possesses cervical carcinogenic potential.

In addition, the invention further provides a method of inhibiting cervical cancer in a patient. This method comprises the steps of:
  a) obtaining a sample comprising cancer cells from the patient;
  b) separately maintaining aliquots of the sample in the presence of a plurality of compositions;
  c) comparing expression of a marker of the invention in each of the aliquots; and
  d) administering to the patient at least one of the compositions which significantly lowers the level of expression of the marker in the aliquot containing that composition, relative to the levels of expression of the marker in the presence of the other compositions.

In the aforementioned methods, the samples or patient samples comprise cells obtained from the patient. The cells may be found in a cervical smear collected, for example, by a cervical brush. In another embodiment, the sample is a body fluid. Such fluids include, for example, blood fluids, lymph, ascitic fluids, gynecological fluids, urine, and fluids collected by vaginal rinsing. In a further embodiment, the patient sample is in vivo.

According to the invention, the level of expression of a marker of the invention in a sample can be assessed, for example, by detecting the presence in the sample of:
  the corresponding marker protein (e.g., a protein having one of the sequences set forth as "SEQ ID NO (AAs)" in Table 1, or a fragment of the protein (e.g. by using a reagent, such as an antibody, an antibody derivative, an antibody fragment or single-chain antibody, which binds specifically with the protein or protein fragment)
  the corresponding marker nucleic acid (e.g. a nucleotide transcript having one of the nucleic acid sequences set forth as "SEQ ID NO (nts)" in Table 1, or a complement thereof), or a fragment of the nucleic acid (e.g. by contacting transcribed polynucleotides obtained from the sample with a substrate having affixed thereto one or more nucleic acids having the entire or a segment of the nucleic acid sequence of any of the SEQ ID NO (nts), or a complement thereof)
  a metabolite which is produced directly (i.e., catalyzed) or indirectly by the corresponding marker protein.

According to the invention, any of the aforementioned methods may be performed using a plurality (e.g. 2, 3, 5, or 10 or more) of cervical cancer markers, including cervical cancer markers known in the art. In such methods, the level of expression in the sample of each of a plurality of markers, at least one of which is a marker of the invention, is compared with the normal level of expression of each of the plurality of markers in samples of the same type obtained from control humans not afflicted with cervical cancer. A significantly altered (i.e., increased or decreased as specified in the above-described methods using a single marker) level of expression in the sample of one or more markers of the invention, or some combination thereof, relative to that marker's corresponding normal or control level, is an indication that the patient is afflicted with cervical cancer. For all of the aforementioned methods, the marker(s) are preferably selected such that the positive predictive value of the method is at least about 10%.

In a further aspect, the invention provides an antibody, an antibody derivative, or an antibody fragment, which binds specifically with a marker protein (e.g., a protein having one of the amino acid sequences set forth in the Sequence Listing) or a fragment of the protein. The invention also provides methods for making such antibody, antibody derivative, and antibody fragment. Such methods may comprise immunizing a mammal with a protein or peptide comprising the entirety, or a segment of 10 or more amino acids, of a marker protein (e.g., a protein having one of the amino acid sequences set forth in the Sequence Listing), wherein the protein or peptide may be obtained from a cell or by chemical synthesis. The methods of the invention also encompass producing monoclonal and single-chain antibodies, which would further comprise isolating splenocytes from the immunized mammal, fusing the isolated splenocytes with an immortalized cell line to form hybridomas, and screening individual hybridomas for those that produce an antibody that binds specifically with a marker protein or a fragment of the protein.

In another aspect, the invention relates to various diagnostic and test kits. In one embodiment, the invention provides a kit for assessing whether a patient is afflicted with cervical cancer. The kit comprises a reagent for assessing expression of a marker of the invention. In another embodiment, the invention provides a kit for assessing the suitability of a chemical or biologic agent for inhibiting cervical cancer in a patient. Such a kit comprises a reagent for assessing expression of a marker of the invention, and may also comprise one or more of such agents. In a further embodiment, the invention provides kits for assessing the presence of cervical cancer cells or treating cervical cancers. Such kits comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

In an additional embodiment, the invention also provides a kit for assessing the presence of cervical cancer cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

In a further aspect, the invention relates to methods for treating a patient afflicted with cervical cancer or at risk of developing cervical cancer. Such methods may comprise reducing the expression and/or interfering with the biological function of a marker of the invention. In one embodiment, the method comprises providing to the patient an antisense oligonucleotide or polynucleotide complementary to a marker nucleic acid, or a segment thereof. For example, an antisense polynucleotide may be provided to the patient through the delivery of a vector that expresses an anti-sense polynucleotide of a marker nucleic acid or a fragment thereof. In another embodiment, the method comprises providing to the patient an antibody, an antibody derivative, or antibody fragment, which binds specifically with a marker protein or a fragment of the protein. In a preferred embodiment, the antibody, antibody derivative or antibody fragment binds specifically with a protein having one of the amino acid sequences set forth in the Sequence Listing, or a fragment of the protein.

It will be appreciated that the methods and kits of the present invention may also include known cancer markers including known cervical cancer markers. It will further be appreciated that the methods and kits may be used to identify cancers other than cervical cancer.

DETAILED DESCRIPTION OF THE INVENTION

Figure 1:
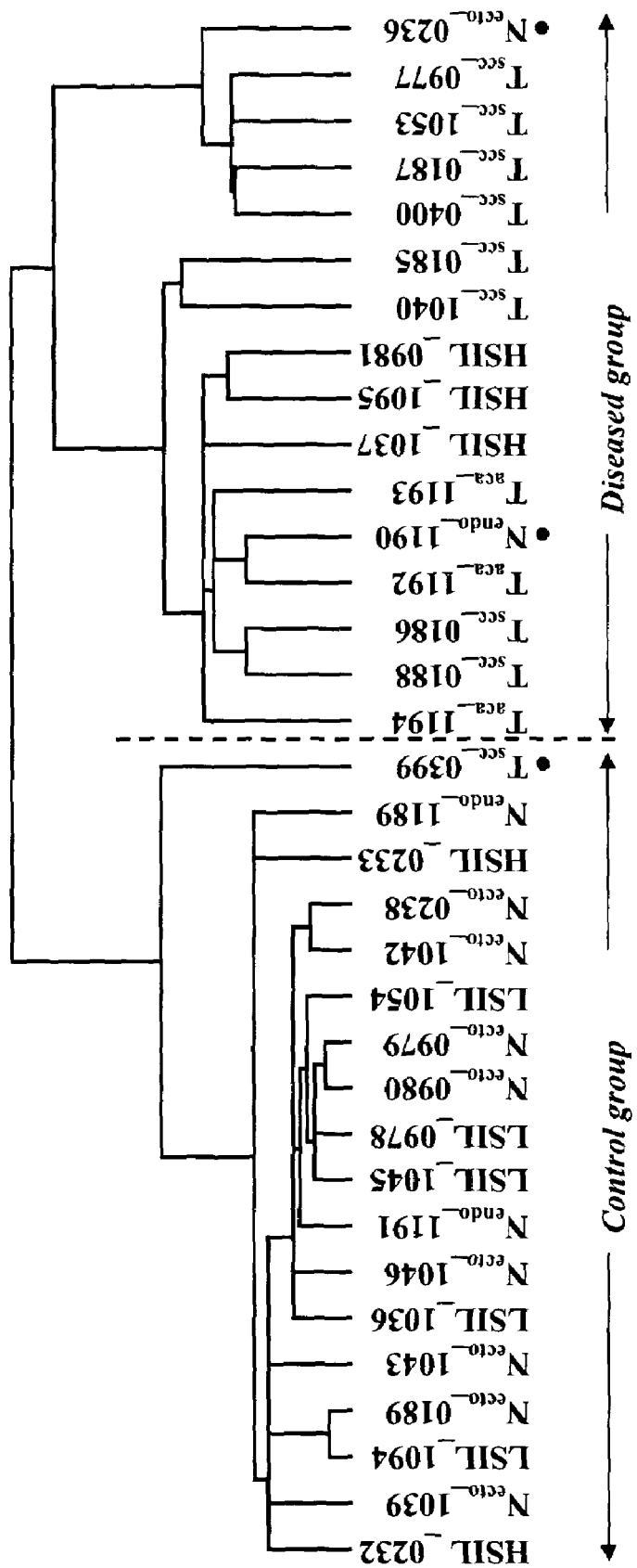
FIG. 1 depicts a cluster diagram of cervical tissue samples. Dendrogram was created from hierarchical clustering of the transcriptional profiles of 34 normal, LSEL, HSIL and cancerous cervical tissue samples. Each sample was labeled by its tissue type and an Id number. The abbreviations in FIG. 1 are defined as follows: $N_{ecto}$: normal ectocervix; $N_{endo}$: normal endocervix; LSIL: low-grade squamous intraepithelial lesion; HSIL: high-grade squamous intraepithelial lesion; $T_{scc}$: squamous cell carcinoma; $T_{aca}$: adenocarcinoma. The dashed line divides the 34 samples into two major groups: control group and diseased group. Filled circles indicate incorrectly clustered samples.

The invention relates to newly discovered cancer markers set forth in Table 1, associated with the cancerous state of cervical cells. It has been discovered that the higher than normal level of expression of any of these markers or combination of these markers correlates with the presence of cervical cancer including pre-malignant conditions such as dysplasia, in a patient. Methods are provided for detecting the presence of cervical cancer in a sample, the absence of cervical cancer in a sample, the stage of a cervical cancer, and other characteristics of cervical cancer that are relevant to prevention, diagnosis, characterization, and therapy of cervical cancer in a patient. Methods of treating cervical cancer are also provided.

Table 1 lists the markers of the invention, which are over-expressed in cervical cancer cells compared to normal (i.e., non-cancerous) cervical cells and comprises markers listed in Tables 2-13. Table 1 provides the sequence listing identifiers of the cDNA sequence of a nucleotide transcript and the amino acid sequence of a protein encoded by or corresponding to each marker, as well as the location of the protein coding sequence within the cDNA sequence. Table 2 lists newly-identified nucleotide and amino acid sequences. Table 3 lists newly-identified nucleotide sequences. Table 4 identifies markers of the present invention which were selected by transcription profiling experiments and their marker scores in SCC, ACA and HSIL. Table 5 identifies markers of the present invention that are overexpressed in cervical cancer by in situ hybridization and indicates the location of marker expression. Table 6 identifies markers of the present invention and the frequency of their expression using a cervical tissue microarray. Table 7 identifies gene specific primers. Table 8 sets forth the scoring on a scale of 0-5 of ethidium bromide agarose gel pictures of the endpoint PCR on the tissue panel. Tables 9-13 set forth expression of the target gene in each of the tissues tested.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the invention. A marker protein comprises the entire or a partial sequence of any of the sequences set forth in the Sequence Listing. The terms "protein" and "polypeptide" are used interchangeably.

A "marker set" is a group of more than one marker.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

A "cervical-associated" body fluid is a fluid which, when in the body of a patient, contacts or passes through cervical cells or into which cells or proteins shed from cervical cells are capable of passing. The cells may be found in a cervical smear collected, for example, by a cervical brush. Exemplary cervical-associated body fluids include blood fluids, lymph, ascitic fluids, gynecological fluids, cystic fluid, urine, and fluids collected by vaginal rinsing.

The "normal" level of expression of a marker is the level of expression of the marker in cervical cells of a human subject or patient not afflicted with cervical cancer.

An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples.

A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, a "naturally-occurring" nucleic acid molecule refers to an RNA or DNA molecule having a nucleotide sequence that occurs in an organism found in nature.

A cancer is "inhibited" if at least one symptom of the cancer is alleviated, terminated, slowed, or prevented. As used herein, cervical cancer is also "inhibited" if recurrence or metastasis of the cancer is reduced, slowed, delayed, or prevented.

A kit is any manufacture (e.g. a package or container) comprising at least one reagent, e.g. a probe, for specifically detecting the expression of a marker of the invention. The kit may be promoted, distributed, or sold as a unit for performing the methods of the present invention.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

Description

The present invention is based, in part, on newly identified markers which are over-expressed in cervical cancer cells as compared to their expression in normal (i.e. non-cancerous) cervical cells. The enhanced expression of one or more of these markers in cervical cells is herein correlated with the cancerous state of the tissue. The invention provides compositions, kits, and methods for assessing the cancerous state of cervical cells (e.g. cells obtained from a human, cultured human cells, archived or preserved human cells and in vivo cells) as well as treating patients afflicted with cervical cancer.

The compositions, kits, and methods of the invention have the following uses, among others:

1) assessing whether a patient is afflicted with cervical cancer;
2) assessing the stage of cervical cancer in a human patient;
3) assessing the grade of cervical cancer in a patient;
4) assessing the benign or malignant nature of cervical cancer in a patient;
5) assessing the metastatic potential of cervical cancer in a patient;
6) assessing the histological type of neoplasm associated with cervical cancer in a patient;
7) making antibodies, antibody fragments or antibody derivatives that are useful for treating cervical cancer and/or assessing whether a patient is afflicted with cervical cancer;
8) assessing the presence of cervical cancer cells;
9) assessing the efficacy of one or more test compounds for inhibiting cervical cancer in a patient;
10) assessing the efficacy of a therapy for inhibiting cervical cancer in a patient;
11) monitoring the progression of cervical cancer in a patient;
12) selecting a composition or therapy for inhibiting cervical cancer in a patient;
13) treating a patient afflicted with cervical cancer;
14) inhibiting cervical cancer in a patient;
15) assessing the cervical carcinogenic potential of a test compound; and
16) preventing the onset of cervical cancer in a patient at risk for developing cervical cancer.

The invention thus includes a method of assessing whether a patient is afflicted with cervical cancer which includes assessing whether the patient has pre-metastasized cervical cancer. This method comprises comparing the level of expression of a marker of the invention (listed in Table 1) in a patient sample and the normal level of expression of the marker in a control, e.g., a non-cervical cancer sample. A significantly higher level of expression of the marker in the patient sample as compared to the normal level is an indication that the patient is afflicted with cervical cancer.

Gene delivery vehicles, host cells and compositions (all described herein) containing nucleic acids comprising the entirety, or a segment of 15 or more nucleotides, of any of the nucleic acid sequences set forth in the Sequence Listing, or the complement of such sequences, and polypeptides comprising the entirety, or a segment of 10 or more amino acids, of any of the amino acid sequences set forth in the Sequence Listing, are also provided by this invention.

As described herein, cervical cancer in patients is associated with an increased level of expression of one or more markers of the invention. While, as discussed above, some of these changes in expression level result from occurrence of the cervical cancer, others of these changes induce, maintain, and promote the cancerous state of cervical cancer cells. Thus, cervical cancer characterized by an increase in the level of expression of one or more markers of the invention can be inhibited by reducing and/or interfering with the expression of the markers and/or function of the proteins encoded by those markers.

Expression of a marker of the invention can be inhibited in a number of ways generally known in the art. For example, an antisense oligonucleotide can be provided to the cervical cancer cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the cervical cancer cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the patient in order to inhibit cervical cancer cells of the patient.

Any marker or combination of markers of the invention, as well as any known markers in combination with the markers of the invention, may be used in the compositions, kits, and methods of the present invention. In general, it is preferable to use markers for which the difference between the level of expression of the marker in cervical cancer cells and the level of expression of the same marker in normal cervical cells is as great as possible. Although this difference can be as small as the limit of detection of the method for assessing expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the level of expression of the same marker in normal cervical tissue.

It is recognized that certain marker proteins are secreted from cervical cells (i.e. one or both of normal and cancerous cells) to the extracellular space surrounding the cells. These markers are preferably used in certain embodiments of the compositions, kits, and methods of the invention, owing to the fact that the such marker proteins can be detected in a cervical-associated body fluid sample, which may be more easily collected from a human patient than a tissue biopsy sample. In addition, preferred in vivo techniques for detection of a marker protein include introducing into a subject a labeled antibody directed against the protein. For example, the antibody can be labeled with a radioactive marker whose presence and location in a subject can be detected by standard imaging techniques.

It is a simple matter for the skilled artisan to determine whether any particular marker protein is a secreted protein. In order to make this determination, the marker protein is expressed in, for example, a mammalian cell, preferably a human cervical cell line, extracellular fluid is collected, and the presence or absence of the protein in the extracellular fluid is assessed (e.g. using a labeled antibody which binds specifically with the protein).

The following is an example of a method which can be used to detect secretion of a protein. About $8\times10^5$ 293T cells are incubated at 37° C. in wells containing growth medium (Dulbecco's modified Eagle's medium {DMEM} supplemented with 10% fetal bovine serum) under a 5% (v/v) $CO_2$, 95% air atmosphere to about 60-70% confluence. The cells are then transfected using a standard transfection mixture comprising 2 micrograms of DNA comprising an expression vector encoding the protein and 10 microliters of LipofectAMINE™ (GIBCO/BRL Catalog no. 18342-012) per well. The transfection mixture is maintained for about 5 hours, and then replaced with fresh growth medium and maintained in an air atmosphere. Each well is gently rinsed twice with DMEM which does not contain methionine or cysteine (DMEM-MC; ICN Catalog no. 16-424-54). About 1 milliliter of DMEM-MC and about 50 microcuries of Trans-$^{35}$S™ reagent (ICN Catalog no. 51006) are added to each well. The wells are maintained under the 5% $CO_2$ atmosphere described above and incubated at 37° C. for a selected period. Following incubation, 150 microliters of conditioned medium is removed and centrifuged to remove floating cells and debris. The presence of the protein in the supernatant is an indication that the protein is secreted.

It will be appreciated that patient samples containing cervical cells may be used in the methods of the present invention. In these embodiments, the level of expression of the marker can be assessed by assessing the amount (e.g. absolute amount or concentration) of the marker in a cervical cell sample, e.g., cervical smear obtained from a patient. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, cervical smears may also be subjected to post-collection preparative and storage techniques, e.g., fixation.

The compositions, kits, and methods of the invention can be used to detect expression of marker proteins having at least one portion which is displayed on the surface of cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the cell (e.g. using a labeled antibody which binds specifically with a cell-surface domain of the protein).

Expression of a marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In a preferred embodiment, expression of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker protein or fragment thereof, including a marker protein which has undergone all or a portion of its normal post-translational modification.

In another preferred embodiment, expression of a marker is assessed by preparing mRNA/cDNA (i.e. a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g. single nucleotide polymorphisms, deletions, etc.) of a marker of the invention may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a marker nucleic acid. If polynucleotides complementary to or homologous with are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

Because the compositions, kits, and methods of the invention rely on detection of a difference in expression levels of one or more markers of the invention, it is preferable that the level of expression of the marker is significantly greater than the minimum detection limit of the method used to assess expression in at least one of normal cervical cells and cancerous cervical cells.

It is understood that by routine screening of additional patient samples using one or more of the markers of the invention, it will be realized that certain of the markers are over-expressed in cancers of various types, including specific cervical cancers, as well as other cancers such as breast cancer, ovarian cancer, etc. For example, it will be confirmed that some of the markers of the invention are over-expressed in most (i.e. 50% or more) or substantially all (i.e. 80% or more) of cervical cancer. Furthermore, it will be confirmed that certain of the markers of the invention are associated with cervical cancer of various stages (i.e. stage 0, I, II, III, and IV cervical cancers, as well as subclassifications IA1, IA2, IB, IB1, IB2, IIA, IIB, IIIA, IIIB, IVA, and IVB, using the FIGO Stage Grouping system for primary carcinoma of the cervix (see Gynecologic Oncology, 1991, 41:199 and Cancer, 1992, 69:482)), and pre-malignant conditions (e.g., dysplasia including CIN or SIL), of various histologic subtypes (e.g. squamous cell carcinomas and squamous cell carcinoma variants such as verrucous carcinoma, lymphoepithelioma-like carcinoma, papillary squamous neoplasm and spindle cell squamous cell carcinoma (see Cervical Cancer and Preinvasive Neoplasia, 1996, pp. 90-91) serous, mucinous, endometrioid, and clear cell subtypes, as well as subclassifications and alternate classifications adenocarcinoma, papillary adenocarcinoma, papillary cystadenocarcinoma, surface papillary carcinoma, malignant adenofibroma, cystadenofibroma, adenocarcinoma, cystadenocarcinoma, adenoacanthoma, endometrioid stromal sarcoma, mesodermal {Müllerian} mixed tumor, malignant carcinoma, mixed epithelial tumor, and undifferentiated carcinoma, using the WHO/FIGO system for classification of malignant cervical tumors; Scully, *Atlas of Tumor Pathology*, 3d series, Washington D.C.), and various grades (i.e. grade I {well differentiated}, grade II {moderately well differentiated}, and grade III {poorly differentiated from surrounding normal tissue}). In addition, as a greater number of patient samples are assessed for expression of the markers of the invention and the outcomes of the individual patients from whom the samples were obtained are correlated, it will also be confirmed that altered expression of certain of the markers of the invention are strongly correlated with malignant cancers and that altered expression of other markers of the invention are strongly correlated with benign tumors. The compositions, kits, and methods of the invention are thus useful for characterizing one or more of the stage, grade, histological type, and benign/malignant nature of cervical cancer in patients.

When the compositions, kits, and methods of the invention are used for characterizing one or more of the stage, grade, histological type, and benign/malignant nature of cervical cancer in a patient, it is preferred that the marker or panel of markers of the invention is selected such that a positive result is obtained in at least about 20%, and preferably at least about 40%, 60%, or 80%, and more preferably in substantially all patients afflicted with a cervical cancer of the corresponding stage, grade, histological type, or benign/malignant nature. Preferably, the marker or panel of markers of the invention is selected such that a positive predictive value (PPV) of greater than about 10% is obtained for the general population (more preferably coupled with an assay specificity greater than 80%).

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with cervical cancer. When a plurality of markers is used, it is preferred that 2, 3, 4, 5, 8, 10, 12, 15, 20, 30, or 50 or more individual markers be used, wherein fewer markers are preferred.

In order to maximize the sensitivity of the compositions, kits, and methods of the invention (i.e. by interference attributable to cells of non-cervical origin in a patient sample), it is preferable that the marker of the invention used therein be a marker which has a restricted tissue distribution, e.g., normally not expressed in a non-cervical tissue.

Only a small number of markers are known to be associated with cervical cancer (e.g. bcl-2, 15A8 antigen, cdc6, Mcm5, and EGFR). These markers are not, of course, included among the markers of the invention, although they may be used together with one or more markers of the invention in a panel of markers, for example. It is well known that certain types of genes, such as oncogenes, tumor suppressor genes, growth factor-like genes, protease-like genes, and protein kinase-like genes are often involved with development of cancers of various types. Thus, among the markers of the invention, use of those which correspond to proteins which resemble known proteins encoded by known oncogenes and tumor suppressor genes, and those which correspond to proteins which resemble growth factors, proteases, and protein kinases are preferred.

It is recognized that the compositions, kits, and methods of the invention will be of particular utility to patients having an enhanced risk of developing cervical cancer and their medical advisors. Patients recognized as having an enhanced risk of developing cervical cancer include, for example, patients having a familial history of cervical cancer, patients identified as having a mutant oncogene (i.e. at least one allele), and patients of advancing age (i.e. women older than about 50 or 60 years).

The level of expression of a marker in normal (i.e. non-cancerous) human cervical tissue can be assessed in a variety of ways. In one embodiment, this normal level of expression is assessed by assessing the level of expression of the marker in a portion of cervical cells which appears to be non-cancerous and by comparing this normal level of expression with the level of expression in a portion of the cervical cells which is suspected of being cancerous. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-cancer-afflicted patient, from a patient sample obtained from a patient before the suspected onset of cervical cancer in the patient, from archived patient samples, and the like.

The invention includes compositions, kits, and methods for assessing the presence of cervical cancer cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of cervical cancer cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of a method of the invention, a sample of normal cervical cells, a sample of cervical cancer cells, and the like.

The invention also includes a method of making an isolated hybridoma which produces an antibody useful for assessing whether patient is afflicted with a cervical cancer. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro using known methods). A vertebrate, preferably a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the marker protein or a fragment thereof. The invention also includes hybridomas made by this method and antibodies made using such hybridomas.

The invention also includes a method of assessing the efficacy of a test compound for inhibiting cervical cancer cells. As described above, differences in the level of expression of the markers of the invention correlate with the cancerous state of cervical cells. Although it is recognized that changes in the levels of expression of certain of the markers of the invention likely result from the cancerous state of cervical cells, it is likewise recognized that changes in the levels of expression of other of the markers of the invention induce, maintain, and promote the cancerous state of those cells. Thus, compounds which inhibit a cervical cancer in a patient will cause the level of expression of one or more of the markers of the invention to change to a level nearer the normal level of expression for that marker (i.e. the level of expression for the marker in non-cancerous cervical cells).

This method thus comprises comparing expression of a marker in a first cervical cell sample and maintained in the presence of the test compound and expression of the marker in a second cervical cell sample and maintained in the absence of the test compound. A significantly reduced expression of a marker of the invention in the presence of the test compound is an indication that the test compound inhibits cervical cancer. The cervical cell samples may, for example, be aliquots of a single sample of normal cervical cells obtained from a patient, pooled samples of normal cervical cells obtained from a patient, cells of a normal cervical cell line, aliquots of a single sample of cervical cancer cells obtained from a patient, pooled samples of cervical cancer cells obtained from a patient, cells of a cervical cancer cell line, or the like. In one embodiment, the samples are cervical cancer cells obtained from a patient and a plurality of compounds known to be effective for inhibiting various cervical cancers are tested in order to identify the compound which is likely to best inhibit the cervical cancer in the patient.

This method may likewise be used to assess the efficacy of a therapy for inhibiting cervical cancer in a patient. In this method, the level of expression of one or more markers of the invention in a pair of samples (one subjected to the therapy, the other not subjected to the therapy) is assessed. As with the method of assessing the efficacy of test compounds, if the therapy induces a significantly lower level of expression of a marker of the invention then the therapy is efficacious for inhibiting cervical cancer. As above, if samples from a selected patient are used in this method, then alternative therapies can be assessed in vitro in order to select a therapy most likely to be efficacious for inhibiting cervical cancer in the patient.

As described above, the cancerous state of human cervical cells is correlated with changes in the levels of expression of the markers of the invention. The invention includes a method for assessing the human cervical cell carcinogenic potential of a test compound. This method comprises maintaining separate aliquots of human cervical cells in the presence and absence of the test compound. Expression of a marker of the invention in each of the aliquots is compared. A significantly higher level of expression of a marker of the invention in the aliquot maintained in the presence of the test compound (relative to the aliquot maintained in the absence of the test compound) is an indication that the test compound possesses human cervical cell carcinogenic potential. The relative carcinogenic potentials of various test compounds can be assessed by comparing the degree of enhancement or inhibition of the level of expression of the relevant markers, by comparing the number of markers for which the level of expression is enhanced or inhibited, or by comparing both.

Various aspects of the invention are described in further detail in the following subsections.

I. Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a marker protein (e.g., a protein having one of the aniino acid sequences set forth in the Sequence Listing), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6×sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker protein that contain changes in amino acid residues that are not essential for activity. Such variant marker proteins differ in amino acid sequence from the naturally-occurring marker proteins, yet retain biological activity. In one embodiment, such a variant marker protein has an amino acid sequence that is at least about 40% identical, 50%, 60%, 70%, 80%, 90%, 95%, or 98% identical to the amino acid sequence of a marker protein.

An isolated nucleic acid molecule encoding a variant marker protein can be created by introducing one or more nucleotide substitutions, additions or deletions into the nucleotide sequence of marker nucleic acids, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded marker cDNA molecule or complementary to a marker mRNA sequence. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a marker protein. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a cervical-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a marker protein can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a marker of the invention can be inhibited by targeting nucleotide sequences complementary to the regulatory region of the gene encoding the marker nucleic acid or protein (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660: 27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

II. Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences comprising the sequence of any of the sequences set forth in the Sequence Listing. Other useful proteins are substantially identical (e.g., at least about 40%, preferably 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins comprising a marker protein or a segment thereof. As used herein, a "chimeric protein" or "fusion protein" comprises all or part (preferably a biologically active part) of a marker protein operably linked to a heterologous polypeptide (i.e., a polypeptide other than the marker protein). Within the fusion protein, the term "operably linked" is intended to indicate that the marker protein or segment thereof and the heterologous polypeptide are fused in-frame to each other.

The heterologous polypeptide can be fused to the amino-terminus or the carboxyl-terminus of the marker protein or segment.

One useful fusion protein is a GST fusion protein in which a marker protein or segment is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a marker protein can be removed and replaced with a signal sequence from another protein. For example, the gp67 secretory sequence of the baculovirus envelope protein can be used as a heterologous signal sequence (Ausubel et al., ed., Current Protocols in Molecular Biology, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a marker protein is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a marker protein. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a marker protein in a subject, to purify ligands and in screening assays to identify molecules which inhibit the interaction of the marker protein with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to marker proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker protein or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a marker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, Tetrahedron 39:3; Itakura et al., 1984, Annu. Rev. Biochem. 53:323; Itakura et al., 1984, Science 198:1056; Ike et al., 1983 Nucleic Acid Res. 11:477).

In addition, libraries of segments of a marker protein can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized protein or peptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a protein of the invention. In such a manner, the resulting antibody compositions have reduced or no binding of human proteins other than a protein of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof.

Polyclonal antibodies can be prepared by immunizing a suitable subject with a protein of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

The invention also provides recombinant antibodies that specifically bind a protein of the invention. In preferred embodiments, the recombinant antibodies specifically binds a marker protein or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptide. They can be produced by techniques known in the art, for example using methods described in Ladner et. al U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448; Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

In a preferred embodiment, the substantially purified antibodies of the invention may specifically bind to a signal peptide, a secreted sequence, an extracellular domain, a transmembrane or a cytoplasmic domain or cytoplasmic membrane of a protein of the invention. In a particularly preferred embodiment, the substantially purified antibodies of the invention specifically bind to a secreted sequence or an extracellular domain of the amino acid sequences of a protein of the invention. In a more preferred embodiment, the substantially purified antibodies of the invention specifically bind to a secreted sequence or an extracellular domain of the amino acid sequences of a marker protein.

An antibody directed against a protein of the invention can be used to isolate the protein by standard techniques, such as affinity chromatography or immunoprecipitation. Moreover, such an antibody can be used to detect the marker protein or fragment thereof (e.g., in a cellular lysate or cell supernatant) in order to evaluate the level and pattern of expression of the marker. The antibodies can also be used diagnostically to monitor protein levels in tissues or body fluids (e.g. in a cervical-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention may also be used as therapeutic agents in treating cancers. In a preferred embodiment, completely human antibodies of the invention are used for therapeutic treatment of human cancer patients, particularly those having an cervical cancer. In another preferred embodiment, antibodies that bind specifically to a marker protein or fragment thereof are used for therapeutic treatment. Further, such therapeutic antibody may be an antibody derivative or immunotoxin comprising an antibody conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibodies of the invention can be used for modifying a given biological response, for the drug moiety is not to be construed as limited to classical chemical therapeutic agents. For example, the drug moiety may be a protein or polypeptide possessing a desired biological activity. Such proteins may include, for example, a toxin such as ribosome-inhibiting protein (see Better et al., U.S. Pat. No. 6,146,631, the disclosure of which is incorporated herein in its entirety), abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Accordingly, in one aspect, the invention provides substantially purified antibodies, antibody fragments and derivatives, all of which specifically bind to a protein of the invention and preferably, a marker protein. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a protein of the invention and preferably, a marker protein. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a protein of the invention and preferably, a marker protein. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention. In one embodiment, the pharmaceutical composition comprises an antibody of the invention and a pharmaceutically acceptable carrier.

III. Recombinant Expression Vectors and Host Cells

Another aspect of the invention pertains to vectors, preferably expression vectors, containing a nucleic acid encoding a marker protein (or a portion of such a protein). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol.185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a marker protein or a segment thereof in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol.185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker will survive, while the other cells die).

A host cell of the invention, such as a prokaryotic or eukaryotic host cell in culture, can be used to produce a marker protein or a segment thereof. Accordingly, the invention further provides methods for producing a marker protein or a segment thereof using the host cells of the invention. In one embodiment, the method comprises culturing the host cell of the invention (into which a recombinant expression vector encoding a marker protein or a segment thereof has been introduced) in a suitable medium such that the is produced. In another embodiment, the method further comprises isolating the marker protein or a segment thereof from the medium or the host cell.

The host cells of the invention can also be used to produce nonhuman transgenic animals. For example, in one embodiment, a host cell of the invention is a fertilized oocyte or an embryonic stem cell into which a sequences encoding a marker protein or a segment thereof have been introduced. Such host cells can then be used to create non-human transgenic animals in which exogenous sequences encoding a marker protein of the invention have been introduced into their genome or homologous recombinant animals in which endogenous gene(s) encoding a marker protein have been altered. Such animals are useful for studying the function and/or activity of the marker protein and for identifying and/or evaluating modulators of marker protein. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a marker protein into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a marker protein into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a marker nucleic acid or protein. Such methods comprise formulating a pharmaceutically acceptable carrier with an agent which modulates expression or activity of a marker nucleic acid or protein. Such compositions can further include additional active agents. Thus, the invention further includes methods for preparing a pharmaceutical composition by formulating a pharmaceutically acceptable carrier with an agent which modulates expression or activity of a marker nucleic acid or protein and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a protein encoded by or corresponding to a marker or biologically active portion thereof. In another embodiment, the invention provides assays for screening candidate or test compounds which bind to a protein encoded by or corresponding to a marker or biologically active portion thereof. Determining the ability of the test compound to directly bind to a protein can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}$I, $^{35}$S, $^{14}$C, or $^{3}$H, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the expression of a marker or the activity of a protein encoded by or corresponding to a marker, or a biologically active portion thereof. In all likelihood, the protein encoded by or corresponding to the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of a protein encoded by or corresponding to marker to identify the protein's natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al, 1993, *Cell* 72:223-232; Madura et al, 1993, *J. Biol. Chem.* 268:12046-12054; Bartel et al, 1993, *Biotechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker protein or downstream elements of a marker protein-mediated signaling pathway. Alternatively, such marker protein binding partners may also be found to be inhibitors of the marker protein.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker protein and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is an cervical cancer marker protein identified herein, the known binding partner and/or substrate of same, and the test compound. Test compounds can be supplied from any source.

The basic principle of the assay systems used to identify compounds that interfere with the interaction between the marker protein and its binding partner involves preparing a reaction mixture containing the marker protein and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker protein and its binding partner. Control reaction mixtures are incubated without the test compound or with a placebo. The formation of any complexes between the marker protein and its binding partner is then detected. The formation of a complex in the control reaction, but less or no such formation in the reaction mixture containing the test compound, indicates that the compound interferes with the interaction of the marker protein and its binding partner. Conversely, the formation of more complex in the presence of compound than in the control reaction indicates that the compound may enhance interaction of the marker protein and its binding partner.

The assay for compounds that interfere with the interaction of the marker protein with its binding partner may be conducted in a heterogeneous or homogeneous format. Heterogeneous assays involve anchoring either the marker protein or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the marker proteins and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker protein or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker protein or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker protein or a marker protein binding partner can be immobilized utilizing conjugation of biotin and streptavidin. Biotinylated marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August;18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11:141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker protein and its binding partner.

Also within the scope of the present invention are methods for direct detection of interactions between the marker protein and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of marker mRNA or protein in the cell, is determined. The level of expression of marker mRNA or protein in the presence of the candidate compound is compared to the level of expression of marker mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., a marker modulating agent, an antisense marker nucleic acid molecule, a marker-specific antibody, or a marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF;

Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the cervical epithelium). A method for lipidation of antibodies is described by Cruikshank et al. (1997) *J. Acquired Immune Deficiency Syndromes and Human Retrovirology* 14:193.

The invention also provides vaccine compositions for the prevention and/or treatment of cervical cancer. The invention provides cervical cancer vaccine compositions in which a protein of a marker of Table 1, or a combination of proteins of the markers of Table 1, are introduced into a subject in order to stimulate an immune response against the cervical cancer. The invention also provides cervical cancer vaccine compositions in which a gene expression construct, which expresses a marker or fragment of a marker identified in Table 1, is introduced into the subject such that a protein or fragment of a protein encoded by a marker of Table 1 is produced by transfected cells in the subject at a higher than normal level and elicits an immune response.

In one embodiment, a cervical cancer vaccine is provided and employed as an immunotherapeutic agent for the prevention of cervical cancer. In another embodiment, a cervical cancer vaccine is provided and employed as an immunotherapeutic agent for the treatment of cervical cancer.

By way of example, a cervical cancer vaccine comprised of the proteins of the markers of Table 1, may be employed for the prevention and/or treatment of cervical cancer in a subject by administering the vaccine by a variety of routes, e.g., intradermally, subcutaneously, or intramuscularly. In addition, the cervical cancer vaccine can be administered together with adjuvants and/or immunomodulators to boost the activity of the vaccine and the subject's response. In one embodiment, devices and/or compositions containing the vaccine, suitable for sustained or intermittent release could be, implanted in the body or topically applied thereto for the relatively slow release of such materials into the body. The cervical cancer vaccine can be introduced along with immunomodulatory compounds, which can alter the type of immune response produced in order to produce a response which will be more effective in eliminating the cancer.

In another embodiment, a cervical cancer vaccine comprised of an expression construct of the markers of Table 1, may be introduced by injection into muscle or by coating onto microprojectiles and using a device designed for the purpose to fire the projectiles at high speed into the skin. The cells of the subject will then express the protein(s) or fragments of proteins of the markers of Table 1 and induce an immune response. In addition, the cervical cancer vaccine may be introduced along with expression constructs for immunomodulatory molecules, such as cytokines, which may increase the immune response or modulate the type of immune response produced in order to produce a response which will be more effective in eliminating the cancer.

The marker nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing cervical cancer. Such assays can be used for prognostic or predictive purposes to thereby prophylactically treat an individual prior to the onset of the cancer.

Yet another aspect of the invention pertains to monitoring the influence of agents (e.g., drugs or other compounds administered either to inhibit cervical cancer or to treat or prevent any other disorder {i.e. in order to understand any cervical carcinogenic effects that such treatment may have}) on the expression or activity of a marker of the invention in clinical trials. These and other agents are described in further detail in the following sections.

A. Diagnostic Assays

An exemplary method for detecting the presence or absence of a marker protein or nucleic acid in a biological sample involves obtaining a biological sample (e.g. a cervical-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10;699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cervical cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cervical cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cervical cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from cervical cancer or from non-cervical cancer cells of cervical tissue. The choice of the cell source is dependent on the use of the relative expression level. Using expression found in normal tissues as a mean expression score aids in validating whether the marker assayed is cervical specific (versus normal cells). In addition, as more data is accumulated, the mean expression value can be revised, providing improved relative expression values based on accumulated data. Expression data from cervical cells provides a means for grading the severity of the cervical cancer state.

In another embodiment of the present invention, a marker protein is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from cervical cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether cervical cells express a marker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cervical cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a marker protein or nucleic acid in a biological sample (e.g., cervical smear). Such kits can be used to determine if a subject is suffering from or is at increased risk of developing cervical cancer. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

B. Pharmacogenomics

The markers of the invention are also useful as pharmacogenomic markers. As used herein, a "pharmacogenomic marker" is an objective biochemical marker whose expression level correlates with a specific clinical drug response or susceptibility in a patient (see, e.g., McLeod et al. (1999) *Eur. J. Cancer* 35(12): 1650-1652). The presence or quantity of the pharmacogenomic marker expression is related to the predicted response of the patient and more particularly the patient's tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected. For example, based on the presence or quantity of RNA or protein encoded by specific tumor markers in a patient, a drug or course of treatment may be selected that is optimized for the treatment of the specific tumor likely to be present in the patient. The use of pharmacogenomic markers therefore permits selecting or designing the most appropriate treatment for each cancer patient without trying different drugs or regimes.

Another aspect of pharmacogenomics deals with genetic conditions that alters the way the body acts on drugs. These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

C. Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for cervical cancer. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of the marker gene(s) during the course of treatment may indicate ineffective dosage and the desirability of increasing the dosage. Conversely, decreased expression of the marker gene(s) may indicate efficacious treatment and no need to change dosage.

D. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the marker nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has cervical cancer or a pre-disposition to cervical cancer, wherein the method comprises the steps of determining the presence or absence of a marker and based on the presence or absence of the marker, determining whether the subject has cervical cancer or a pre-disposition to cervical cancer and/or recommending a particular treatment for cervical cancer or pre-cervical cancer condition.

The present invention further provides in an electronic system and/or in a network, a method for determining whether a subject has cervical cancer or a pre-disposition to cervical cancer associated with a marker wherein the method comprises the steps of determining the presence or absence of the marker, and based on the presence or absence of the marker, determining whether the subject has cervical cancer or a pre-disposition to cervical cancer, and/or recommending a particular treatment for the cervical cancer or pre-cervical cancer condition. The method may further comprise the step of receiving phenotypic information associated with the subject and/or acquiring from a network phenotypic information associated with the subject.

The present invention also provides in a network, a method for determining whether a subject has cervical cancer or a pre-disposition to cervical cancer associated with a marker, said method comprising the steps of receiving information associated with the marker receiving phenotypic information associated with the subject, acquiring information from the network corresponding to the marker and/or cervical cancer, and based on one or more of the phenotypic information, the marker, and the acquired information, determining whether the subject has a cervical cancer or a pre-disposition to cervical cancer. The method may further comprise the step of recommending a particular treatment for the cervical cancer or pre-cervical cancer condition.

The present invention also provides a business method for determining whether a subject has cervical cancer or a pre-disposition to cervical cancer, said method comprising the steps of receiving information associated with the marker, receiving phenotypic information associated with the subject, acquiring information from the network corresponding to the marker and/or cervical cancer, and based on one or more of the phenotypic information, the marker, and the acquired information, determining whether the subject has cervical cancer or a pre-disposition to cervical cancer. The method may further comprise the step of recommending a particular treatment for the cervical cancer or pre-cervical cancer condition.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of cervical cancer, progression of cervical cancer, and processes, such a cellular transformation associated with cervical cancer.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

E. Surrogate Markers

The markers of the invention may serve as surrogate markers for one or more disorders or disease states or for conditions leading up to disease states, and in particular, cervical cancer. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The markers of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

EXAMPLE 1

Identification of Cervical Cancer Markers by cDNA and Tissue Microarrays

I. Materials and Methods

Sample Collection and RNA Preparation

Cervical tissues were collected and snap frozen in liquid nitrogen. The histology and cellular composition of tissues were confirmed before RNA extraction was performed. Total RNA was extracted from the frozen tissues using Trizol® Reagent (Life Technologies) followed by a secondary clean up step with Qiagen's RNeasy kit to increase RNA probe labeling efficiency (Qiagen, Valencia Calif.). Only RNA with a 28S/18S ribosomal RNA ratio of at least 1.0, calculated using Agilent Technologies 2100 Bioanalyzer (Palo Alto, Calif.), was used in this study.

cDNA Microarray Hybridization cDNA microarrays containing 30,732 Unigene clones from Research Genetics (Hunstville, Ala.) were generated on nylon filters. A total of 4-6 ug of total RNA was used as template to generate radioactively labeled cDNA by reverse transcription with $^{33}$P-dCTP, oligo dT-30 primer and Superscript II Reverse Transcriptase (Life Technologies). $^{33}$P-labeled first strand cDNA was preannealed with cot-1 DNA and poly-dA 40-60 (Pharmacia, Peapack, N.J.) to reduce non-specific hybridization. Each filter was hybridized at 65° C. for 16 hours with approximately $6\times10^6$ counts of labeled probe in a buffer containing 7% sodium dodecyl sulfate (SDS), 250 mM $Na_3PO_4$ (pH 7.2), 1 mM EDTA, 0.5% Casein-Hammerstein and 0.1 mg/ml of denatured salmon sperm DNA. After the filters were washed with 4% and 1% SDS wash buffer (20 mM $Na_3PO_4$ (pH 7.2), 1 mM EDTA and 4% or 1% SDS), they were exposed to Fuji Phosphoimager screens and scanned using a Fuji scanner BAS 2500. Spots were quantitated using an automated array analysis program, Grid Guru v1.0, developed at Millennium Pharmaceuticals, Inc.

Marker Scoring Algorithm and Data Analysis

To correct for differences in hybridization efficiency, the digitized data from each microarray filter was normalized by the median intensity of all spots on that filter. Both array-based and gene-based hierarchical clustering was performed and visualized using Stanford's Gene Cluster and Tree View software. Differentially expressed genes were ranked by calculating the Marker Score for each gene.

To compute Marker Score, the samples were divided into control and tester groups. The starting point for the Marker Score is average fold change (ratio) of the tester samples above the control samples. The score was designed to reflect both the degree of change (the expression ratio) and the number of tester samples showing differential expression, while not being dominated by a small fraction of tester samples with very high values. To reduce this "outlier" effect, genes were treated with expression ratios greater than 10 as not meaningfully different from those with ratios of 10. This desired performance from a Marker Score was accomplished by transforming the tester:control expression ratio using an asymptotic compression function before taking the average fold-change across tester samples. A Marker Score has a value of 1 when the testers do not appear to be expressed more highly than the controls, and a value greater than 1 otherwise. A Marker Score cannot exceed a value of 10 for any gene.

The Marker Score $S_g$ for gene g is therefore computed as the average of compressed tester:control ratios:

$S_g = (\Sigma S_{gs})/N_{tester}$
$S_{gs} = C(x_{gs}/(k+x_g^Q))$, where $S_{gs}$ represents the Marker Score for gene g and the sample s, C(r) is the compression function $C(r)=A(1-e^{-r/A})$ for $r \geq 1$, and C(r)=1 for r<1, A is an upper asymptote on the fold-change value (we used 10), $x_{gs}$ is the expression value of gene g on sample s, $x_g^Q$ is the Qth percentile of the control samples' expression value; typically Q=50, k is a constant reflecting the additive noise in the data, i.e., the fixed component of the variance in repeated measurements. A value of 0.25 was derived for this parameter from calibration experiments using microarray technology.

$N_{tester}$ The number of tester samples

In situ Hybridization of Tissue Microarrays

Formalin-fixed, paraffin embedded cervical tissue microarrays containing tissue cores from normal, low-grade squamous intraepithelial lesions (LSIL), high-grade squamous intraepithelial lesions (HSIL), squamous cell carcinomas (SCC) and adenocarcinomas (ACA) were provided. Prehybridization treatment was performed with an automatic Tissue-Tek DRS 2000 Slide Stainer (Sakura, Torrance, Calif.) using a previously described protocol (Duncan, L. M., et al., 2001, *J. Clin. Oncol.* 19(2): 568-576). The cervical tissues were deparaffinized, rehydrated and postfixed with 4% paraformaldehyde in PBS for 15 minutes. After washing with PBS, the tissue microarrays were digested with 2 ug/ml proteinase K at 37° C. for 15 minutes and again incubated with 4% paraformaldehyde/PBS for 10 minutes. Tissue sections were subsequently incubated with 0.2N HCL for 10 minutes, 0.25% acetic anhydride/0.1 mol/L triethanolamine for 10 minutes, and dehydrated with graded ethanol. Antisense probes were labeled with $^{35}$S-UTP in an in vitro transcription reaction (Riboprobe Combination System, Promega, Madison, Wis.) using 500 ng of linearized plasmid DNA derived from IMAGE clones. Hybridizations were performed at 50° C. for 18 hours using probes labeled at $5\times10^7$ cpm/ml in 10 mM Tris-HCl (pH 7.6) buffer containing 50% formamide, 10% dextran sulfate, 1×Denhardt's solution, 0.6 M NaCl, 10 mM DTT, 0.25% SDS and 200 ug/ml tRNA. After hybridization, slides were washed with 5×standard saline citrate (SSC) at 50° C. for 10 minutes, 50% formamide/2×SSC at 50° C. for 30 minutes, 10 mM Tris-HCl (pH 7.6)/500 mM NaCl/1 mM EDTA (TNE) at 37° C. for 10 minutes, incubated in 10 ug/ml Rnase A in TNE at 37° C. for 30 minutes, washed in TNE at 37° C. for 10 minutes, incubated once in 2×SSC at 50° C. for 20 minutes, twice in 0.2×SSC at 50° C. for 20 minutes, and dehydrated with graded ethanol. Localization of mRNA transcripts was determined by dipping slides in Kodak NTB2 photoemulsion (Eastman Kodak, Rochester, N.Y.) and exposing for 14-21 days at 4° C. The slides were counterstained using Myers hematoxylin and alcoholic eosin Y.

II. Results

Transcriptional Profiling of Cervical Tissues by cDNA Microarrays 12 normal cervical tissues (9 from ectocervix and 3 from endocervix), 5 LSIL, 5 HSIL, 9 SCC and 3 ACA were profiled on cDNA microarrays that contain 30,732 clones (30K microarray). To assess the power of the data sets to discriminate between diseased and normal tissue, a hierarchical clustering of the 34 sample data sets was performed on the basis of overall similarity in gene expression patterns (FIG. 1). The dendrogram shows that 10 of 12 normal cervical tissues and all LSIL samples cluster in one group (designated as "control group"), and 11 of 12 tumor samples and 3 of 5 HSIL samples cluster together in the other group (designated as "diseased group"). This segregation indicates that global gene expression profiles of normal ectocervical epithelium, normal endocervical epithelium and LSIL are very similar, whereas the expression profiles of 3/5 HSIL samples more closely resemble cervical cancers. These findings indicate robust data sets that can distinguish control tissues from diseased tissues despite the fact that samples were taken from patients of different ages and from different clinical sites.

Marker Selection

Figure 2:
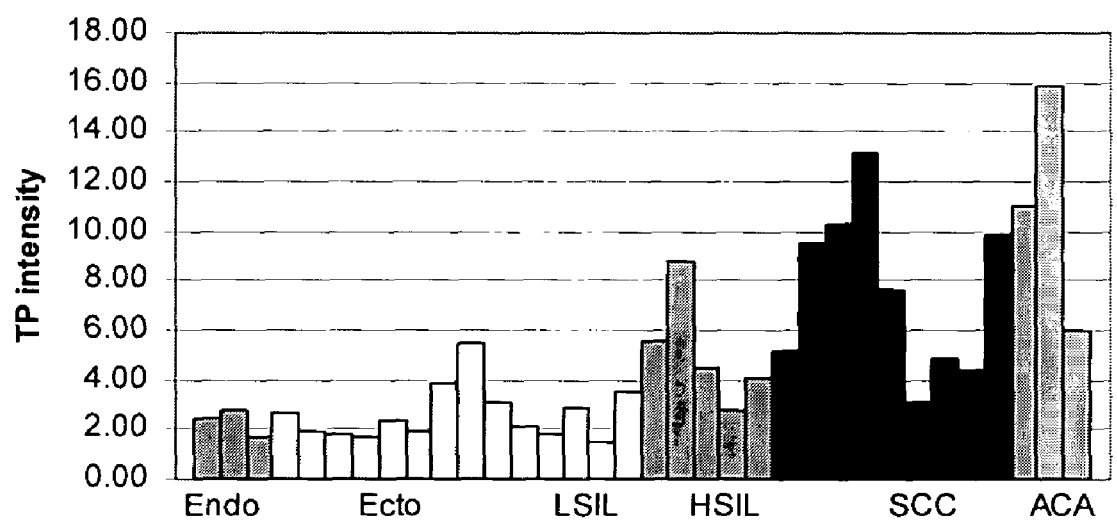
FIG. 2 depicts transcriptional profiles (TP) of MCM6 and Claudin 1 in normal, dysplastic and cancerous cervical tissues by cDNA microarray hybridization. Each data point represents the average of duplicate microarray hybridizations. The TP intensity was normalized by the median intensity of all spots on the array. The abbreviations in FIG. 2 are defined as follows: Endo: normal endocervical tissue; Ecto: normal ectocervical tissue; LSIL: low-grade squamous intraepithelial lesion; HSIL: high-grade squamous intraepithelial lesion; SCC: squamous cell carcinoma; ACA: adenocarcinoma.
Figure 2:
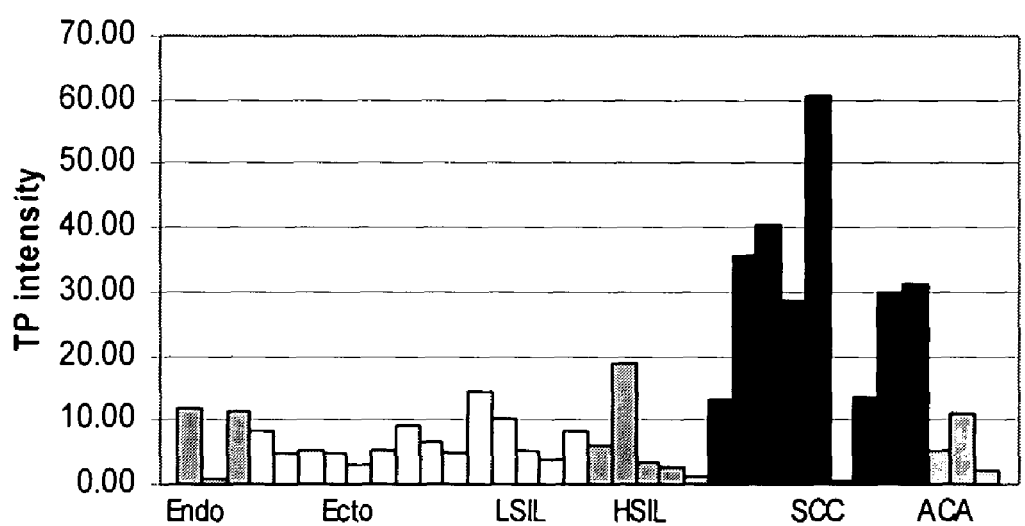

In order to identify gene markers that would differentiate the control tissue group from the diseased group, marker scores were calculated for each clone on the 30K cDNA microarray from three marker selection paradigms: 9 SCC vs. control group (9 ectocervix, 3 endocervix and 5 LSIL), 5 HSIL vs. control group, and 3 ACA vs. control group. In order to discover new markers associated with the transformation of cervical cells, up-regulated genes related to an immune response (i.e. immunoglobulins, MHCs) were excluded during marker selection. Clones with marker scores ranked in the top 50 from SCC or ACA paradigms, and clones ranked between 50 and 100 that were overexpressed in both SCC and ACA samples were selected as top markers. Scores from the HSIL paradigm were not used independently to select markers because increased expression in tumors was considered essential for good marker performance. Markers were selected and their scores in SCC, ACA and HSIL paradigms are shown in Table 4. It was found that most of the up-regulated genes from SCC samples were also elevated in ACA. While many markers selected from the SCC and/or ACA paradigms have scores $\geq 3.0$, only a few of the HSIL markers had scores above 2.0, indicating increasing expression as lesions progress from dysplasia to invasive carcinomas. FIG. 2 shows two genes from Table 4 that represent typical but distinct types of expression patterns among normal, LSIL, HSIL, SCC and ACA tissues. MCM 6 was overexpressed in HSILs, squamous cell carcinomas and adenocarcinomas, while Claudin 1 was overexpressed only in squamous cell carcinomas.

In an attempt to understand the characteristics of these up-regulated genes, hierarchical clustering was performed based on the expression profiles across all clinical samples. These overexpressed genes were clustered into two main groups. One group consists mainly of genes that encode either extracellular matrix (ECM) proteins (collagen, laminin, fibronectin) or proteins responsible for cell-ECM interaction or ECM degradation and remodeling (e.g. osteonectin, matrix metalloproteinase, urokinase). The other cluster contains many genes involved in cell replication and proliferation. Examples include DNA replication licensing factors (MCM 6), topoisomerase 2A, and the oncogene B-Myb.

Marker Confirmation by in situ Hybridization (ISH)

Markers were also evaluated in clinical tissue samples by ISH. ISH experiments were performed using tissue microarrays to confirm transcriptional profiling results and to determine the cell types responsible for increased mRNA expression. Depending on the level of the paraffin block sectioned, 26-87 normal cervical tissue cores (from ectocervix and endocervix), 2-10 LSIL, 5-33 HSIL and 10-21 cancer cores (including SCC, ACA and poorly differentiated carcinomas) were examined. In general, the ISH signal was detected in cervical epithelial cells (Table 5). Genes that are overexpressed in epithelial cells are responsible for cell growth and cell-ECM interactions. Several genes were differentially expressed by the epithelial cells. This finding suggests coordinated gene regulation between cervical epithelium and its microenvironment during cancer progression.

Photomicrographs of a representative gene, claudin 1 were taken. There was little or no detectable signal from Claudin 1 probes in normal endo-/ectocervical tissues and LSIL. Gene expression was elevated in HSEL and increased further in cervical tumors. Claudin 1 expression was limited to the epithelium and was not significantly elevated in the 5 HSIL and 3 ACA samples that were profiled on cDNA microarrays (FIG. 2). Without being limited by theory, the increased sensitivity of ISH in this case could be due to the focal nature of the signal. Such focal signals are readily apparent by ISH but can be missed in RNA preparations of whole tissue homogenates.

Since cervical screening evaluates morphological changes of cells exfoliated from cervical epithelium, cells from stroma are unlikely to be present in a Pap test sample. The marker selection was therefore focused on those candidate markers that were differentially expressed in the epithelial cells of cervical dysplasias and invasive tumors. To understand the frequency with which each marker was elevated in different types of cervical lesions and tumors, a frequency calculation was performed using all tissue cores on the microarray. The calculation was based on a seni-quantitative, arbitrary scoring method. The signal was scored on a scale from 0 to 3: 0—no signal; 1—weak, indeterminate signal; 2—determinate, weak to moderate signal; 3—strong to very strong signal. Table 6 shows the results of the scoring for markers of the present invention. To be considered positive, a tissue core had to have a signal score of $\geq 2$. In cases where the microarray contained more than one tissue core from a single patient, a positive call required at least 50% of tissue cores to be $\geq 2$. To better visualize the results, the selected markers are presented in the order of increasing frequency of positive cores for normal cervical tissues. It was found that the frequency of marker elevation is highly correlated with the stage of clinical abnormality and varies in a broad range from marker to marker at particular clinical stages. IFI27, for example, had relatively high (>20%) positive cores from normal cervical tissues, whereas markers such as ITGB6 and CLDN1 were relatively lower in normals and started to increase in LSIL and HSIL. The appearance of positive cores for BST2 took place even later in the tumor progression stage, at the transition from high-grade premalignant lesions to invasive disease. These findings demonstrate the existence of markers that identify sequential molecular changes during cervical cancer development.

EXAMPLE 2

Gene Expression Analysis

RNA Preparation

Total RNA was prepared from various human tissues by a single step extraction method using TRIZOL Reagent according to the manufacturer's instructions (Invitrogen). Each RNA preparation was treated with DNase I (Ambion) at 37° C. for 1 hour. DNAse I treatment was determined to be complete if the sample required at least 38 PCR amplification cycles to reach a threshold level of fluorescence using $\beta$-2 microglobulin as an internal amplicon reference (or 35 PCR amplification cycles for 18s ribosome gene). The integrity of the RNA samples following DNase I treatment was confirmed by agarose gel electrophoresis and ethidium bromide staining. After phenol extraction, cDNA was prepared from the sample using the Taqman Reverse Transcription Reagents following the manufacturer's instructions (Applied Biosytems). A negative control of RNA without reverse transcriptase was mock reverse transcribed for each RNA sample.

TAQMAN®

Gene expression was measured by TAQMAN® quantitative PCR (Applied Biosystems) in cDNA prepared from a variety of normal and diseased (e.g., cancerous) human tissues or cell lines.

Preparation of Probes

Probes were designed by PrimerExpress™ software (Applied Biosystems) based on the sequence of the specific genes and their related transcripts. Each target gene probe was labeled using FAM (6-carboxyfluorescein), and the 18s reference probe was labeled with a different fluorescent dye, VIC. The differential labeling of the target gene and internal reference gene thus enabled measurement in the same well. Primer and probes were checked for their sensitivity and specificity for each transcript of the specific gene. Forward and reverse primers and the probes for both 18s and the target gene were added to the TAQMAN® Universal PCR Master Mix (Applied Biosystems). Although the final concentration of primer and probe could vary, each was internally consistent within a given experiment. A typical experiment contained 100 nM of forward and reverse primers plus 200 nM probe for 18s and 900 nM forward and reverse primers plus 250 nM probe for the target gene. TAQMAN® matrix experiments were carried out on an ABI PRISM® 7700 Sequence Detection System (Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate gene expression in the various tissues relative to 18s expression in the same tissue. The threshold cycle (Ct) value is defined as the cycle at which a statistically significant increase in fluorescence is detected. A lower Ct value is indicative of a higher mRNA concentration. The Ct value of the gene is normalized by subtracting the Ct value of the 18s ribosome gene to obtain a $\Delta$Ct value using the following formula: $\Delta Ct = Ct$ (target transcript)$-Ct$ (18s). Relative expression is then calculated using the arithmetic formula given by $2-\Delta Ct$. Expression of the target gene in each of the tissues tested is then numerically represented (Tables 9-13). Tables 9-13 identify the Sample (Sample #), Tissue Stage, and Expression of the target gene. The marker (set forth in Table 1) that was assayed is also identified along with the variant, primer and probe (set forth in Table 7), if applicable. For example, in Table 12, the data corresponding to M30A [1] identifies Marker M30A using the forward 1 (F1), reverse 1 (R1) and probe 1 (P1) as identified in Table 7.

Gene Expression Analysis by End-point PCR

Total RNA from different samples was pooled to be used as template to generate first strand cDNA. The cervical panel consisted of a cervical tumor pool, a cervical normal pool, an 'other normals' pool and an 'other tumors' pool. The pools consisted of equal amounts of each sample.

| TYPE OF POOL | CONSTITUENTS |
|---|---|
| Cervical Tumor Pool | 4 tumor samples (squamous cell carcinoma) |
| Cervical Normal Pool | 3 normal cervical samples |
| Other Tumors Pool | Cervical tumors - 4 squamous cell carcinoma samples |
| | Colon Tumors - 5 adenocarcinoma samples |
| | Lung Tumors - 3 squamous cell carcinomas, 3 adenocarcinomas, 1 bronchioalveolar carcinoma and 1 large cell undifferentiated carcinoma |
| | Ovarian Tumors - 2 serous carcinomas and 2 clear cell carcinomas |
| | Prostate Tumors - 5 adenocarcinomas |
| Other Normals Pool | One sample each from normal heart, kidney, small intestine, spleen, WBC, lung, liver, brain, bone marrow, and colon tissues |

ThermoScript RT-PCR System (Invitrogen, San Diego, Calif.) was used to obtain cDNA. 1 µg RNA was denatured at 65° C. for 5 min with 1 µl of 50 µM oligo (dT) 20 primer in a 10 µl volume according to the manufacturer's instructions. The reaction was terminated by incubation at 85° C. for 5 min. The final product was diluted with water to a final volume of 100 µl.

Gene specific primers were designed just outside or right at the start of the Open Reading Frame (Table 7). The PCR conditions were optimized for the primers and the size of the product expected. 2 µl of cDNA was used in a 20 µl reaction with touchdown cycling conditions. The products were run on an ethidium bromide containing agarose gel. The gel picture was then semi-quantitatively analyzed and scored.

The ethidium bromide agarose gel pictures of the end-point PCR on the tissue panel were scored on a scale of 0-5 (Table 8). Each picture was scored independently by 3 people and the results were compiled. The scores were compared to make sure that there was agreement on the relative intensities of the bands and modifications were made where needed. The median of the 3 scores was then recorded as the final score.

Summary of the Data Provided in the Tables

Tables 1 identifies markers of the invention (SEQ ID NOs:1-44), which are designated with a name ("Marker"), the name the gene is commonly known by, if applicable ("Gene Name"), the Sequence Listing identifier of the cDNA sequence of a nucleotide transcript encoded by or corresponding to the marker ("SEQ ID NO (nts)"), the Sequence Listing identifier of the amino acid sequence of a protein encoded by the nucleotide transcript ("SEQ ID NO (AAs)"), and the location of the protein coding sequence within the cDNA sequence ("CDS").

Tables 2 and 3 list newly-identified nucleotide and amino acid sequences, which are designated with a name ("Marker"), the name the gene is commonly known by, if applicable ("Gene Name"), the Sequence Listing identifier of the cDNA sequence of a nucleotide transcript encoded by or corresponding to the marker ("SEQ ID NO (nts)"), the Sequence Listing identifier of the amino acid sequence of a protein encoded by the nucleotide transcript ("SEQ ID NO (AAs)"), and the location of the protein coding sequence within the cDNA sequence ("CDS").

Table 4 identifies markers of the present invention and their marker scores in SCC, ACA and HSIL. The markers of Table 4 are designated with a name ("Marker"), the name the gene is commonly known by, if applicable ("Gene Name"), the marker score from the squamous cell carcinomas paradigm ("Score SCC"), the marker score from the adenocarcinomas paradigm ("Score ACA"), and the marker score from the high-grade squamous intraepithelial lesions paradigm ("Score HSIL").

Table 5 lists markers identified as overexpressed in cervical cancer by in situ hybridization and indicates the location of marker expression. The markers of Table 5 are designated with a name ("Marker"), the name the gene is commonly known by, if applicable ("Gene Name"), the in situ hybridization signal detected in cervical epithelial cells ("Signal Location").

Table 6 sets forth the differential expression of the markers in epithelial cells of cervical dysplasias and invasive tumors. The markers of Table 6 are designated with a name ("Marker"), the name the gene is commonly known by, if applicable ("Gene Name"), and for each marker, the frequency of marker elevation ("frequency") and the number of positives to the number of patients ("# positives/# patients") in normal ectocervical and endocervical cells ("Normal (EC+END)"), the frequency of marker elevation ("frequency") and the number of positives to the number of patients ("# positives/# patients") in low-grade squamous intraepithelial lesions ("LSIL"), the frequency of marker elevation ("frequency") and the number of positives to the number of patients ("# positives/# patients") in high-grade squamous intraepithelial lesions ("HSIL"), and the frequency of marker elevation ("frequency") and the number of positives to the number of patients ("# positives/# patients") in squamous cell carcinomas and adenocarcinomas ("Tumor (SCC+ACA)"), is set forth.

Table 7 sets forth gene specific primers. Table 7 identifies the marker, which are designated with a name ("Marker"), the gene specific primers corresponding to matching positions for Taqman Primer 1 ("Matching Positions: Taqman Primer 1"), the gene specific primers corresponding to matching positions for Taqman Primer 2 ("Matching Positions: Taqman Primer 2"), the gene specific primers corresponding to matching positions for Taqman Probe ("Matching Positions: Taqman Probe"), the gene specific primers corresponding to matching positions for Endpoint PCR Primer 1 ("Matching Positions: Endpoint PCR Primer 1"), and the gene specific primers corresponding to matching positions for Endpoint PCR Primer 1 ("Matching Positions: Endpoint PCR Primer 1"). Table 7 identifies primers in the forward 1 direction ("F1"); the forward 2 direction ("F2"); the reverse 1 direction ("R1"); the reverse 2 direction ("R2"), as well as the probes ("P1" designates probe 1; and "P2" designates probe 2).

Table 8 sets forth the scoring on a scale of 0-5 of ethidium bromide agarose gel pictures of the end-point PCR on the tissue panel. Table 8 identifies markers, which are designated with a name ("Marker"), and the samples used ("Cervical Normal" and "Cervical Tumor").

Tables 9-13 identify the expression of the target gene in each of the tissues tested. Tables 9-13 identify the Sample, which is designated with a number ("Sample #"), the tissue stage of the sample ("Tissue Stage"), and expression of the target gene ("Gene Name"). Tables 9-13 also identify the marker name, corresponding to the marker names set forth in Table 1, primer and probe (set forth in Table 7), if applicable, that were assayed. For example, in Table 12, the data corresponding to "M30A[1]" identifies Marker M30A using the forward 1 primer (F1), reverse 1 primer (R1) and probe 1 (P1) as identified in Table 7.

The markers obtained using the foregoing protocol should not be construed as limiting. The contents of all references, databases, patents and published patent applications cited throughout this application are expressly incorporated herein by reference.

Other Embodiments

Those skilled in the art will recognize, or be able to ascertain using no more than routine experimentation, many equivalents to the specific embodiments of the invention described herein. Such equivalents are intended to be encompassed by the following claims:

TABLE 1

Sequence-Related Information

| Marker | Gene Name | SEQ ID NO (nts) | SEQ ID NO (AAs) | CDS |
|---|---|---|---|---|
| M1A | APOL1: apolipoprotein L1 | 1 | 2 | 162 . . . 1358 |
| M718 | APOL2: apolipoprotein L2 | 3 | 4 | 337 . . . 1350 |
| OV3A | AQP5: aquaporin 5, variant 1 | 5 | 6 | 517 . . . 1314 |
| M719 | AQP5: aquaporin 5, variant 2 | 7 | 8 | 517 . . . 1149 |
| M720 | AQP5: aquaporin 5, variant 3 | 9 | 10 | 517 . . . 1185 |
| M5A | BST2: bone marrow stromal cell antigen 2 | 11 | 12 | 78 . . . 620 |
| M10A | CLDN1: claudin-1, senescence-associated epithelial membrane protein 1 | 13 | 14 | 221 . . . 856 |
| M29A | COTL1: coactosin-like 1 (Dictyostelium) | 15 | 16 | 150 . . . 576 |
| M30A | IFI27: interferon, alpha-inducible protein 27, variant 1 | 17 | 18 | 120 . . . 488 |
| M721 | IFI27: interferon, alpha-inducible protein 27, variant 2 | 19 | 20 | 120 . . . 479 |
| M488A | ITGA3: integrin, alpha 3 (antigen CD49C, alpha 3 subunit of VLA-3 receptor) | 21 | 22 | 240 . . . 3353 |
| M35 | ITGB6: integrin, beta 6, variant 1 | 23 | 24 | 195 . . . 2561 |
| M722 | ITGB6: integrin, beta 6, variant 2 | 25 | 26 | 241 . . . 2388 |
| M723 | ITGB6: integrin, beta 6, variant 3 | 27 | 28 | 195 . . . 2240 |
| M666 | KCNAB1: potassium voltage-gated channel, shaker-related subfamily, beta member | 29 | 30 | 89 . . . 1315 |
| M489A | MCM6: minichromosome maintenance deficient (mis5, *S. pombe*) 6 | 31 | 32 | 56 . . . 2521 |
| OV43A | MSLN: mesothelin, megakaryocyte potentiating factor | 33 | 34 | 88 . . . 1956 |
| M51A | MYBL2: B-MYB, transcription factor (v-myb myeloblastosis viral oncogene homolog | 35 | 36 | 128 . . . 2230 |
| M58 | PLAU: plasminogen activator, urokinase | 37 | 38 | 77 . . . 1372 |
| M22A | RTP801: hypoxia-inducible factor 1(HIF-1) responsive gene | 39 | 40 | 198 . . . 896 |
| M74A | TOP2A: DNA topoisomerase II, alpha isozyme | 41 | 42 | 127 . . . 4722 |
| M78 | ZNF-P66: C2H2 type zinc finger protein (66 kD) | 43 | 44 | 45 . . . 1343 |

TABLE 2

Sequence-Related Information

| Marker | Gene Name | SEQ ID NO (nts) | SEQ ID NO (AAs) | CDS |
|---|---|---|---|---|
| M1A | APOL1: apolipoprotein L1 | 1 | 2 | 162 . . . 1358 |
| M719 | AQP5: aquaporin 5, variant 2 | 7 | 8 | 517 . . . 1149 |
| M720 | AQP5: aquaporin 5, variant 3 | 9 | 10 | 517 . . . 1185 |
| M721 | IFI27: interferon, alpha-inducible protein 27, variant 2 | 19 | 20 | 120 . . . 479 |
| M488A | ITGA3: integrin, alpha 3 (antigen CD49C, alpha 3 subunit of VLA-3 receptor) | 21 | 22 | 240 . . . 3353 |
| M722 | ITGB6: integrin, beta 6, variant 2 | 25 | 26 | 241 . . . 2388 |
| M723 | ITGB6: integrin, beta 6, variant 3 | 27 | 28 | 195 . . . 2240 |
| M78 | ZNF-P66: C2H2 type zinc finger protein (66 kD) | 43 | 44 | 45 . . . 1343 |

TABLE 3

Sequence-Related Information

| Marker | Gene Name | SEQ ID NO (nts) | SEQ ID NO (AAs) | CDS |
|---|---|---|---|---|
| M5A | BST2: bone marrow stromal cell antigen 2 | 11 | 12 | 78 . . . 620 |

TABLE 3-continued

Sequence-Related Information

| Marker | Gene Name | SEQ ID NO (nts) | SEQ ID NO (AAs) | CDS |
|---|---|---|---|---|
| M30A | IFI27: interferon, alpha-inducible protein 27, variant 1 | 17 | 18 | 120 . . . 488 |
| M35 | ITGB6: integrin, beta 6, variant 1 | 23 | 24 | 195 . . . 2561 |
| OV43A | MSLN: mesothelin, megakaryocyte potentiating factor | 33 | 34 | 88 . . . 1956 |

TABLE 4

| Marker | Gene Name | Score SCC | Score ACA | Score HSIL |
|---|---|---|---|---|
| M666 | KCNAB1: potassium voltage-gated channel, shaker-related subfamily, beta member 1 | 3.6 | 3.9 | 1.4 |
| M10A | CLDN1: claudin-1, senescence-associated epithelial membrane protein 1 | 3.3 | 1.0 | 1.3 |
| M29A | COTL1: coactosin-like 1 (Dictyostelium) | 3.2 | 1.9 | 1.0 |
| M5A | BST2: bone marrow stromal cell antigen 2 | 3.1 | 3.5 | 1.7 |
| M78 | ZNF-P66: C2H2 type zinc finger protein (66 kD) | 3.0 | 3.1 | 1.4 |
| M22A | RTP801: hypoxia-inducible factor 1(HIF-1) responsive gene | 2.9 | 3.0 | 1.4 |
| M30A M721 | IFI27: interferon, alpha-inducible protein 27, variants 1 and 2 | 2.9 | 2.5 | 1.2 |
| M1A | APOL1: apolipoprotein L1 | 2.8 | 3.1 | 1.9 |
| M488A | ITGA3: integrin, alpha 3 (antigen CD49C, alpha 3 subunit of VLA-3 receptor) | 2.7 | 3.7 | 1.1 |
| M35 M722 M723 | ITGB6: integrin, beta 6, variants 1, 2, and 3 | 2.4 | 3.9 | 1.0 |
| M51A | MYBL2: B-MYB, transcription factor (v-myb myeloblastosis viral oncogene homolog (avian)-like 2) | 2.3 | 4.2 | 1.8 |
| M489A | MCM6: minichromosome maintenance deficient (mis5, *S. pombe*) 6 | 2.3 | 3.2 | 1.5 |
| M74A | TOP2A: DNA topoisomerase II, alpha isozyme | 1.7 | 3.2 | 1.6 |
| OV3A M719 M720 | AQP5: aquaporin 5, variants 1, 2, and 3 | 1.0 | 3.2 | 1.6 |

TABLE 5

| Marker | Gene Name | Signal Location |
|---|---|---|
| M666 | KCNAB1: potassium voltage-gated channel, shaker-related subfamily, beta member 1 | epithelium |
| M29A | COTL1: coactosin-like 1 (Dictyostelium) | epithelium |
| M74A | TOP2A: DNA topoisomerase II, alpha isozyme | epithelium |
| M30A M721 | IFI27: interferon, alpha-inducible protein 27, variants 1 and 2 | epithelium |
| M78 | ZNF-P66: C2H2 type zinc finger protein (66 kD) | epithelium |
| M488A | ITGA3: integrin, alpha 3 (antigen CD49C, alpha 3 subunit of VLA-3 receptor) | epithelium |
| OV3A M719 M720 | AQP5: aquaporin 5, variants 1, 2, and 3 | epithelium |
| M5A | BST2: bone marrow stromal cell antigen 2 | epithelium |
| M22A | RTP801: hypoxia-inducible factor 1(HIF-1) responsive gene | epithelium |
| M51A | MYBL2: B-MYB, transcription factor (v-myb myeloblastosis viral oncogene homolog (avian)-like 2) | epithelium |
| M35 M722 M723 | ITGB6: integrin, beta 6, variants 1, 2, and 3 | epithelium |
| M16 | CRIP1: cysteine-rich protein 1 (intestinal) | epithelium |
| M489A | MCM6: minichromosome maintenance deficient (mis5, *S. pombe*) 6 | epithelium |
| M10A | CLDN1: claudin-1, senescence-associated epithelial membrane protein 1 | epithelium |
| M1A | APOL1: apolipoprotein L1 | epithelium |

TABLE 6

| Marker | Tissue Gene Name | Normal (EC + END)[b] frequency | # positive/ # patients | LSIL frequency | # positive/ # patients | HSIL frequency | # positive/ # patients | Tumor (SCC + ACA) frequency | # positive/ # patients |
|---|---|---|---|---|---|---|---|---|---|
| M74A | TOP2A: DNA topoisomerase II, alpha Isozyme | 0.0% | 0/47 | 0.0% | 0/2 | 20.0% | 2/10 | 23.1% | 3/13 |
| M51A | MYBL2: B-MYB, transcription factor (v-myb myeloblastosis viral oncogene homolog (avian)-like2) | 0.0% | 0/59 | 16.7% | 1/6 | 27.8% | 5/18 | 75.0% | 12/16 |
| M489A | MCM6: minichromosome maintenance deficient (mis5, S. pombe) 6 | 1.8% | 1/56 | 0.0% | 0/7 | 80.0% | 12/15 | 75.0% | 12/16 |
| M5A | BST2: bone marrow stromal cell antigen 2 | 3.5% | 3/85 | 10.0% | 1/10 | 13.3% | 2/15 | 68.4% | 13/19 |
| M78 | ZNF-P66: C2H2 type zinc finger protein (66 kD) | 4.6% | 3/65 | 0.0% | 0/5 | 0.0% | 0/12 | 30.0% | 3/10 |
| OV3A M719 M720 | AQP5: aquaporin 5, variants 1, 2, and 3 | 5.0% | 2/40 | 50.0% | 2/4 | 20.0% | 1/5 | 43.8% | 7/16 |
| M22A | RTP801: hypoxia-inducible factor 1 (HIF-1) responsive gene | 9.2% | 7/76 | 0% | 0/4 | 40.0% | 8/20 | 41.6% | 5/12 |
| M35 M722 | ITGB6: integrin, beta 6, variants 1 and 2 | 11.1% | 6/54 | 100.0% | 3/3 | 53.3% | 8/15 | 88.2% | 15/17 |
| M488A | ITGA3: integrin, alpha 3 (antigen CD49C, alpha 3 subunit of VLA-3 receptor) | 11.9% | 7/59 | 0.0% | 0/3 | 20.0% | 2/10 | 75.0% | 9/12 |
| M29A | COTL1: coactosin-like 1 (Dictyostelium) | 14.3% | 8/56 | 20.0% | 2/10 | 7.7% | 1/13 | 64.3% | 9/14 |
| M10A | CLDN1: claudin-1, senescence-associated epithelial membrane protein 1 | 15.1% | 8/53 | 75.0% | 3/4 | 88.2% | 15/17 | 90.5% | 19/21 |
| M30A M721 | IFI27: interferon, alpha-inducible protein 27, variants 1 and 2 | 23.0% | 20/87 | 33.3% | 3/9 | 42.0% | 10/24 | 66.7% | 12/18 |

[a]positive tissue cores were those which have ISH scores ≧2.
[b]normal ectocervical and endocervical cells.
[c]expression in some normal squamous epithelium restricted to basal/parabasal cells. shaded cells indicate ISH scores ≧2 in at least 20% of the patients.

TABLE 7

Taqman/PCR primer-related information

| Marker | Matching positions: Taqman Primer 1 | Matching positions: Taqman Primer 2 | Matching positions: Taqman Probe | Matching positions: Endpoint PCR Primer 1 | Matching positions: Endpoint PCR Primer 2 |
|---|---|---|---|---|---|
| M1A | 99-121 | 238-218 | 186-160 | 82-103 | 1673-1693 |
| M718 | 166-188 | 251-231 | 190-217 | 143-164 | 1680-1700 |
| OV3A | 914-935 | 980-964 | 938-961 | 512-534 | 1432-1449 |
| M719 | 842-857 | 912-895 | 869-894 | 512-534 | 1267-1284 |
| M720 | 1097-1116 | 1174-1155 | 1154-1133 | 512-534 | 1512-1529 |
| M5A | | | | 1-23; 34-56 | 628-647 |
| M10A | | | | 164-182 | 888-908 |
| M29A | | | | 123-139 | 592-610 |
| M30A | (F1) 208-228//(F2) 257-275 | (R1) 315-298//(R2) 336-316 | (P1) 260-242//(P2) 277-296 | 7-26 | 510-529 |
| M721 | (F1) 208-228//(F2) 248-266 | (R1) 306-289//(R2) 327-307 | (P1) 258-234//(P2) 268-287 | 7-26 | 501-520 |
| M488A | | | | 187-209 | 3412-3434 |
| M35 | (F1) 1900-1920//(F2) 628-648 | (R1) 1970-1950//(R2) 698-672 | (P1) 1923-1945//(P2) 670-650 | 188-208 | 2592-2616 |
| M722 | (F1) 1727-1747//(F2) 318-337//(F3) 455-475 | (R1) 1797-1777//(R2) 409-391//(R3) 525-499 | (P1) 1750-1772//(P2) 377-360//(P3) 497-477 | 188-208 | 2419-2443 |
| M723 | (F1) 1796-1818//(F2) 628-648 | (R1) 1891-1870//(R2) 698-672 | (P1) 1869-1843//(P2) 670-650 | 188-208 | 2271-2295 |

TABLE 7-continued

Taqman/PCR primer-related information

| Marker | Matching positions: Taqman Primer 1 | Matching positions: Taqman Primer 2 | Matching positions: Taqman Probe | Matching positions: Endpoint PCR Primer 1 | Matching positions: Endpoint PCR Primer 2 |
|---|---|---|---|---|---|
| M666 | | | | 89-108 | 1288-1312 |
| M489A | | | | 21-39 | 2563-2580 |
| OV43A | | | | 1198-1215 | 1272-1290 |
| M51A | | | | 216-233 | 2291-2315 |
| M58 | | | | 52-70 | 1396-1415 |
| M22A | | | | 139-159 | 997-1017 |
| M74A | | | | | |
| M78 | | | | 6-25 | 1393-1418 |

TABLE 8

| Marker | Cervical Normal | Cervical Tumor |
|---|---|---|
| M1A | 1 | 5 |
| M718 | 1 | 3 |
| OV3A | 1 | 4 |
| M719 | 1 | 4 |
| M720 | 1 | 4 |
| M5A | 3 | 3 |
| M10A | 3 | 5 |
| M29A | 2 | 5 |
| M30A | 4 | 5 |
| M721 | 4 | 5 |
| M488A | 2 | 5 |
| M35 | 0 | 5 |
| M722 | 0 | 5 |
| M723 | 0 | 5 |
| M666 | 0 | 5 |
| M489A | 2 | 5 |
| OV43A | 0 | 4 |
| M51A | 0 | 5 |
| M58 | 2 | 2 |
| M22A | 1 | 5 |
| M74A | | |
| M78 | 0 | 2 |

TABLE 9

Expression of Aquaporin 5

| Sample # | Tissue Stage | OV3A | M719 | M720 |
|---|---|---|---|---|
| 1 | normal | 0.37 | 0.01 | 0.00 |
| 2 | normal | 0.02 | 0.00 | 0.00 |
| 3 | normal | 0.98 | 0.01 | 0.02 |
| 4 | normal | 0.01 | 0.00 | 0.00 |
| 5 | normal | 0.39 | 0.01 | 0.01 |
| 6 | normal | 0.00 | 0.00 | 0.00 |
| 7 | normal | 1.59 | 0.07 | 0.01 |
| 8 | normal | 0.12 | 0.00 | 0.00 |
| 9 | normal | 0.00 | 0.00 | 0.00 |
| 10 | normal | 0.00 | 0.00 | 0.00 |
| 11 | SCC | 0.79 | 0.05 | 0.01 |
| 12 | SCC | 0.23 | 0.01 | 0.00 |
| 13 | SCC | 0.17 | 0.00 | 0.01 |
| 14 | SCC | 0.66 | 0.03 | 0.01 |
| 15 | SCC | 1.37 | 0.03 | 0.00 |
| 16 | SCC | 3.22 | 0.33 | 0.02 |
| 17 | SCC | 0.00 | 0.00 | 0.00 |
| 18 | SCC/AIS | 0.12 | 0.00 | 0.00 |
| 19 | SSC | 0.02 | 0.00 | 0.00 |
| 20 | poorly diff. adenosquamous | 0.18 | 0.01 | 0.00 |
| 21 | SSC | 0.01 | 0.00 | 0.00 |
| 22 | Adenocarcinoma | 0.02 | 0.00 | 0.00 |
| 23 | Adenocarcinoma | 0.78 | 0.03 | 0.01 |
| 24 | SCC | 0.12 | 0.01 | 0.00 |
| 25 | SSC | 0.00 | 0.00 | 0.00 |
| 26 | SSC | 0.00 | 0.00 | 0.00 |
| 27 | SSC | 0.00 | 0.00 | 0.00 |
| 28 | SSC | 0.08 | 0.01 | 0.00 |
| 29 | SSC | 1.59 | 0.06 | 0.02 |
| 30 | SSC | 0.07 | 0.00 | 0.00 |
| 31 | Adenocarcinoma | 0.27 | 0.01 | 0.00 |
| 32 | Adenocarcinoma | 1.29 | 0.03 | 0.03 |
| 33 | SCC | 0.03 | 0.00 | 0.00 |
| 34 | SSC | 0.01 | 0.00 | 0.00 |
| 35 | SSC | 6.92 | 0.11 | 0.05 |
| 36 | SSC | 0.03 | 0.00 | 0.00 |
| 37 | SSC | 0.15 | 0.00 | 0.00 |
| 38 | SSC | 0.00 | 0.00 | 0.00 |
| 39 | SSC | 0.01 | 0.00 | 0.00 |
| 40 | SSC | 0.06 | 0.00 | 0.00 |
| 41 | SSC | 0.02 | 0.00 | 0.00 |
| 42 | tumor | 0.13 | 0.00 | 0.00 |

TABLE 10

Expression of Apolipoprotein L1

| Sample # | Tissue Stage | M1A |
|---|---|---|
| 1 | normal | 0.60 |
| 2 | normal | 0.14 |
| 3 | normal | 0.60 |
| 4 | normal | 0.48 |
| 5 | normal | 0.44 |
| 6 | normal | 0.24 |
| 7 | normal | 0.18 |
| 8 | normal | 0.34 |
| 9 | normal | 0.52 |
| 10 | normal | 0.62 |
| 11 | SCC | 1.56 |
| 12 | SCC | 2.02 |
| 13 | SCC | 2.50 |
| 14 | SCC | 3.15 |
| 15 | SCC | 1.14 |
| 16 | SCC | 3.42 |
| 17 | SCC | 2.51 |
| 18 | SCC/AIS | 17.88 |
| 19 | SSC | 1.18 |
| 20 | poorly diff. adenosquamous | 1.32 |
| 21 | SSC | 1.38 |
| 22 | Adenocarcinoma | 6.61 |
| 23 | Adenocarcinoma | 0.08 |
| 24 | SCC | 1.37 |
| 25 | SSC | 6.28 |

TABLE 10-continued

Expression of Apolipoprotein L1

| Sample # | Tissue Stage | M1A |
| --- | --- | --- |
| 26 | SSC | 1.91 |
| 27 | SSC | 5.14 |
| 28 | SSC | 0.59 |
| 29 | SSC | 0.30 |
| 30 | SSC | 5.30 |
| 31 | Adenocarcinoma | 2.10 |
| 32 | Adenocarcinoma | 1.51 |
| 33 | SCC | 8.09 |
| 34 | SSC | 0.35 |
| 35 | SSC | 0.38 |
| 36 | SSC | 4.11 |
| 37 | SSC | 1.83 |
| 38 | SSC | 3.99 |
| 39 | SSC | 4.48 |
| 40 | SSC | 3.77 |
| 41 | SSC | 10.08 |
| 42 | tumor | 0.12 |

TABLE 11

Expression of Apolipoprotein L2

| Sample # | Tissue Stage | M718 |
| --- | --- | --- |
| 1 | normal | 0.20 |
| 2 | normal | 0.06 |
| 3 | normal | 0.19 |
| 4 | normal | 0.15 |
| 5 | normal | 0.20 |
| 6 | normal | 0.15 |
| 7 | normal | 0.13 |
| 8 | normal | 0.26 |
| 9 | normal | 0.32 |
| 10 | normal | 0.34 |
| 11 | SCC | 1.15 |
| 12 | SCC | 0.42 |
| 13 | SCC | 0.67 |
| 14 | SCC | 0.93 |
| 15 | SCC | 0.51 |
| 16 | SCC | 0.69 |
| 17 | SCC | 0.54 |
| 18 | SCC/AIS | 0.75 |
| 19 | SSC | 0.36 |
| 20 | poorly diff. adenosquamous | 0.67 |
| 21 | SSC | 0.30 |
| 22 | Adenocarcinoma | 0.82 |
| 23 | Adenocarcinoma | 0.11 |
| 24 | SCC | 0.52 |
| 25 | SSC | 2.68 |
| 26 | SSC | 0.51 |
| 27 | SSC | 1.82 |
| 28 | SSC | 0.51 |
| 29 | SSC | 0.17 |
| 30 | SSC | 1.90 |
| 31 | Adenocarcinoma | 0.34 |
| 32 | Adenocarcinoma | 0.49 |
| 33 | SCC | 1.82 |
| 34 | SSC | 0.11 |
| 35 | SSC | 0.28 |
| 36 | SSC | 0.62 |
| 37 | SSC | 0.55 |
| 38 | SSC | 0.68 |
| 39 | SSC | 0.72 |
| 40 | SSC | 0.38 |

TABLE 11-continued

Expression of Apolipoprotein L2

| Sample # | Tissue Stage | M718 |
| --- | --- | --- |
| 41 | SSC | 0.87 |
| 42 | tumor | 0.34 |

TABLE 12

Expression of Interferon, Alpha-Inducible Protein 27

| Sample # | Tissue Stage | M30A [1] | M721 [1] | M30A [2]/M721 [2] |
| --- | --- | --- | --- | --- |
| 1 | normal | 1.75 | 1.77 | 3.84 |
| 2 | normal | 0.21 | 1.25 | 1.44 |
| 3 | normal | 2.73 | 4.15 | 9.46 |
| 4 | normal | 0.00 | 39.85 | 17.37 |
| 5 | normal | 14.62 | 29.54 | 62.89 |
| 6 | normal | 14.47 | 20.68 | 32.12 |
| 7 | normal | 1.04 | 12.95 | 8.31 |
| 8 | normal | 4.56 | 8.96 | 15.70 |
| 9 | normal | 18.02 | 23.27 | 46.52 |
| 10 | normal | 5.83 | 39.68 | 32.94 |
| 11 | SCC | 6.66 | 7.60 | 15.26 |
| 12 | SCC | 0.98 | 5.48 | 5.08 |
| 13 | SCC | 0.00 | 24.93 | 14.39 |
| 14 | SCC | 3.58 | 26.17 | 19.23 |
| 15 | SCC | 12.51 | 8.70 | 37.53 |
| 16 | SCC | 0.00 | 366.10 | 244.10 |
| 17 | SCC | 23.94 | 78.32 | 127.98 |
| 18 | SCC/AIS | 32.25 | 287.87 | 251.55 |
| 19 | SSC | 4.24 | 3.31 | 15.21 |
| 20 | poorly diff. adenosquamous | 6.88 | 6.04 | 24.17 |
| 21 | SSC | 6.51 | 5.44 | 17.83 |
| 22 | Adenocarcinoma | 14.72 | 74.02 | 110.70 |
| 23 | Adenocarcinoma | 0.06 | 0.05 | 0.25 |
| 24 | SCC | 11.61 | 7.58 | 32.57 |
| 25 | SSC | 0.00 | 117.40 | 71.70 |
| 26 | SSC | 0.00 | 73.80 | 35.81 |
| 27 | SSC | 11.76 | 6.31 | 31.11 |
| 28 | SSC | 14.72 | 9.34 | 31.94 |
| 29 | SSC | 0.67 | 0.42 | 2.69 |
| 30 | SSC | 34.47 | 33.49 | 107.11 |
| 31 | Adenocarcinoma | 0.00 | 10.66 | 5.03 |
| 32 | Adenocarcinoma | 6.97 | 5.66 | 16.30 |
| 33 | SCC | 17.92 | 97.36 | 101.33 |
| 34 | SSC | 11.51 | 7.52 | 22.49 |
| 35 | SSC | 6.89 | 42.12 | 38.96 |
| 36 | SSC | 2.73 | 35.04 | 25.04 |
| 37 | SSC | 13.85 | 7.68 | 34.26 |
| 38 | SSC | 0.00 | 28.34 | 18.79 |
| 39 | SSC | 20.60 | 15.88 | 94.41 |
| 40 | SSC | 0.00 | 13.33 | 9.11 |
| 41 | SSC | 10.09 | 12.91 | 40.59 |
| 42 | tumor | 0.41 | 0.68 | 2.13 |

TABLE 13

Expression of Integrin, Beta 6

| Sample # | Tissue Stage | M35 [1]/ M722 [1] | M722 [2] | M723 [1] | M35 [2]/M722 [3]/ M723 [2] |
|---|---|---|---|---|---|
| 1 | normal | 0.45 | 0.0005 | 0.019 | 0.57 |
| 2 | normal | 0.21 | 0.0002 | 0.006 | 0.32 |
| 3 | normal | 0.09 | 0.0001 | 0.001 | 0.17 |
| 4 | normal | 0.13 | 0.0002 | 0.003 | 0.27 |
| 5 | normal | 0.11 | 0.0002 | 0.012 | 0.18 |
| 6 | normal | 0.55 | 0.0004 | 0.014 | 0.72 |
| 7 | normal | 0.11 | 0.0001 | 0.003 | 0.13 |
| 8 | normal | 0.08 | 0.0000 | 0.003 | 0.09 |
| 9 | normal | 0.27 | 0.0002 | 0.006 | 0.26 |
| 10 | normal | 0.56 | 0.0005 | 0.016 | 0.77 |
| 11 | SCC | 1.42 | 0.0016 | 0.058 | 1.90 |
| 12 | SCC | 0.25 | 0.0004 | 0.007 | 0.56 |
| 13 | SCC | 8.24 | 0.0033 | 0.333 | 10.81 |
| 14 | SCC | 0.26 | 0.0001 | 0.003 | 0.29 |
| 15 | SCC | 0.55 | 0.0003 | 0.014 | 0.62 |
| 16 | SCC | 1.22 | 0.0008 | 0.032 | 1.57 |
| 17 | SCC | 3.46 | 0.0048 | 0.181 | 5.36 |
| 18 | SCC/AIS | 1.58 | 0.0004 | 0.107 | 2.45 |
| 19 | SSC | 0.39 | 0.0004 | 0.023 | 0.66 |
| 20 | poorly diff. adenosquamous | 0.56 | 0.0005 | 0.022 | 0.91 |
| 21 | SSC | 2.92 | 0.0013 | 0.092 | 3.95 |
| 22 | Adenocarcinoma | 0.48 | 0.0002 | 0.012 | 0.68 |
| 23 | Adenocarcinoma | 0.30 | 0.0003 | 0.002 | 0.56 |
| 24 | SCC | 1.75 | 0.0010 | 0.083 | 3.34 |
| 25 | SSC | 0.43 | 0.0003 | 0.029 | 0.79 |
| 26 | SSC | 0.31 | 0.0004 | 0.018 | 0.46 |
| 27 | SSC | 0.60 | 0.0009 | 0.026 | 0.89 |
| 28 | SSC | 3.30 | 0.0025 | 0.131 | 4.45 |
| 29 | SSC | 2.28 | 0.0037 | 0.124 | 4.37 |
| 30 | SSC | 0.54 | 0.0007 | 0.021 | 0.87 |
| 31 | Adenocarcinoma | 0.27 | 0.0002 | 0.007 | 0.58 |
| 32 | Adenocarcinoma | 0.27 | 0.0003 | 0.012 | 0.35 |
| 33 | SCC | 3.46 | 0.0036 | 0.127 | 4.77 |
| 34 | SSC | 0.67 | 0.0004 | 0.036 | 1.19 |
| 35 | SSC | 0.94 | 0.0003 | 0.047 | 1.06 |
| 36 | SSC | 1.66 | 0.0004 | 0.057 | 1.74 |
| 37 | SSC | 2.20 | 0.0016 | 0.086 | 3.34 |
| 38 | SSC | 0.46 | 0.0002 | 0.008 | 0.41 |
| 39 | SSC | 0.82 | 0.0004 | 0.030 | 0.74 |
| 40 | SSC | 0.41 | 0.0002 | 0.013 | 0.29 |
| 41 | SSC | 3.04 | 0.0021 | 0.076 | 2.69 |
| 42 | tumor | 0.07 | 0.0000 | 0.001 | 0.06 |

What is claimed is:

1. A method of assessing whether a patient is afflicted with cervical carcinoma, the method comprising comparing:
   a) the level of expression of a marker in a patient cervical sample, wherein the marker is the M666 marker, and
   b) the level of expression of the marker in a normal control cervical sample,
   wherein a significant difference between the level of expression of the marker in the patient cervical sample and in the normal control cervical sample is an indication that the patient is afflicted with cervical carcinoma.

2. The method of claim 1, wherein the patient cervical sample comprises cervical cells obtained from the patient.

3. The method of claim 2, wherein the patient cervical sample is a cervical smear.

4. The method of claim 2, wherein the cervical_cells are in a fluid selected from the group consisting of a fluid collected by peritoneal rinsing, a fluid collected by uterine rinsing, a uterine fluid, a uterine exudate, a pleural fluid, a cystic fluid, and an cervical exudate.

5. The method of claim 1, wherein the level of expression of the marker in the patient cervical sample is assessed by detecting the presence in the patient cervical sample of a protein corresponding to the marker.

6. The method of claim 5, wherein the presence of the protein is detected using a reagent which specifically binds with the protein, wherein the reagent is selected from the group consisting of an antibody and an antigen binding fragment thereof.

7. The method of claim 1, wherein the level of expression of the marker in the patient cervical sample is assessed by detecting the presence in the sample of a transcribed polynucleotide or portion thereof, wherein the transcribed polynucleotide comprises the marker.

8. The method of claim 7, wherein the transcribed polynucleotide is an mRNA.

9. The method of claim 7, wherein the transcribed polynucleotide is a cDNA.

10. The method of claim 7, wherein the step of detecting further comprises amplifying the transcribed polynucleotide.

11. The method of claim 1, wherein the level of expression of the marker in the patient cervical sample is assessed by detecting the presence in the sample of a transcribed polynucleotide which anneals with the marker or anneals with a portion of a polynucleotide wherein the polynucleotide comprises the marker, under stringent hybridization conditions comprising 45° C. in 6×sodium chloride/sodium citrate(SSC), followed by washing in 0.2×SSC, 0.1% SDS, at 50-65° C.

12. The method of claim 1, wherein the level of expression of the marker in the patient cervical sample differs from the level of expression of the marker in the normal control cervical sample by a factor of at least about 2.

13. The method of claim 1, wherein the level of expression of the marker in the patient cervical sample differs from the level of expression of the marker the normal control cervical sample by a factor of at least about 5.

14. The method of claim 1, further comprising comparing:
   a) the level of expression in the patient cervical sample of each of a plurality of markers independently selected from the markers listed in Table 1, and
   b) the level of expression of each of the plurality of markers in the normal control cervical,
   wherein a significant difference between the level of expression of more than one of the markers in the patient cervical sample and in the normal control cervical sample is a further indication that the patient is afflicted with cervical carcinoma.

15. The method of claim 14, wherein a significant difference between the level of expression of each of said plurality of markers in the patient cervical sample and the normal control cervical sample is a further indication that the patient is afflicted with cervical carcinoma.

16. The method of claim 14, wherein the plurality comprises at least three of the markers.

17. The method of claim 14, wherein the plurality comprises at least five of the markers.

18. The method of claim 1, wherein the cervical carcinoma is adenocarcinoma.

19. The method of claim 1, wherein the cervical carcinoma is squamous cell carcinoma.

20. The method of claim 18, wherein the level of expression of the marker in the cervical adenocarcinoma differs from the normal level of expression of the marker in a patient not afflicted with cervical cancer by a factor of at least about 2.

21. The method of claim 19, wherein the level of expression of the marker in the cervical squamous cell carcinoma differs from the normal level of expression of the marker in a patient not afflicted with cervical cancer by a factor of at least about 2.

22. The method of claim 2, wherein the patient cervical sample comprises a cervical epithelial cell.

* * * * *